(12) United States Patent
Jacky et al.

(10) Patent No.: US 11,149,262 B2
(45) Date of Patent: Oct. 19, 2021

(54) BOTULINUM TOXIN CELL BINDING DOMAIN POLYPEPTIDES AND METHODS OF USE FOR SKIN REJUVENATION

(71) Applicant: Allergan, Inc., Irvine, CA (US)

(72) Inventors: Birgitte P S Jacky, Orange, CA (US); Amy Brideau-Andersen, San Clemente, CA (US); Hui You, Irvine, CA (US); Shiazah Z. Malik, Irvine, CA (US); Donald E. Frail, Laguna Hills, CA (US); Mitchell F. Brin, Newport Beach, CA (US)

(73) Assignee: Alleergan, Inc., Irvine, CA (US)

( * ) Notice: Subject to any disclaimer, the term of this patent is extended or adjusted under 35 U.S.C. 154(b) by 0 days.

(21) Appl. No.: 16/227,027

(22) Filed: Dec. 20, 2018

(65) Prior Publication Data

US 2019/0185523 A1  Jun. 20, 2019

Related U.S. Application Data

(60) Provisional application No. 62/727,640, filed on Sep. 6, 2018, provisional application No. 62/608,119, filed on Dec. 20, 2017.

(51) Int. Cl.

| | | |
|---|---|---|
| *A61P 17/10* | (2006.01) | |
| *A61P 17/06* | (2006.01) | |
| *C12N 9/52* | (2006.01) | |
| *A61K 38/48* | (2006.01) | |
| *A61K 9/00* | (2006.01) | |
| *A61P 35/00* | (2006.01) | |
| *A61P 13/10* | (2006.01) | |
| *A61P 13/08* | (2006.01) | |
| *A61P 1/18* | (2006.01) | |
| *A61P 17/02* | (2006.01) | |
| *A61P 37/00* | (2006.01) | |
| *A61P 17/08* | (2006.01) | |
| *A61P 29/00* | (2006.01) | |
| *A61Q 19/00* | (2006.01) | |
| *A61Q 19/08* | (2006.01) | |
| *C07K 14/315* | (2006.01) | |
| *C07K 14/33* | (2006.01) | |

(52) U.S. Cl.
CPC .............. *C12N 9/52* (2013.01); *A61K 9/0014* (2013.01); *A61K 9/0019* (2013.01); *A61K 38/4893* (2013.01); *A61P 1/18* (2018.01); *A61P 13/08* (2018.01); *A61P 13/10* (2018.01); *A61P 17/02* (2018.01); *A61P 17/06* (2018.01); *A61P 17/08* (2018.01); *A61P 17/10* (2018.01); *A61P 29/00* (2018.01); *A61P 35/00* (2018.01); *A61P 37/00* (2018.01); *A61Q 19/007* (2013.01); *A61Q 19/008* (2013.01); *A61Q 19/08* (2013.01); *C07K 14/315* (2013.01); *C07K 14/33* (2013.01); *C12Y 304/24069* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 7,226,605 B2 * | 6/2007 | Suskind | A61P 17/10 424/247.1 |
| 2005/0095251 A1 | 5/2005 | Steward et al. | |
| 2012/0195878 A1 | 8/2012 | Haag-molkenteller et al. | |
| 2015/0166972 A1 | 6/2015 | Dong et al. | |

FOREIGN PATENT DOCUMENTS

| | | |
|---|---|---|
| WO | 2009023549 A2 | 2/2009 |
| WO | 2009042165 A2 | 4/2009 |
| WO | 2011018665 A1 | 2/2011 |
| WO | 2017063743 A1 | 4/2017 |
| WO | 2018109447 A1 | 6/2018 |

OTHER PUBLICATIONS

Schneider et al, International Journal of Biochemistry & Cell Biology, 42:181-185, 2010.*
McNairn et al (BMC Dermatologu 13(2):1-11, 2013).*
STKE, 2003, Issue 210, Abstract only.*

* cited by examiner

*Primary Examiner* — Patricia Duffy
(74) *Attorney, Agent, or Firm* — Brigitte C. Phan

(57) ABSTRACT

A polypeptide having an amino acid sequence corresponding to a binding domain of a botulinum toxin is described. The polypeptide modulates expression of genes involved in, for example, collagen production and extra cellular matrix organization, and finds use, therefore in modulating skin quality attributes such as elasticity, firmness etc. Moreover, the polypeptide inhibits lipogenesis in specialized cells and finds use, therefore, in reducing skin oiliness, which is frequently observed in skin tissue afflicted with large pores and acne. Nucleic acids encoding the polypeptide, as well as vectors, host cells, and systems comprising the nucleic acids, are further described.

4 Claims, 9 Drawing Sheets

Specification includes a Sequence Listing.

SEQUENCE LISTING

<160> NUMBER OF SEQ ID NOS: 27

<210> SEQ ID NO 1
<211> LENGTH: 421
<212> TYPE: PRT
<213> ORGANISM: Clostridium botulinum

<400> SEQUENCE: 1

```
Thr Ser Ile Leu Asn Leu Arg Tyr Glu Ser Asn His Leu Ile Asp Leu
1               5                   10                  15

Ser Arg Tyr Ala Ser Lys Ile Asn Ile Gly Ser Lys Val Asn Phe Asp
                20                  25                  30

Pro Ile Asp Lys Asn Gln Ile Gln Leu Phe Asn Leu Glu Ser Ser Lys
            35                  40                  45

Ile Glu Val Ile Leu Lys Asn Ala Ile Val Tyr Asn Ser Met Tyr Glu
50                  55                  60

Asn Phe Ser Thr Ser Phe Trp Ile Arg Ile Pro Lys Tyr Phe Asn Ser
65                  70                  75                  80

Ile Ser Leu Asn Asn Glu Tyr Thr Ile Ile Asn Cys Met Glu Asn Asn
                85                  90                  95

Ser Gly Trp Lys Val Ser Leu Asn Tyr Gly Glu Ile Ile Trp Thr Leu
                100                 105                 110

Gln Asp Thr Gln Glu Ile Lys Gln Arg Val Val Phe Lys Tyr Ser Gln
            115                 120                 125

Met Ile Asn Ile Ser Asp Tyr Ile Asn Arg Trp Ile Phe Val Thr Ile
130                 135                 140

Thr Asn Asn Arg Leu Asn Asn Ser Lys Ile Tyr Ile Asn Gly Arg Leu
145                 150                 155                 160

Ile Asp Gln Lys Pro Ile Ser Asn Leu Gly Asn Ile His Ala Ser Asn
                165                 170                 175

Asn Ile Met Phe Lys Leu Asp Gly Cys Arg Asp Thr His Arg Tyr Ile
                180                 185                 190

Trp Ile Lys Tyr Phe Asn Leu Phe Asp Lys Glu Leu Asn Glu Lys Glu
            195                 200                 205

Ile Lys Asp Leu Tyr Asp Asn Gln Ser Asn Ser Gly Ile Leu Lys Asp
210                 215                 220

Phe Trp Gly Asp Tyr Leu Gln Tyr Asp Lys Pro Tyr Tyr Met Leu Asn
225                 230                 235                 240

Leu Tyr Asp Pro Asn Lys Tyr Val Asp Val Asn Asn Val Gly Ile Arg
                245                 250                 255

Gly Tyr Met Tyr Leu Lys Gly Pro Arg Gly Ser Val Met Thr Thr Asn
                260                 265                 270

Ile Tyr Leu Asn Ser Ser Leu Tyr Arg Gly Thr Lys Phe Ile Ile Lys
            275                 280                 285

Lys Tyr Ala Ser Gly Asn Lys Asp Asn Ile Val Arg Asn Asn Asp Arg
290                 295                 300

Val Tyr Ile Asn Val Val Lys Asn Lys Glu Tyr Arg Leu Ala Thr
305                 310                 315                 320

Asn Ala Ser Gln Ala Gly Val Glu Lys Ile Leu Ser Ala Leu Glu Ile
                325                 330                 335

Pro Asp Val Gly Asn Leu Ser Gln Val Val Met Lys Ser Lys Asn
            340                 345                 350

Asp Gln Gly Ile Thr Asn Lys Cys Lys Met Asn Leu Gln Asp Asn Asn
            355                 360                 365
```

Gly Asn Asp Ile Gly Phe Ile Gly Phe His Gln Phe Asn Asn Ile Ala
    370             375             380

Lys Leu Val Ala Ser Asn Trp Tyr Asn Arg Gln Ile Glu Arg Ser Ser
385             390             395             400

Arg Thr Leu Gly Cys Ser Trp Glu Phe Ile Pro Val Asp Asp Gly Trp
            405             410             415

Gly Glu Arg Pro Leu
        420

<210> SEQ ID NO 2
<211> LENGTH: 1266
<212> TYPE: DNA
<213> ORGANISM: Clostridium botulinum

<400> SEQUENCE: 2

| | |
|---|---|
| accagcattc tgaacctgcg ttatgaaagc aaccatctga ttgatctgag ccgttatgcg | 60 |
| agcaaaatta acattggcag caaagtgaac tttgatccga ttgataagaa ccagattcag | 120 |
| ctgtttaacc tggaaagcag caaaattgaa gtgattctga gaacgcgat tgtgtataac | 180 |
| agcatgtatg aaaactttag caccagcttt tggattcgta ttccgaaata ttttaacagc | 240 |
| attagcctga caacgaata taccattatt aactgcatgg aaaacaacag cggctggaaa | 300 |
| gtgagcctga actatggcga aattatttgg accctgcagg atacccagga aattaaacag | 360 |
| cgtgtggtgt ttaaatatag ccagatgatt aacattagcg attatattaa ccgttggatc | 420 |
| tttgtgacca ttaccaacaa ccgtctgaac aacagcaaaa tttatattaa cggccgtctg | 480 |
| attgatcaga aaccgattag caacctgggc aacattcatg cgagcaacaa cattatgttt | 540 |
| aaactggatg gctgccgtga tacccatcgt tatatttgga ttaaatattt taacctgttt | 600 |
| gataaagagc tcaacgagaa agaaattaaa gatctgtatg ataaccagag caacagcggc | 660 |
| attctgaaag atttctgggg cgattatctg cagtatgata accgtatta tgctgaac | 720 |
| ctgtatgatc cgaacaaata tgtggatgtg aacaacgtgg gcattcgtgg ctatatgtat | 780 |
| ctgaaaggcc cgcgtggcag cgtgatgacc accaacattt atctgaacag cagcctgtat | 840 |
| cgtggcacca aatttattat taagaagtat gcgagcggca caaagataa cattgtgcgt | 900 |
| aacaacgatc gtgtgtatat taacgtggtg gtgaagaaca agaatatcg tctggcgacc | 960 |
| aacgcgagcc aggcgggcgt ggaaaagatt ctgagcgcgc tggaaattcc ggatgtgggc | 1020 |
| aacctgagcc aggtggtggt gatgaaaagc aagaacgatc agggcattac caacaaatgc | 1080 |
| aaaatgaacc tgcaggataa caccggcaac gatattggct ttattggctt tcatcagttt | 1140 |
| aacaacattg cgaaactggt ggcgagcaac tggtataacc gtcagattga acgtagcagc | 1200 |
| cgtaccctgg gctgcagctg ggaatttatt ccggtggatg atggctgggg cgaacgtccg | 1260 |
| ctgtaa | 1266 |

<210> SEQ ID NO 3
<211> LENGTH: 429
<212> TYPE: PRT
<213> ORGANISM: Clostridium botulinum

<400> SEQUENCE: 3

Asn Ile Ile Leu Asn Leu Arg Tyr Lys Asp Asn Asn Leu Ile Asp Leu
1               5                   10                  15

Ser Gly Tyr Gly Ala Lys Val Glu Val Tyr Asp Gly Val Glu Leu Asn
            20                  25                  30

Asp Lys Asn Gln Phe Lys Leu Thr Ser Ser Ala Asn Ser Lys Ile Arg 35                  40                  45
Val Thr Gln Asn Gln Asn Ile Ile Phe Asn Ser Val Phe Leu Asp Phe
 50                  55                  60

Ser Val Ser Phe Trp Ile Arg Ile Pro Lys Tyr Lys Asn Asp Gly Ile
 65                  70                  75                  80

Gln Asn Tyr Ile His Asn Glu Tyr Thr Ile Asn Cys Met Lys Asn
                 85                  90                  95

Asn Ser Gly Trp Lys Ile Ser Ile Arg Gly Asn Arg Ile Ile Trp Thr
                100                 105                 110

Leu Ile Asp Ile Asn Gly Lys Thr Lys Ser Val Phe Phe Glu Tyr Asn
                115                 120                 125

Ile Arg Glu Asp Ile Ser Glu Tyr Ile Asn Arg Trp Phe Phe Val Thr
                130                 135                 140

Ile Thr Asn Asn Leu Asn Asn Ala Lys Ile Tyr Ile Asn Gly Lys Leu
145                 150                 155                 160

Glu Ser Asn Thr Asp Ile Lys Asp Ile Arg Glu Val Ile Ala Asn Gly
                165                 170                 175

Glu Ile Ile Phe Lys Leu Asp Gly Asp Ile Asp Arg Thr Gln Phe Ile
                180                 185                 190

Trp Met Lys Tyr Phe Ser Ile Phe Asn Thr Glu Leu Ser Gln Ser Asn
                195                 200                 205

Ile Glu Glu Arg Tyr Lys Ile Gln Ser Tyr Ser Glu Tyr Leu Lys Asp
                210                 215                 220

Phe Trp Gly Asn Pro Leu Met Tyr Asn Lys Glu Tyr Tyr Met Phe Asn
225                 230                 235                 240

Ala Gly Asn Lys Asn Ser Tyr Ile Lys Leu Lys Lys Asp Ser Pro Val
                245                 250                 255

Gly Glu Ile Leu Thr Arg Ser Lys Tyr Asn Gln Asn Ser Lys Tyr Ile
                260                 265                 270

Asn Tyr Arg Asp Leu Tyr Ile Gly Glu Lys Phe Ile Ile Arg Arg Lys
                275                 280                 285

Ser Asn Ser Gln Ser Ile Asn Asp Asp Ile Val Arg Lys Glu Asp Tyr
290                 295                 300

Ile Tyr Leu Asp Phe Phe Asn Leu Asn Gln Glu Trp Arg Val Tyr Thr
305                 310                 315                 320

Tyr Lys Tyr Phe Lys Lys Glu Glu Glu Lys Leu Phe Leu Ala Pro Ile
                325                 330                 335

Ser Asp Ser Asp Glu Phe Tyr Asn Thr Ile Gln Ile Lys Glu Tyr Asp
                340                 345                 350

Glu Gln Pro Thr Tyr Ser Cys Gln Leu Leu Phe Lys Lys Asp Glu Glu
                355                 360                 365

Ser Thr Asp Glu Ile Gly Leu Ile Gly Ile His Arg Phe Tyr Glu Ser
                370                 375                 380

Gly Ile Val Phe Glu Glu Tyr Lys Asp Tyr Phe Cys Ile Ser Lys Trp
385                 390                 395                 400

Tyr Leu Lys Glu Val Lys Arg Lys Pro Tyr Asn Leu Lys Leu Gly Cys
                405                 410                 415

Asn Trp Gln Phe Ile Pro Lys Asp Glu Gly Trp Thr Glu
                420                 425

<210> SEQ ID NO 4
<211> LENGTH: 421
<212> TYPE: PRT
<213> ORGANISM: Clostridium botulinum

<400> SEQUENCE: 4

```
Ser Lys Ile Leu Ser Leu Gln Asn Arg Lys Asn Thr Leu Val Asp Thr
 1               5                  10                  15
Ser Gly Tyr Asn Ala Glu Val Ser Glu Glu Gly Asp Val Gln Leu Asn
             20                  25                  30
Pro Ile Phe Pro Phe Asp Phe Lys Leu Gly Ser Ser Gly Glu Asp Arg
         35                  40                  45
Gly Lys Val Ile Val Thr Gln Asn Glu Asn Ile Val Tyr Asn Ser Met
 50                  55                  60
Tyr Glu Ser Phe Ser Ile Ser Phe Trp Ile Arg Ile Asn Lys Trp Val
 65                  70                  75                  80
Ser Asn Leu Pro Gly Tyr Thr Ile Ile Asp Ser Val Lys Asn Asn Ser
                 85                  90                  95
Gly Trp Ser Ile Gly Ile Ile Ser Asn Phe Leu Val Phe Thr Leu Lys
            100                 105                 110
Gln Asn Glu Asp Ser Glu Gln Ser Ile Asn Phe Ser Tyr Asp Ile Ser
            115                 120                 125
Asn Asn Ala Pro Gly Tyr Asn Lys Trp Phe Phe Val Thr Val Thr Asn
130                 135                 140
Asn Met Met Gly Asn Met Lys Ile Tyr Ile Asn Gly Lys Leu Ile Asp
145                 150                 155                 160
Thr Ile Lys Val Lys Glu Leu Thr Gly Ile Asn Phe Ser Lys Thr Ile
                165                 170                 175
Thr Phe Glu Ile Asn Lys Ile Pro Asp Thr Gly Leu Ile Thr Ser Asp
            180                 185                 190
Ser Asp Asn Ile Asn Met Trp Ile Arg Asp Phe Tyr Ile Phe Ala Lys
            195                 200                 205
Glu Leu Asp Gly Lys Asp Ile Asn Ile Leu Phe Asn Ser Leu Gln Tyr
            210                 215                 220
Thr Asn Val Val Lys Asp Tyr Trp Gly Asn Asp Leu Arg Tyr Asn Lys
225                 230                 235                 240
Glu Tyr Tyr Met Val Asn Ile Asp Tyr Leu Asn Arg Tyr Met Tyr Ala
                245                 250                 255
Asn Ser Arg Gln Ile Val Phe Asn Thr Arg Arg Asn Asn Asn Asp Phe
            260                 265                 270
Asn Glu Gly Tyr Lys Ile Ile Ile Lys Arg Ile Arg Gly Asn Thr Asn
            275                 280                 285
Asp Thr Arg Val Arg Gly Gly Asp Ile Leu Tyr Phe Asp Met Thr Ile
290                 295                 300
Asn Asn Lys Ala Tyr Asn Leu Phe Met Lys Asn Glu Thr Met Tyr Ala
305                 310                 315                 320
Asp Asn His Ser Thr Glu Asp Ile Tyr Ala Ile Gly Leu Arg Glu Gln
                325                 330                 335
Thr Lys Asp Ile Asn Asp Asn Ile Ile Phe Gln Ile Gln Pro Met Asn
            340                 345                 350
Asn Thr Tyr Tyr Tyr Ala Ser Gln Ile Phe Lys Ser Asn Phe Asn Gly
            355                 360                 365
Glu Asn Ile Ser Gly Ile Cys Ser Ile Gly Thr Tyr Arg Phe Arg Leu
            370                 375                 380
Gly Gly Asp Trp Tyr Arg His Asn Tyr Leu Val Pro Thr Val Lys Gln
385                 390                 395                 400
Gly Asn Tyr Ala Ser Leu Leu Glu Ser Thr Ser Thr His Trp Gly Phe
```

Val Pro Val Ser Glu
420

<210> SEQ ID NO 5
<211> LENGTH: 410
<212> TYPE: PRT
<213> ORGANISM: Clostridium botulinum

<400> SEQUENCE: 5

Ser Lys Ile Leu Ser Leu Gln Asn Lys Lys Asn Ala Leu Val Asp Thr
1               5                   10                  15

Ser Gly Tyr Asn Ala Glu Val Arg Val Gly Asp Asn Val Gln Leu Asn
            20                  25                  30

Thr Ile Tyr Thr Asn Asp Phe Lys Leu Ser Ser Ser Gly Asp Lys Ile
        35                  40                  45

Ile Val Asn Leu Asn Asn Asn Ile Leu Tyr Ser Ala Ile Tyr Glu Asn
50                  55                  60

Ser Ser Val Ser Phe Trp Ile Lys Ile Ser Lys Asp Leu Thr Asn Ser
65                  70                  75                  80

His Asn Glu Tyr Thr Ile Ile Asn Ser Ile Glu Gln Asn Ser Gly Trp
                85                  90                  95

Lys Leu Cys Ile Arg Asn Gly Asn Ile Glu Trp Ile Leu Gln Asp Val
            100                 105                 110

Asn Arg Lys Tyr Lys Ser Leu Ile Phe Asp Tyr Ser Glu Ser Leu Ser
        115                 120                 125

His Thr Gly Tyr Thr Asn Lys Trp Phe Phe Val Thr Ile Thr Asn Asn
130                 135                 140

Ile Met Gly Tyr Met Lys Leu Tyr Ile Asn Gly Glu Leu Lys Gln Ser
145                 150                 155                 160

Gln Lys Ile Glu Asp Leu Asp Glu Val Lys Leu Asp Lys Thr Ile Val
                165                 170                 175

Phe Gly Ile Asp Glu Asn Ile Asp Glu Asn Gln Met Leu Trp Ile Arg
            180                 185                 190

Asp Phe Asn Ile Phe Ser Lys Glu Leu Ser Asn Glu Asp Ile Asn Ile
        195                 200                 205

Val Tyr Glu Gly Gln Ile Leu Arg Asn Val Ile Lys Asp Tyr Trp Gly
210                 215                 220

Asn Pro Leu Lys Phe Asp Thr Glu Tyr Tyr Ile Ile Asn Asp Asn Tyr
225                 230                 235                 240

Ile Asp Arg Tyr Ile Ala Pro Glu Ser Asn Val Leu Val Leu Val Gln
                245                 250                 255

Tyr Pro Asp Arg Ser Lys Leu Tyr Thr Gly Asn Pro Ile Thr Ile Lys
            260                 265                 270

Ser Val Ser Asp Lys Asn Pro Tyr Ser Arg Ile Leu Asn Gly Asp Asn
        275                 280                 285

Ile Ile Leu His Met Leu Tyr Asn Ser Arg Lys Tyr Met Ile Ile Arg
290                 295                 300

Asp Thr Asp Thr Ile Tyr Ala Thr Gln Gly Gly Glu Cys Ser Gln Asn
305                 310                 315                 320

Cys Val Tyr Ala Leu Lys Leu Gln Ser Asn Leu Gly Asn Tyr Gly Ile
                325                 330                 335

Gly Ile Phe Ser Ile Lys Asn Ile Val Ser Lys Asn Lys Tyr Cys Ser
            340                 345                 350

-continued

```
Gln Ile Phe Ser Ser Phe Arg Glu Asn Thr Met Leu Leu Ala Asp Ile
            355                 360                 365

Tyr Lys Pro Trp Arg Phe Ser Phe Lys Asn Ala Tyr Thr Pro Val Ala
370                 375                 380

Val Thr Asn Tyr Glu Thr Lys Leu Leu Ser Thr Ser Ser Phe Trp Lys
385                 390                 395                 400

Phe Ile Ser Arg Asp Pro Gly Trp Val Glu
                405                 410

<210> SEQ ID NO 6
<211> LENGTH: 419
<212> TYPE: PRT
<213> ORGANISM: Clostridium botulinum

<400> SEQUENCE: 6

Ser Lys Ile Leu Ser Leu Gln Asn Lys Lys Asn Thr Leu Met Asp Thr
1               5                   10                  15

Ser Gly Tyr Asn Ala Glu Val Arg Val Glu Gly Asn Val Gln Leu Asn
            20                  25                  30

Pro Ile Phe Pro Phe Asp Phe Lys Leu Gly Ser Ser Gly Asp Asp Arg
        35                  40                  45

Gly Lys Val Ile Val Thr Gln Asn Glu Asn Ile Val Tyr Asn Ala Met
50                  55                  60

Tyr Glu Ser Phe Ser Ile Ser Phe Trp Ile Arg Ile Asn Lys Trp Val
65                  70                  75                  80

Ser Asn Leu Pro Gly Tyr Thr Ile Ile Asp Ser Val Lys Asn Asn Ser
                85                  90                  95

Gly Trp Ser Ile Gly Ile Ile Ser Asn Phe Leu Val Phe Thr Leu Lys
            100                 105                 110

Gln Asn Glu Asn Ser Glu Gln Asp Ile Asn Phe Ser Tyr Asp Ile Ser
        115                 120                 125

Lys Asn Ala Ala Gly Tyr Asn Lys Trp Phe Phe Val Thr Ile Thr Thr
130                 135                 140

Asn Met Met Gly Asn Met Met Ile Tyr Ile Asn Gly Lys Leu Ile Asp
145                 150                 155                 160

Thr Ile Lys Val Lys Glu Leu Thr Gly Ile Asn Phe Ser Lys Thr Ile
                165                 170                 175

Thr Phe Gln Met Asn Lys Ile Pro Asn Thr Gly Leu Ile Thr Ser Asp
            180                 185                 190

Ser Asp Asn Ile Asn Met Trp Ile Arg Asp Phe Tyr Ile Phe Ala Lys
        195                 200                 205

Glu Leu Asp Asp Lys Asp Ile Asn Ile Leu Phe Asn Ser Leu Gln Tyr
210                 215                 220

Thr Asn Val Val Lys Asp Tyr Trp Gly Asn Asp Leu Arg Tyr Asp Lys
225                 230                 235                 240

Glu Tyr Tyr Met Ile Asn Val Asn Tyr Met Asn Arg Tyr Met Ser Lys
                245                 250                 255

Lys Gly Asn Gly Ile Val Phe Asn Thr Arg Lys Asn Asn Asn Asp Phe
            260                 265                 270

Asn Glu Gly Tyr Lys Ile Ile Lys Arg Ile Arg Gly Asn Thr Asn
        275                 280                 285

Asp Thr Arg Val Arg Gly Glu Asn Val Leu Tyr Phe Asn Thr Thr Ile
290                 295                 300

Asp Asn Lys Gln Tyr Ser Leu Gly Met Tyr Lys Pro Ser Arg Asn Leu
305                 310                 315                 320
```

Gly Thr Asp Leu Val Pro Leu Gly Ala Leu Asp Gln Pro Met Asp Glu
                325                 330                 335

Ile Arg Lys Tyr Gly Ser Phe Ile Ile Gln Pro Cys Asn Thr Phe Asp
                340                 345                 350

Tyr Tyr Ala Ser Gln Leu Phe Leu Ser Ser Asn Ala Thr Thr Asn Arg
                355                 360                 365

Leu Gly Ile Leu Ser Ile Gly Ser Tyr Ser Phe Lys Leu Gly Asp Asp
                370                 375                 380

Tyr Trp Phe Asn His Glu Tyr Leu Ile Pro Val Ile Lys Ile Glu His
385                 390                 395                 400

Tyr Ala Ser Leu Leu Glu Ser Thr Ser Thr His Trp Val Phe Val Pro
                405                 410                 415

Ala Ser Glu

<210> SEQ ID NO 7
<211> LENGTH: 403
<212> TYPE: PRT
<213> ORGANISM: Clostridium botulinum

<400> SEQUENCE: 7

Ser Ser Val Leu Asn Met Arg Tyr Lys Asn Asp Lys Tyr Val Asp Thr
1               5                   10                  15

Ser Gly Tyr Asp Ser Asn Ile Asn Ile Asn Gly Asp Val Tyr Lys Tyr
                20                  25                  30

Pro Thr Asn Lys Asn Gln Phe Gly Ile Tyr Asn Asp Lys Leu Ser Glu
                35                  40                  45

Val Asn Ile Ser Gln Asn Asp Tyr Ile Ile Tyr Asp Asn Lys Tyr Lys
50                  55                  60

Asn Phe Ser Ile Ser Phe Trp Val Arg Ile Pro Asn Tyr Asp Asn Lys
65                  70                  75                  80

Ile Val Asn Val Asn Asn Glu Tyr Thr Ile Ile Asn Cys Met Arg Asp
                85                  90                  95

Asn Asn Ser Gly Trp Lys Val Ser Leu Asn His Asn Glu Ile Ile Trp
                100                 105                 110

Thr Leu Gln Asp Asn Ala Gly Ile Asn Gln Lys Leu Ala Phe Asn Tyr
                115                 120                 125

Gly Asn Ala Asn Gly Ile Ser Asp Tyr Ile Asn Lys Trp Ile Phe Val
                130                 135                 140

Thr Ile Thr Asn Asp Arg Leu Gly Asp Ser Lys Leu Tyr Ile Asn Gly
145                 150                 155                 160

Asn Leu Ile Asp Gln Lys Ser Ile Leu Asn Leu Gly Asn Ile His Val
                165                 170                 175

Ser Asp Asn Ile Leu Phe Lys Ile Val Asn Cys Ser Tyr Thr Arg Tyr
                180                 185                 190

Ile Gly Ile Arg Tyr Phe Asn Val Phe Asp Lys Glu Leu Asp Glu Thr
                195                 200                 205

Glu Ile Gln Thr Leu Tyr Ser Asn Glu Pro Asn Thr Asn Ile Leu Lys
                210                 215                 220

Asp Phe Trp Gly Asn Tyr Leu Leu Tyr Asp Lys Glu Tyr Tyr Leu Leu
225                 230                 235                 240

Asn Val Leu Lys Pro Asn Asn Phe Ile Asp Arg Arg Lys Asp Ser Thr
                245                 250                 255

Leu Ser Ile Asn Asn Ile Arg Ser Thr Ile Leu Leu Ala Asn Arg Leu
                260                 265                 270

```
Tyr Ser Gly Ile Lys Val Lys Ile Gln Arg Val Asn Ser Ser Thr
        275                 280                 285

Asn Asp Asn Leu Val Arg Lys Asn Asp Gln Val Tyr Ile Asn Phe Val
290                 295                 300

Ala Ser Lys Thr His Leu Phe Pro Leu Tyr Ala Asp Thr Ala Thr Thr
305                 310                 315                 320

Asn Lys Glu Lys Thr Ile Lys Ile Ser Ser Ser Gly Asn Arg Phe Asn
                325                 330                 335

Gln Val Val Met Asn Ser Val Gly Asn Asn Cys Thr Met Asn Phe
                340                 345                 350

Lys Asn Asn Gly Asn Asn Ile Gly Leu Leu Gly Phe Lys Ala Asp
                355                 360                 365

Thr Val Ala Ser Thr Trp Tyr Tyr Thr His Met Arg Asp His Thr
370                 375                 380

Asn Ser Asn Gly Cys Phe Trp Asn Phe Ile Ser Glu Glu His Gly Trp
385                 390                 395                 400

Gln Glu Lys

<210> SEQ ID NO 8
<211> LENGTH: 410
<212> TYPE: PRT
<213> ORGANISM: Clostridium botulinum

<400> SEQUENCE: 8

Asn Ser Ile Leu Asp Met Arg Tyr Glu Asn Asn Lys Phe Ile Asp Ile
1               5                   10                  15

Ser Gly Tyr Gly Ser Asn Ile Ser Ile Asn Gly Asp Val Tyr Ile Tyr
                20                  25                  30

Ser Thr Asn Arg Asn Gln Phe Gly Ile Tyr Ser Ser Lys Pro Ser Glu
            35                  40                  45

Val Asn Ile Ala Gln Asn Asn Asp Ile Ile Tyr Asn Gly Arg Tyr Gln
        50                  55                  60

Asn Phe Ser Ile Ser Phe Trp Val Arg Ile Pro Lys Tyr Phe Asn Lys
65                  70                  75                  80

Val Asn Leu Asn Asn Glu Tyr Thr Ile Ile Asp Cys Ile Arg Asn Asn
                85                  90                  95

Asn Ser Gly Trp Lys Ile Ser Leu Asn Tyr Asn Lys Ile Ile Trp Thr
                100                 105                 110

Leu Gln Asp Thr Ala Gly Asn Asn Gln Lys Leu Val Phe Asn Tyr Thr
            115                 120                 125

Gln Met Ile Ser Ile Ser Asp Tyr Ile Asn Lys Trp Ile Phe Val Thr
        130                 135                 140

Ile Thr Asn Asn Arg Leu Gly Asn Ser Arg Ile Tyr Ile Asn Gly Asn
145                 150                 155                 160

Leu Ile Asp Glu Lys Ser Ile Ser Asn Leu Gly Asp Ile His Val Ser
                165                 170                 175

Asp Asn Ile Leu Phe Lys Ile Val Gly Cys Asn Asp Thr Arg Tyr Val
                180                 185                 190

Gly Ile Arg Tyr Phe Lys Val Phe Asp Thr Glu Leu Gly Lys Thr Glu
            195                 200                 205

Ile Glu Thr Leu Tyr Ser Asp Glu Pro Asp Pro Ser Ile Leu Lys Asp
        210                 215                 220

Phe Trp Gly Asn Tyr Leu Leu Tyr Asn Lys Arg Tyr Tyr Leu Leu Asn
225                 230                 235                 240
```

```
Leu Leu Arg Thr Asp Lys Ser Ile Thr Gln Asn Ser Asn Phe Leu Asn
                245                 250                 255

Ile Asn Gln Gln Arg Gly Val Tyr Gln Lys Pro Asn Ile Phe Ser Asn
            260                 265                 270

Thr Arg Leu Tyr Thr Gly Val Glu Val Ile Ile Arg Lys Asn Gly Ser
        275                 280                 285

Thr Asp Ile Ser Asn Thr Asp Asn Phe Val Arg Lys Asn Asp Leu Ala
    290                 295                 300

Tyr Ile Asn Val Val Asp Arg Asp Val Glu Tyr Arg Leu Tyr Ala Asp
305                 310                 315                 320

Ile Ser Ile Ala Lys Pro Glu Lys Ile Ile Lys Leu Ile Arg Thr Ser
                325                 330                 335

Asn Ser Asn Asn Ser Leu Gly Gln Ile Ile Val Met Asp Ser Ile Gly
            340                 345                 350

Asn Asn Cys Thr Met Asn Phe Gln Asn Asn Asn Gly Gly Asn Ile Gly
        355                 360                 365

Leu Leu Gly Phe His Ser Asn Asn Leu Val Ala Ser Ser Trp Tyr Tyr
    370                 375                 380

Asn Asn Ile Arg Lys Asn Thr Ser Ser Asn Gly Cys Phe Trp Ser Phe
385                 390                 395                 400

Ile Ser Lys Glu His Gly Trp Gln Glu Asn
                405                 410

<210> SEQ ID NO 9
<211> LENGTH: 430
<212> TYPE: PRT
<213> ORGANISM: Clostridium botulinum

<400> SEQUENCE: 9

Asn Ala Ile Leu Ser Leu Ser Tyr Arg Gly Gly Arg Leu Ile Asp Ser
1               5                   10                  15

Ser Gly Tyr Gly Ala Thr Met Asn Val Gly Ser Asp Val Ile Phe Asn
            20                  25                  30

Asp Ile Gly Asn Gly Gln Phe Lys Leu Asn Asn Ser Glu Asn Ser Asn
        35                  40                  45

Ile Thr Ala His Gln Ser Lys Phe Val Val Tyr Asp Ser Met Phe Asp
    50                  55                  60

Asn Phe Ser Ile Asn Phe Trp Val Arg Thr Pro Lys Tyr Asn Asn Asn
65                  70                  75                  80

Asp Ile Gln Thr Tyr Leu Gln Asn Glu Tyr Thr Ile Ile Ser Cys Ile
                85                  90                  95

Lys Asn Asp Ser Gly Trp Lys Val Ser Ile Lys Gly Asn Arg Ile Ile
            100                 105                 110

Trp Thr Leu Ile Asp Val Asn Ala Lys Ser Lys Ser Ile Phe Phe Glu
        115                 120                 125

Tyr Ser Ile Lys Asp Asn Ile Ser Asp Tyr Ile Asn Lys Trp Phe Ser
    130                 135                 140

Ile Thr Ile Thr Asn Asp Arg Leu Gly Asn Ala Asn Ile Tyr Ile Asn
145                 150                 155                 160

Gly Ser Leu Lys Lys Ser Glu Lys Ile Leu Asn Leu Asp Arg Ile Asn
                165                 170                 175

Ser Ser Asn Asp Ile Asp Phe Lys Leu Ile Asn Cys Thr Asp Thr Thr
            180                 185                 190

Lys Phe Val Trp Ile Lys Asp Phe Asn Ile Phe Gly Arg Glu Leu Asn
```

```
            195                 200                 205
Ala Thr Glu Val Ser Ser Leu Tyr Trp Ile Gln Ser Ser Thr Asn Thr
210                 215                 220

Leu Lys Asp Phe Trp Gly Asn Pro Leu Arg Tyr Asp Thr Gln Tyr Tyr
225                 230                 235                 240

Leu Phe Asn Gln Gly Met Gln Asn Ile Tyr Ile Lys Tyr Phe Ser Lys
                245                 250                 255

Ala Ser Met Gly Glu Thr Ala Pro Arg Thr Asn Phe Asn Asn Ala Ala
                260                 265                 270

Ile Asn Tyr Gln Asn Leu Tyr Leu Gly Leu Arg Phe Ile Ile Lys Lys
                275                 280                 285

Ala Ser Asn Ser Arg Asn Ile Asn Asp Asn Ile Val Arg Glu Gly
290                 295                 300

Asp Tyr Ile Tyr Leu Asn Ile Asp Asn Ile Ser Asp Glu Ser Tyr Arg
305                 310                 315                 320

Val Tyr Val Leu Val Asn Ser Lys Glu Ile Gln Thr Gln Leu Phe Leu
                325                 330                 335

Ala Pro Ile Asn Asp Asp Pro Thr Phe Tyr Asp Val Leu Gln Ile Lys
                340                 345                 350

Lys Tyr Tyr Glu Lys Thr Thr Tyr Asn Cys Gln Ile Leu Cys Glu Lys
                355                 360                 365

Asp Thr Lys Thr Phe Gly Leu Phe Gly Ile Gly Lys Phe Val Lys Asp
                370                 375                 380

Tyr Gly Tyr Val Trp Asp Thr Tyr Asp Asn Tyr Phe Cys Ile Ser Gln
385                 390                 395                 400

Trp Tyr Leu Arg Arg Ile Ser Glu Asn Ile Asn Lys Leu Arg Leu Gly
                405                 410                 415

Cys Asn Trp Gln Phe Ile Pro Val Asp Glu Gly Trp Thr Glu
                420                 425                 430

<210> SEQ ID NO 10
<211> LENGTH: 410
<212> TYPE: PRT
<213> ORGANISM: Clostridium botulinum

<400> SEQUENCE: 10

Val Leu Asn Leu Gly Ala Glu Asp Gly Lys Ile Lys Asp Leu Ser Gly
1               5                   10                  15

Thr Thr Ser Asp Ile Asn Ile Gly Ser Asp Ile Glu Leu Ala Asp Gly
                20                  25                  30

Arg Glu Asn Lys Ala Ile Lys Ile Lys Gly Ser Glu Asn Ser Thr Ile
                35                  40                  45

Lys Ile Ala Met Asn Lys Tyr Leu Arg Phe Ser Ala Thr Asp Asn Phe
50                  55                  60

Ser Ile Ser Phe Trp Ile Lys His Pro Lys Pro Thr Asn Leu Leu Asn
65                  70                  75                  80

Asn Gly Ile Glu Tyr Thr Leu Val Glu Asn Phe Asn Gln Arg Gly Trp
                85                  90                  95

Lys Ile Ser Ile Gln Asp Ser Lys Leu Ile Trp Tyr Leu Arg Asp His
                100                 105                 110

Asn Asn Ser Ile Lys Ile Val Thr Pro Asp Tyr Ile Ala Phe Asn Gly
                115                 120                 125

Trp Asn Leu Ile Thr Ile Thr Asn Asn Arg Ser Lys Gly Ser Ile Val
                130                 135                 140
```

-continued

Tyr Val Asn Gly Ser Lys Ile Glu Glu Lys Asp Ile Ser Ser Ile Trp
145                 150                 155                 160

Asn Thr Glu Val Asp Asp Pro Ile Ile Phe Arg Leu Lys Asn Asn Arg
                165                 170                 175

Asp Thr Gln Ala Phe Thr Leu Leu Asp Gln Phe Ser Ile Tyr Arg Lys
            180                 185                 190

Glu Leu Asn Gln Asn Glu Val Val Lys Leu Tyr Asn Tyr Tyr Phe Asn
        195                 200                 205

Ser Asn Tyr Ile Arg Asp Ile Trp Gly Asn Pro Leu Gln Tyr Asn Lys
    210                 215                 220

Lys Tyr Tyr Leu Gln Thr Gln Asp Lys Pro Gly Lys Gly Leu Ile Arg
225                 230                 235                 240

Glu Tyr Trp Ser Ser Phe Gly Tyr Asp Tyr Val Ile Leu Ser Asp Ser
                245                 250                 255

Lys Thr Ile Thr Phe Pro Asn Asn Ile Arg Tyr Gly Ala Leu Tyr Asn
                260                 265                 270

Gly Ser Lys Val Leu Ile Lys Asn Ser Lys Leu Asp Gly Leu Val
            275                 280                 285

Arg Asn Lys Asp Phe Ile Gln Leu Glu Ile Asp Gly Tyr Asn Met Gly
290                 295                 300

Ile Ser Ala Asp Arg Phe Asn Glu Asp Thr Asn Tyr Ile Gly Thr Thr
305                 310                 315                 320

Tyr Gly Thr Thr His Asp Leu Thr Thr Asp Phe Glu Ile Ile Gln Arg
                325                 330                 335

Gln Glu Lys Tyr Arg Asn Tyr Cys Gln Leu Lys Thr Pro Tyr Asn Ile
            340                 345                 350

Phe His Lys Ser Gly Leu Met Ser Thr Glu Thr Ser Lys Pro Thr Phe
        355                 360                 365

His Asp Tyr Arg Asp Trp Val Tyr Ser Ser Ala Trp Tyr Phe Gln Asn
    370                 375                 380

Tyr Glu Asn Leu Asn Leu Arg Lys His Thr Lys Thr Asn Trp Tyr Phe
385                 390                 395                 400

Ile Pro Lys Asp Glu Gly Trp Asp Glu Asp
                405                 410

<210> SEQ ID NO 11
<211> LENGTH: 218
<212> TYPE: PRT
<213> ORGANISM: Clostridium botulinum

<400> SEQUENCE: 11

Thr Ser Ile Leu Asn Leu Arg Tyr Glu Ser Asn His Leu Ile Asp Leu
1               5                   10                  15

Ser Arg Tyr Ala Ser Lys Ile Asn Ile Gly Ser Lys Val Asn Phe Asp
            20                  25                  30

Pro Ile Asp Lys Asn Gln Ile Gln Leu Phe Asn Leu Glu Ser Ser Lys
        35                  40                  45

Ile Glu Val Ile Leu Lys Asn Ala Ile Val Tyr Asn Ser Met Tyr Glu
    50                  55                  60

Asn Phe Ser Thr Ser Phe Trp Ile Arg Ile Pro Lys Tyr Phe Asn Ser
65                  70                  75                  80

Ile Ser Leu Asn Asn Glu Tyr Thr Ile Ile Cys Met Glu Asn Asn
                85                  90                  95

Ser Gly Trp Lys Val Ser Leu Asn Tyr Gly Glu Ile Ile Trp Thr Leu
            100                 105                 110

```
Gln Asp Thr Gln Glu Ile Lys Gln Arg Val Val Phe Lys Tyr Ser Gln
            115                 120                 125

Met Ile Asn Ile Ser Asp Tyr Ile Asn Arg Trp Ile Phe Val Thr Ile
        130                 135                 140

Thr Asn Asn Arg Leu Asn Ser Lys Ile Tyr Ile Asn Gly Arg Leu
145                 150                 155                 160

Ile Asp Gln Lys Pro Ile Ser Asn Leu Gly Asn Ile His Ala Ser Asn
                165                 170                 175

Asn Ile Met Phe Lys Leu Asp Gly Cys Arg Asp Thr His Arg Tyr Ile
            180                 185                 190

Trp Ile Lys Tyr Phe Asn Leu Phe Asp Lys Glu Leu Asn Glu Lys Glu
        195                 200                 205

Ile Lys Asp Leu Tyr Asp Asn Gln Ser Asn
    210                 215
```

<210> SEQ ID NO 12
<211> LENGTH: 221
<212> TYPE: PRT
<213> ORGANISM: Clostridium botulinum

<400> SEQUENCE: 12

```
Asn Ile Ile Leu Asn Leu Arg Tyr Lys Asp Asn Asn Leu Ile Asp Leu
1               5                   10                  15

Ser Gly Tyr Gly Ala Lys Val Glu Val Tyr Asp Gly Val Glu Leu Asn
            20                  25                  30

Asp Lys Asn Gln Phe Lys Leu Thr Ser Ser Ala Asn Ser Lys Ile Arg
        35                  40                  45

Val Thr Gln Asn Gln Asn Ile Ile Phe Asn Ser Val Phe Leu Asp Phe
    50                  55                  60

Ser Val Ser Phe Trp Ile Arg Ile Pro Lys Tyr Lys Asn Asp Gly Ile
65                  70                  75                  80

Gln Asn Tyr Ile His Asn Glu Tyr Thr Ile Ile Asn Cys Met Lys Asn
            85                  90                  95

Asn Ser Gly Trp Lys Ile Ser Ile Arg Gly Asn Arg Ile Ile Trp Thr
        100                 105                 110

Leu Ile Asp Ile Asn Gly Lys Thr Lys Ser Val Phe Phe Glu Tyr Asn
    115                 120                 125

Ile Arg Glu Asp Ile Ser Glu Tyr Ile Asn Arg Trp Phe Phe Val Thr
130                 135                 140

Ile Thr Asn Asn Leu Asn Asn Ala Lys Ile Tyr Ile Asn Gly Lys Leu
145                 150                 155                 160

Glu Ser Asn Thr Asp Ile Lys Asp Ile Arg Glu Val Ile Ala Asn Gly
            165                 170                 175

Glu Ile Ile Phe Lys Leu Asp Gly Asp Ile Asp Arg Thr Gln Phe Ile
        180                 185                 190

Trp Met Lys Tyr Phe Ser Ile Phe Asn Thr Gln Leu Ser Gln Ser Asn
    195                 200                 205

Ile Glu Glu Arg Tyr Lys Ile Gln Ser Tyr Ser Glu Tyr
210                 215                 220
```

<210> SEQ ID NO 13
<211> LENGTH: 226
<212> TYPE: PRT
<213> ORGANISM: Clostridium botulinum

<400> SEQUENCE: 13

```
Ser Lys Ile Leu Ser Leu Gln Asn Arg Lys Asn Thr Leu Val Asp Thr
  1               5                  10                  15

Ser Gly Tyr Asn Ala Glu Val Ser Glu Gly Asp Val Gln Leu Asn
             20                  25                  30

Pro Ile Phe Pro Phe Asp Phe Lys Leu Gly Ser Ser Gly Glu Asp Arg
             35                  40                  45

Gly Lys Val Ile Val Thr Gln Asn Glu Asn Ile Val Tyr Asn Ser Met
 50                  55                  60

Tyr Glu Ser Phe Ser Ile Ser Phe Trp Ile Arg Ile Asn Lys Trp Val
 65                  70                  75                  80

Ser Asn Leu Pro Gly Tyr Thr Ile Ile Asp Ser Val Lys Asn Asn Ser
             85                  90                  95

Gly Trp Ser Ile Gly Ile Ile Ser Asn Phe Leu Val Phe Thr Leu Lys
            100                 105                 110

Gln Asn Glu Asp Ser Glu Gln Ser Ile Asn Phe Ser Tyr Asp Ile Ser
            115                 120                 125

Asn Asn Ala Pro Gly Tyr Asn Lys Trp Phe Phe Val Thr Val Thr Asn
130                 135                 140

Asn Met Met Gly Asn Met Lys Ile Tyr Ile Asn Gly Lys Leu Ile Asp
145                 150                 155                 160

Thr Ile Lys Val Lys Glu Leu Thr Gly Ile Asn Phe Ser Lys Thr Ile
                165                 170                 175

Thr Phe Glu Ile Asn Lys Ile Pro Asp Thr Gly Leu Ile Thr Ser Asp
                180                 185                 190

Ser Asp Asn Ile Asn Met Trp Ile Arg Asp Phe Tyr Ile Phe Ala Lys
                195                 200                 205

Glu Leu Asp Gly Lys Asp Ile Asn Ile Leu Phe Asn Ser Leu Gln Tyr
            210                 215                 220

Thr Asn
225

<210> SEQ ID NO 14
<211> LENGTH: 215
<212> TYPE: PRT
<213> ORGANISM: Clostridium botulinum

<400> SEQUENCE: 14

Ser Lys Ile Leu Ser Leu Gln Asn Lys Lys Asn Ala Leu Val Asp Thr
  1               5                  10                  15

Ser Gly Tyr Asn Ala Glu Val Arg Val Gly Asp Asn Val Gln Leu Asn
             20                  25                  30

Thr Ile Tyr Thr Asn Asp Phe Lys Leu Ser Ser Ser Gly Asp Lys Ile
             35                  40                  45

Ile Val Asn Leu Asn Asn Asn Ile Leu Tyr Ser Ala Ile Tyr Glu Asn
 50                  55                  60

Ser Ser Val Ser Phe Trp Ile Lys Ile Ser Lys Asp Leu Thr Asn Ser
 65                  70                  75                  80

His Asn Glu Tyr Thr Ile Ile Asn Ser Ile Glu Gln Asn Ser Gly Trp
             85                  90                  95

Lys Leu Cys Ile Arg Asn Gly Asn Ile Glu Trp Ile Leu Gln Asp Val
            100                 105                 110

Asn Arg Lys Tyr Lys Ser Leu Ile Phe Asp Tyr Ser Glu Ser Leu Ser
            115                 120                 125

His Thr Gly Tyr Thr Asn Lys Trp Phe Phe Val Thr Ile Thr Asn Asn
```

```
               130                 135                 140
Ile Met Gly Tyr Met Lys Leu Tyr Ile Asn Gly Glu Leu Lys Gln Ser
145                 150                 155                 160

Gln Lys Ile Glu Asp Leu Asp Glu Val Lys Leu Asp Lys Thr Ile Val
                165                 170                 175

Phe Gly Ile Asp Glu Asn Ile Asp Glu Asn Gln Met Leu Trp Ile Arg
                180                 185                 190

Asp Phe Asn Ile Phe Ser Lys Glu Leu Ser Asn Glu Asp Ile Asn Ile
                195                 200                 205

Val Tyr Glu Gly Gln Ile Leu
    210                 215
```

<210> SEQ ID NO 15
<211> LENGTH: 226
<212> TYPE: PRT
<213> ORGANISM: Clostridium botulinum

<400> SEQUENCE: 15

```
Ser Lys Ile Leu Ser Leu Gln Asn Lys Lys Asn Thr Leu Met Asp Thr
1               5                   10                  15

Ser Gly Tyr Asn Ala Glu Val Arg Val Glu Gly Asn Val Gln Leu Asn
                20                  25                  30

Pro Ile Phe Pro Phe Asp Phe Lys Leu Gly Ser Ser Gly Asp Asp Arg
                35                  40                  45

Gly Lys Val Ile Val Thr Gln Asn Glu Asn Ile Val Tyr Asn Ala Met
    50                  55                  60

Tyr Glu Ser Phe Ser Ile Ser Phe Trp Ile Arg Ile Asn Lys Trp Val
65                  70                  75                  80

Ser Asn Leu Pro Gly Tyr Thr Ile Ile Asp Ser Val Lys Asn Asn Ser
                85                  90                  95

Gly Trp Ser Ile Gly Ile Ile Ser Asn Phe Leu Val Phe Thr Leu Lys
                100                 105                 110

Gln Asn Glu Asn Ser Glu Gln Asp Ile Asn Phe Ser Tyr Asp Ile Ser
                115                 120                 125

Lys Asn Ala Ala Gly Tyr Asn Lys Trp Phe Phe Val Thr Ile Thr Thr
    130                 135                 140

Asn Met Met Gly Asn Met Met Ile Tyr Ile Asn Gly Lys Leu Ile Asp
145                 150                 155                 160

Thr Ile Lys Val Lys Glu Leu Thr Gly Ile Asn Phe Ser Lys Thr Ile
                165                 170                 175

Thr Phe Gln Met Asn Lys Ile Pro Asn Thr Gly Leu Ile Thr Ser Asp
                180                 185                 190

Ser Asp Asn Ile Asn Met Trp Ile Arg Asp Phe Tyr Ile Phe Ala Lys
                195                 200                 205

Glu Leu Asp Asp Lys Asp Ile Asn Ile Leu Phe Asn Ser Leu Gln Tyr
    210                 215                 220

Thr Asn
225
```

<210> SEQ ID NO 16
<211> LENGTH: 221
<212> TYPE: PRT
<213> ORGANISM: Clostridium botulinum

<400> SEQUENCE: 16

```
Ser Ser Val Leu Asn Met Arg Tyr Lys Asn Asp Lys Tyr Val Asp Thr
```

```
            1               5                  10                 15
Ser Gly Tyr Asp Ser Asn Ile Asn Ile Asn Gly Asp Val Tyr Lys Tyr
                20                 25                 30
Pro Thr Asn Lys Asn Gln Phe Gly Ile Tyr Asn Asp Lys Leu Ser Glu
                35                 40                 45
Val Asn Ile Ser Gln Asn Asp Tyr Ile Ile Tyr Asp Asn Lys Tyr Lys
            50                 55                 60
Asn Phe Ser Ile Ser Phe Trp Val Arg Ile Pro Asn Tyr Asp Asn Lys
65                 70                 75                 80
Ile Val Asn Val Asn Asn Glu Tyr Thr Ile Ile Asn Cys Met Arg Asp
                   85                 90                 95
Asn Asn Ser Gly Trp Lys Val Ser Leu Asn His Asn Glu Ile Ile Trp
                100                105                110
Thr Leu Gln Asp Asn Ala Gly Ile Asn Gln Lys Leu Ala Phe Asn Tyr
                115                120                125
Gly Asn Ala Asn Gly Ile Ser Asp Tyr Ile Asn Lys Trp Ile Phe Val
                130                135                140
Thr Ile Thr Asn Asp Arg Leu Gly Asp Ser Lys Leu Tyr Ile Asn Gly
145                150                155                160
Asn Leu Ile Asp Gln Lys Ser Ile Leu Asn Leu Gly Asn Ile His Val
                    165                170                175
Ser Asp Asn Ile Leu Phe Lys Ile Val Asn Cys Ser Tyr Thr Arg Tyr
                180                185                190
Ile Gly Ile Arg Tyr Phe Asn Val Phe Asp Lys Glu Leu Asp Glu Thr
                195                200                205
Glu Ile Gln Thr Leu Tyr Ser Asn Glu Pro Asn Thr Asn
                210                215                220
```

<210> SEQ ID NO 17
<211> LENGTH: 218
<212> TYPE: PRT
<213> ORGANISM: Clostridium botulinum

<400> SEQUENCE: 17

```
Asn Ser Ile Leu Asp Met Arg Tyr Glu Asn Asn Lys Phe Ile Asp Ile
1               5                  10                 15
Ser Gly Tyr Gly Ser Asn Ile Ser Ile Asn Gly Asp Val Tyr Ile Tyr
                20                 25                 30
Ser Thr Asn Arg Asn Gln Phe Gly Ile Tyr Ser Ser Lys Pro Ser Glu
                35                 40                 45
Val Asn Ile Ala Gln Asn Asn Asp Ile Ile Tyr Asn Gly Arg Tyr Gln
            50                 55                 60
Asn Phe Ser Ile Ser Phe Trp Val Arg Ile Pro Lys Tyr Phe Asn Lys
65                 70                 75                 80
Val Asn Leu Asn Asn Glu Tyr Thr Ile Ile Asp Cys Ile Arg Asn Asn
                   85                 90                 95
Asn Ser Gly Trp Lys Ile Ser Leu Asn Tyr Asn Lys Ile Ile Trp Thr
                100                105                110
Leu Gln Asp Thr Ala Gly Asn Asn Gln Lys Leu Val Phe Asn Tyr Thr
                115                120                125
Gln Met Ile Ser Ile Ser Asp Tyr Ile Asn Lys Trp Ile Phe Val Thr
                130                135                140
Ile Thr Asn Asn Arg Leu Gly Asn Ser Arg Ile Tyr Ile Asn Gly Asn
145                150                155                160
```

Leu Ile Asp Glu Lys Ser Ile Ser Asn Leu Gly Asp Ile His Val Ser
                165                 170                 175

Asp Asn Ile Leu Phe Lys Ile Val Gly Cys Asn Asp Thr Arg Tyr Val
            180                 185                 190

Gly Ile Arg Tyr Phe Lys Val Phe Asp Thr Glu Leu Gly Lys Thr Glu
        195                 200                 205

Ile Glu Thr Leu Tyr Ser Asp Glu Pro Asp
    210                 215

<210> SEQ ID NO 18
<211> LENGTH: 224
<212> TYPE: PRT
<213> ORGANISM: Clostridium botulinum

<400> SEQUENCE: 18

Asn Ala Ile Leu Ser Leu Ser Tyr Arg Gly Gly Arg Leu Ile Asp Ser
1               5                   10                  15

Ser Gly Tyr Gly Ala Thr Met Asn Val Gly Ser Asp Val Ile Phe Asn
            20                  25                  30

Asp Ile Gly Asn Gly Gln Phe Lys Leu Asn Asn Ser Glu Asn Ser Asn
        35                  40                  45

Ile Thr Ala His Gln Ser Lys Phe Val Val Tyr Asp Ser Met Phe Asp
    50                  55                  60

Asn Phe Ser Ile Asn Phe Trp Val Arg Thr Pro Lys Tyr Asn Asn Asn
65                  70                  75                  80

Asp Ile Gln Thr Tyr Leu Gln Asn Glu Tyr Thr Ile Ile Ser Cys Ile
                85                  90                  95

Lys Asn Asp Ser Gly Trp Lys Val Ser Ile Lys Gly Asn Arg Ile Ile
            100                 105                 110

Trp Thr Leu Ile Asp Val Asn Ala Lys Ser Lys Ser Ile Phe Phe Glu
        115                 120                 125

Tyr Ser Ile Lys Asp Asn Ile Ser Asp Tyr Ile Asn Lys Trp Phe Ser
    130                 135                 140

Ile Thr Ile Thr Asn Asp Arg Leu Gly Asn Ala Asn Ile Tyr Ile Asn
145                 150                 155                 160

Gly Ser Leu Lys Lys Ser Glu Lys Ile Leu Asn Leu Asp Arg Ile Asn
                165                 170                 175

Ser Ser Asn Asp Ile Asp Phe Lys Leu Ile Asn Cys Thr Asp Thr Thr
            180                 185                 190

Lys Phe Val Trp Ile Lys Asp Phe Asn Ile Phe Gly Arg Glu Leu Asn
        195                 200                 205

Ala Thr Glu Val Ser Ser Leu Tyr Trp Ile Gln Ser Ser Thr Asn Thr
    210                 215                 220

<210> SEQ ID NO 19
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Gly Ser Ser His His His His His His Ser Ser Gly Leu Val Pro
1               5                   10                  15

Arg Gly Ser His Met Asp Thr Ser Ile Leu Asn Leu Arg Tyr Glu Ser
            20                  25                  30

```
Asn His Leu Ile Asp Leu Ser Arg Tyr Ala Ser Lys Ile Asn Ile Gly
         35                  40                  45

Ser Lys Val Asn Phe Asp Pro Ile Asp Lys Asn Gln Ile Gln Leu Phe
 50                  55                  60

Asn Leu Glu Ser Ser Lys Ile Glu Val Ile Leu Lys Asn Ala Ile Val
 65                  70                  75                  80

Tyr Asn Ser Met Tyr Glu Asn Phe Ser Thr Ser Phe Trp Ile Arg Ile
                 85                  90                  95

Pro Lys Tyr Phe Asn Ser Ile Ser Leu Asn Asn Glu Tyr Thr Ile Ile
                100                 105                 110

Asn Cys Met Glu Asn Asn Ser Gly Trp Lys Val Ser Leu Asn Tyr Gly
            115                 120                 125

Glu Ile Ile Trp Thr Leu Gln Asp Thr Gln Glu Ile Lys Gln Arg Val
        130                 135                 140

Val Phe Lys Tyr Ser Gln Met Ile Asn Ile Ser Asp Tyr Ile Asn Arg
145                 150                 155                 160

Trp Ile Phe Val Thr Ile Thr Asn Asn Arg Leu Asn Asn Ser Lys Ile
                165                 170                 175

Tyr Ile Asn Gly Arg Leu Ile Asp Gln Lys Pro Ile Ser Asn Leu Gly
            180                 185                 190

Asn Ile His Ala Ser Asn Asn Ile Met Phe Lys Leu Asp Gly Cys Arg
        195                 200                 205

Asp Thr His Arg Tyr Ile Trp Ile Lys Tyr Phe Asn Leu Phe Asp Lys
        210                 215                 220

Glu Leu Asn Glu Lys Glu Ile Lys Asp Leu Tyr Asp Asn Gln Ser Asn
225                 230                 235                 240

Ser Gly Ile Leu Lys Asp Phe Trp Gly Asp Tyr Leu Gln Tyr Asp Lys
                245                 250                 255

Pro Tyr Tyr Met Leu Asn Leu Tyr Asp Pro Asn Lys Tyr Val Asp Val
                260                 265                 270

Asn Asn Val Gly Ile Arg Gly Tyr Met Tyr Leu Lys Gly Pro Arg Gly
            275                 280                 285

Ser Val Met Thr Thr Asn Ile Tyr Leu Asn Ser Ser Leu Tyr Arg Gly
        290                 295                 300

Thr Lys Phe Ile Ile Lys Lys Tyr Ala Ser Gly Asn Lys Asp Asn Ile
305                 310                 315                 320

Val Arg Asn Asn Asp Arg Val Tyr Ile Asn Val Val Lys Asn Lys
                325                 330                 335

Glu Tyr Arg Leu Ala Thr Asn Ala Ser Gln Ala Gly Val Glu Lys Ile
        340                 345                 350

Leu Ser Ala Leu Glu Ile Pro Asp Val Gly Asn Leu Ser Gln Val Val
        355                 360                 365

Val Met Lys Ser Lys Asn Asp Gln Gly Ile Thr Asn Lys Cys Lys Met
370                 375                 380

Asn Leu Gln Asp Asn Asn Gly Asn Asp Ile Gly Phe Ile Gly Phe His
385                 390                 395                 400

Gln Phe Asn Asn Ile Ala Lys Leu Val Ala Ser Asn Trp Tyr Asn Arg
                405                 410                 415

Gln Ile Glu Arg Ser Ser Arg Thr Leu Gly Cys Ser Trp Glu Phe Ile
            420                 425                 430

Pro Val Asp Asp Gly Trp Gly Glu Arg Pro Leu Gln
            435                 440
```

```
<210> SEQ ID NO 20
<211> LENGTH: 442
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Gly Ser Ser His His His His His His Ser Ser Gly Leu Val Pro
1               5                   10                  15

Arg Gly Ser His Met Asp Ser Lys Ile Leu Ser Leu Gln Asn Lys Lys
            20                  25                  30

Asn Thr Leu Met Asp Thr Ser Gly Tyr Asn Ala Glu Val Arg Val Glu
        35                  40                  45

Gly Asn Val Gln Leu Asn Pro Ile Phe Pro Phe Asp Phe Lys Leu Gly
    50                  55                  60

Ser Ser Gly Asp Asp Arg Gly Lys Val Ile Val Thr Gln Asn Glu Asn
65                  70                  75                  80

Ile Val Tyr Asn Ala Met Tyr Glu Ser Phe Ser Ile Ser Phe Trp Ile
                85                  90                  95

Arg Ile Asn Lys Trp Val Ser Asn Leu Pro Gly Tyr Thr Ile Ile Asp
            100                 105                 110

Ser Val Lys Asn Asn Ser Gly Trp Ser Ile Gly Ile Ile Ser Asn Phe
        115                 120                 125

Leu Val Phe Thr Leu Lys Gln Asn Glu Asn Ser Glu Gln Asp Ile Asn
    130                 135                 140

Phe Ser Tyr Asp Ile Ser Lys Asn Ala Ala Gly Tyr Asn Lys Trp Phe
145                 150                 155                 160

Phe Val Thr Ile Thr Thr Asn Met Met Gly Asn Met Met Ile Tyr Ile
                165                 170                 175

Asn Gly Lys Leu Ile Asp Thr Ile Lys Val Lys Glu Leu Thr Gly Ile
            180                 185                 190

Asn Phe Ser Lys Thr Ile Thr Phe Gln Met Asn Lys Ile Pro Asn Thr
        195                 200                 205

Gly Leu Ile Thr Ser Asp Ser Asp Asn Ile Asn Met Trp Ile Arg Asp
    210                 215                 220

Phe Tyr Ile Phe Ala Lys Glu Leu Asp Asp Lys Asp Ile Asn Ile Leu
225                 230                 235                 240

Phe Asn Ser Leu Gln Tyr Thr Asn Val Val Lys Asp Tyr Trp Gly Asn
                245                 250                 255

Asp Leu Arg Tyr Asp Lys Glu Tyr Tyr Met Ile Asn Val Asn Tyr Met
            260                 265                 270

Asn Arg Tyr Met Ser Lys Lys Gly Asn Gly Ile Val Phe Asn Thr Arg
        275                 280                 285

Lys Asn Asn Asn Asp Phe Asn Glu Gly Tyr Lys Ile Ile Ile Lys Arg
    290                 295                 300

Ile Arg Gly Asn Thr Asn Asp Thr Arg Val Arg Gly Glu Asn Val Leu
305                 310                 315                 320

Tyr Phe Asn Thr Thr Ile Asp Asn Lys Gln Tyr Ser Leu Gly Met Tyr
                325                 330                 335

Lys Pro Ser Arg Asn Leu Gly Thr Asp Leu Val Pro Leu Gly Ala Leu
            340                 345                 350

Asp Gln Pro Met Asp Glu Ile Arg Lys Tyr Gly Ser Phe Ile Ile Gln
        355                 360                 365
```

```
Pro Cys Asn Thr Phe Asp Tyr Tyr Ala Ser Gln Leu Phe Leu Ser Ser
    370                 375                 380

Asn Ala Thr Thr Asn Arg Leu Gly Ile Leu Ser Ile Gly Ser Tyr Ser
385                 390                 395                 400

Phe Lys Leu Gly Asp Asp Tyr Trp Phe Asn His Glu Tyr Leu Ile Pro
                405                 410                 415

Val Ile Lys Ile Glu His Tyr Ala Ser Leu Leu Glu Ser Thr Ser Thr
            420                 425                 430

His Trp Val Phe Val Pro Ala Ser Glu Gln
            435                 440
```

<210> SEQ ID NO 21
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Met Gly Ser Ser His His His His His His Ser Ser Gly Leu Val Pro
1               5                   10                  15

Arg Gly Ser His Met Asp Thr Ser Ile Leu Asn Leu Arg Tyr Glu Ser
                20                  25                  30

Asn His Leu Ile Asp Leu Ser Arg Tyr Ala Ser Lys Ile Asn Ile Gly
            35                  40                  45

Ser Lys Val Asn Phe Asp Pro Ile Asp Lys Asn Gln Ile Gln Leu Phe
50                  55                  60

Asn Leu Glu Ser Ser Lys Ile Glu Val Ile Leu Lys Asn Ala Ile Val
65                  70                  75                  80

Tyr Asn Ser Met Tyr Glu Asn Phe Ser Thr Ser Phe Trp Ile Arg Ile
                85                  90                  95

Pro Lys Tyr Phe Asn Ser Ile Ser Leu Asn Asn Glu Tyr Thr Ile Ile
                100                 105                 110

Asn Cys Met Glu Asn Asn Ser Gly Trp Lys Val Ser Leu Asn Tyr Gly
            115                 120                 125

Glu Ile Ile Trp Thr Leu Gln Asp Thr Gln Glu Ile Lys Gln Arg Val
130                 135                 140

Val Phe Lys Tyr Ser Gln Met Ile Asn Ile Ser Asp Tyr Ile Asn Arg
145                 150                 155                 160

Trp Ile Phe Val Thr Ile Thr Asn Asn Arg Leu Asn Asn Ser Lys Ile
                165                 170                 175

Tyr Ile Asn Gly Arg Leu Ile Asp Gln Lys Pro Ile Ser Asn Leu Gly
                180                 185                 190

Asn Ile His Ala Ser Asn Asn Ile Met Phe Lys Leu Asp Gly Cys Arg
            195                 200                 205

Asp Thr His Arg Tyr Ile Trp Ile Lys Tyr Phe Asn Leu Phe Asp Lys
            210                 215                 220

Glu Leu Asn Glu Lys Glu Ile Lys Asp Leu Tyr Asp Asn Gln Ser Asn
225                 230                 235                 240
```

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Gly Gly Gly Ser
1               5

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Glu Ala Ala Ala Lys
1               5

<210> SEQ ID NO 24
<211> LENGTH: 5
<212> TYPE: PRT
<213> ORGANISM: Clostridium botulinum

<400> SEQUENCE: 24

His Glu Leu Ile His
1               5

<210> SEQ ID NO 25
<211> LENGTH: 421
<212> TYPE: PRT
<213> ORGANISM: Clostridium botulinum

<400> SEQUENCE: 25

Thr Ser Ile Leu Asn Leu Arg Tyr Glu Ser Asn His Leu Ile Asp Leu
1               5                   10                  15

Ser Arg Tyr Ala Ser Lys Ile Asn Ile Gly Ser Lys Val Asn Phe Asp
            20                  25                  30

Pro Ile Asp Lys Asn Gln Ile Gln Leu Phe Asn Leu Glu Ser Ser Lys
        35                  40                  45

Ile Glu Val Ile Leu Lys Asn Ala Ile Val Tyr Asn Ser Met Tyr Glu
    50                  55                  60

Asn Phe Ser Thr Ser Phe Trp Ile Arg Ile Pro Lys Tyr Phe Asn Ser
65                  70                  75                  80

Ile Ser Leu Asn Asn Glu Tyr Thr Ile Ile Asn Cys Met Glu Asn Asn
                85                  90                  95

Ser Gly Trp Lys Val Ser Leu Asn Tyr Gly Glu Ile Ile Trp Thr Leu
            100                 105                 110

Gln Asp Thr Gln Glu Ile Lys Gln Arg Val Val Phe Lys Tyr Ser Gln
        115                 120                 125

Met Ile Asn Ile Ser Asp Tyr Ile Asn Arg Trp Ile Phe Val Thr Ile
    130                 135                 140

Thr Asn Asn Arg Leu Asn Asn Ser Lys Ile Tyr Ile Asn Gly Arg Leu
145                 150                 155                 160

Ile Asp Gln Lys Pro Ile Ser Asn Leu Gly Asn Ile His Ala Ser Asn
                165                 170                 175

Asn Ile Met Phe Lys Leu Asp Gly Cys Arg Asp Thr His Arg Tyr Ile
            180                 185                 190

Trp Ile Lys Tyr Phe Asn Leu Phe Asp Lys Glu Leu Asn Glu Lys Glu
        195                 200                 205

Ile Lys Asp Leu Tyr Asp Asn Gln Ser Asn Ser Gly Ile Leu Lys Asp

-continued

```
              210                 215                 220
Phe Trp Gly Asp Tyr Leu Gln Tyr Asp Lys Pro Tyr Tyr Met Leu Asn
225                 230                 235                 240

Leu Tyr Asp Pro Asn Lys Tyr Val Asp Val Asn Asn Val Gly Ile Arg
                245                 250                 255

Gly Tyr Met Tyr Leu Lys Gly Pro Arg Gly Ser Val Met Ala Ala Asn
                260                 265                 270

Ile Tyr Leu Asn Ser Ser Leu Tyr Arg Gly Thr Lys Phe Ile Ile Lys
                275                 280                 285

Lys Tyr Ala Ser Gly Asn Lys Asp Asn Ile Val Arg Asn Asn Asp Arg
            290                 295                 300

Val Tyr Ile Asn Val Val Lys Asn Lys Glu Tyr Arg Leu Ala Thr
305                 310                 315                 320

Asn Ala Ser Gln Ala Gly Val Glu Lys Ile Leu Ser Ala Leu Glu Ile
                325                 330                 335

Pro Asp Val Gly Asn Leu Ser Gln Val Val Met Lys Ser Lys Asn
                340                 345                 350

Asp Gln Gly Ile Thr Asn Lys Cys Lys Met Asn Leu Gln Asp Asn Asn
            355                 360                 365

Gly Asn Asp Ile Gly Phe Ile Gly Phe His Gln Phe Asn Asn Ile Ala
370                 375                 380

Lys Leu Val Ala Ser Asn Trp Tyr Asn Arg Gln Ile Glu Arg Ser Ser
385                 390                 395                 400

Arg Thr Leu Gly Cys Ser Trp Glu Phe Ile Pro Val Asp Asp Gly Trp
                405                 410                 415

Gly Glu Arg Pro Leu
                420

<210> SEQ ID NO 26
<211> LENGTH: 421
<212> TYPE: PRT
<213> ORGANISM: Clostridium botulinum

<400> SEQUENCE: 26

Thr Ser Ile Leu Asn Leu Arg Tyr Glu Ser Asn His Leu Ile Asp Leu
1               5                   10                  15

Ser Arg Tyr Ala Ser Lys Ile Asn Ile Gly Ser Lys Val Asn Phe Asp
                20                  25                  30

Pro Ile Asp Lys Asn Gln Ile Gln Leu Phe Asn Leu Glu Ser Ser Lys
            35                  40                  45

Ile Glu Val Ile Leu Lys Asn Ala Ile Val Tyr Asn Ser Met Tyr Glu
50                  55                  60

Asn Phe Ser Thr Ser Phe Trp Ile Arg Ile Pro Lys Tyr Phe Asn Ser
65                  70                  75                  80

Ile Ser Leu Asn Asn Glu Tyr Thr Ile Ile Asn Cys Met Glu Asn Asn
                85                  90                  95

Ser Gly Trp Lys Val Ser Leu Asn Tyr Gly Glu Ile Ile Trp Thr Leu
                100                 105                 110

Gln Asp Thr Gln Glu Ile Lys Gln Arg Val Val Phe Lys Tyr Ser Gln
            115                 120                 125

Met Ile Asn Ile Ser Asp Tyr Ile Asn Arg Trp Ile Phe Val Thr Ile
            130                 135                 140

Thr Asn Asn Arg Leu Asn Asn Ser Lys Ile Tyr Ile Asn Gly Arg Leu
145                 150                 155                 160
```

-continued

```
Ile Asp Gln Lys Pro Ile Ser Asn Leu Gly Asn Ile His Ala Ser Asn
            165                 170                 175

Asn Ile Met Phe Lys Leu Asp Gly Cys Arg Asp Thr His Arg Tyr Ile
        180                 185                 190

Trp Ile Lys Tyr Phe Asn Leu Phe Asp Lys Glu Leu Asn Glu Lys Glu
            195                 200                 205

Ile Lys Asp Leu Tyr Asp Asn Gln Ser Asn Ser Gly Ile Leu Lys Asp
        210                 215                 220

Phe Trp Gly Asp Tyr Leu Gln Tyr Asp Lys Pro Tyr Tyr Met Leu Asn
225                 230                 235                 240

Leu Tyr Asp Pro Asn Lys Tyr Val Asp Val Asn Asn Val Gly Ile Arg
                245                 250                 255

Gly Tyr Met Tyr Leu Lys Gly Pro Arg Gly Ser Val Met Thr Thr Asn
            260                 265                 270

Ile Tyr Leu Asn Ser Ser Leu Tyr Arg Gly Thr Lys Phe Ile Ile Lys
        275                 280                 285

Lys Tyr Ala Ser Gly Asn Lys Asp Asn Ile Val Arg Asn Asn Asp Arg
    290                 295                 300

Val Tyr Ile Asn Val Val Lys Asn Lys Glu Tyr Arg Leu Ala Thr
305                 310                 315                 320

Asn Ala Ser Gln Ala Gly Val Glu Lys Ile Leu Ser Ala Leu Glu Ile
                325                 330                 335

Pro Asp Val Gly Asn Leu Ser Gln Val Val Met Lys Ser Lys Asn
            340                 345                 350

Asp Gln Gly Ile Thr Asn Lys Cys Lys Met Asn Leu Gln Asp Asn Asn
        355                 360                 365

Gly Asn Asp Ile Gly Phe Ile Gly Phe His Gln Phe Asn Asn Ile Ala
    370                 375                 380

Lys Leu Val Ala Ser Asn Leu Ser Asn Arg Gln Ile Glu Arg Ser Ser
385                 390                 395                 400

Arg Thr Leu Gly Cys Ser Trp Glu Phe Ile Pro Val Asp Asp Gly Trp
                405                 410                 415

Gly Glu Arg Pro Leu
            420

<210> SEQ ID NO 27
<211> LENGTH: 421
<212> TYPE: PRT
<213> ORGANISM: Clostridium botulinum

<400> SEQUENCE: 27

Thr Ser Ile Leu Asn Leu Arg Tyr Glu Ser Asn His Leu Ile Asp Leu
1               5                   10                  15

Ser Arg Tyr Ala Ser Lys Ile Asn Ile Gly Ser Lys Val Asn Phe Asp
            20                  25                  30

Pro Ile Asp Lys Asn Gln Ile Gln Leu Phe Asn Leu Glu Ser Ser Lys
        35                  40                  45

Ile Glu Val Ile Leu Lys Asn Ala Ile Val Tyr Asn Ser Met Tyr Glu
    50                  55                  60

Asn Phe Ser Thr Ser Phe Trp Ile Arg Ile Pro Lys Tyr Phe Asn Ser
65                  70                  75                  80

Ile Ser Leu Asn Asn Glu Tyr Thr Ile Ile Asn Cys Met Glu Asn Asn
                85                  90                  95

Ser Gly Trp Lys Val Ser Leu Asn Tyr Gly Glu Ile Ile Trp Thr Leu
            100                 105                 110
```

-continued

```
Gln Asp Thr Gln Glu Ile Lys Gln Arg Val Val Phe Lys Tyr Ser Gln
        115                 120                 125

Met Ile Asn Ile Ser Asp Tyr Ile Asn Arg Trp Ile Phe Val Thr Ile
    130                 135                 140

Thr Asn Asn Arg Leu Asn Asn Ser Lys Ile Tyr Ile Asn Gly Arg Leu
145                 150                 155                 160

Ile Asp Gln Lys Pro Ile Ser Asn Leu Gly Asn Ile His Ala Ser Asn
                165                 170                 175

Asn Ile Met Phe Lys Leu Asp Gly Cys Arg Asp Thr His Arg Tyr Ile
            180                 185                 190

Trp Ile Lys Tyr Phe Asn Leu Phe Asp Lys Glu Leu Asn Glu Lys Glu
        195                 200                 205

Ile Lys Asp Leu Tyr Asp Asn Gln Ser Asn Ser Gly Ile Leu Lys Asp
    210                 215                 220

Phe Trp Gly Asp Tyr Leu Gln Tyr Asp Lys Pro Tyr Tyr Met Leu Asn
225                 230                 235                 240

Leu Tyr Asp Pro Asn Lys Tyr Val Asp Val Asn Asn Val Gly Ile Arg
                245                 250                 255

Gly Tyr Met Tyr Leu Lys Gly Pro Arg Gly Ser Val Met Thr Thr Asn
            260                 265                 270

Ile Tyr Leu Asn Ser Ser Leu Tyr Arg Gly Thr Lys Phe Ile Ile Lys
        275                 280                 285

Lys Tyr Ala Ser Gly Asn Lys Asp Asn Ile Val Arg Asn Asn Asp Arg
    290                 295                 300

Val Tyr Ile Asn Val Val Lys Asn Lys Glu Tyr Arg Leu Ala Thr
305                 310                 315                 320

Asn Ala Ser Gln Ala Gly Val Glu Lys Ile Leu Ser Ala Leu Glu Ile
                325                 330                 335

Pro Asp Val Gly Asn Leu Ser Gln Val Val Val Met Lys Ser Lys Asn
            340                 345                 350

Asp Gln Gly Ile Thr Asn Lys Cys Lys Met Asn Leu Gln Asp Asn Asn
        355                 360                 365

Gly Asn Asp Ile Gly Phe Ile Gly Phe His Gln Phe Asn Asn Ile Ala
    370                 375                 380

Lys Leu Val Ala Ser Asn Trp Tyr Asn Arg Gln Ile Glu Arg Ser Ser
385                 390                 395                 400

Arg Thr Leu Gly Cys Ser Trp Glu Phe Ile Pro Val Asp Asp Gly Trp
                405                 410                 415

Arg Glu Arg Pro Leu
            420
```

BOTULINUM TOXIN CELL BINDING DOMAIN POLYPEPTIDES AND METHODS OF USE FOR SKIN REJUVENATION

CROSS-REFERENCE TO RELATED APPLICATIONS

This application claims the benefit of U.S. Provisional No. 62/608,119, filed on Dec. 20, 2017 and U.S. Provisional No. 62/727,640, filed on Sep. 6, 2018, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Dec. 17, 2018, is named 19980-US-NTB_SL19980PROV2(NTB)_SL.txt and is 71,994 bytes in size.

TECHNICAL FIELD

The present disclosure relates generally to polypeptides from the cell binding domain of Botulinum toxin and use of the polypeptides for cosmetic applications related to skin rejuvenation.

BACKGROUND

The anaerobic, gram positive bacterium *Clostridium botulinum* produces a potent polypeptide neurotoxin, botulinum toxin (BoNT), which has well-documented medical applications. Naturally-occurring Clostridial toxins are each translated as a single-chain polypeptide of approximately 150 kilo Daltons (kDa) of an approximately 50 kDa light chain (LC), comprising an enzymatic domain, and an approximately 100 kDa heavy chain, comprising an N-terminal translocation domain ($H_N$) and a C-terminal receptor-binding domain ($H_C$). Thus, full length Clostridial toxin molecules comprise three functionally distinct domains: (1) an enzymatic domain located in the LC that includes a metalloprotease region containing a zinc-dependent endopeptidase, which specifically targets core components of the neurotransmitter release apparatus; (2) a translocation domain contained within the amino-terminal half of the heavy chain ($H_N$) that facilitates release of the LC from intracellular vesicles into the cytoplasm of the target cell; and (3) a binding domain found within the carboxyl-terminal half of the heavy chain ($H_C$) that determines the binding affinity and specificity of the toxin to receptors located at the surface of the target cell. The binding domain comprises two distinct structural features of roughly equal size designated the N-terminal subdomain ($H_{CN}$) and the C-terminal subdomain ($H_{CC}$).

This toxin architecture is present in various immunologically-distinct botulinum neurotoxins, e.g., botulinum neurotoxin serotypes A, B, $C_1$, D, DC, E, F, G, X and J. Regardless of serotype, there exists a remarkable degree of structural and functional homology between the full length 150 kDa toxin proteins as well as the individual domains therein. In this regard, the BoNTs possess approximately 35% amino acid identity with each other and share the same functional domain organization and overall structural architecture. Within each type of Clostridial toxin there are also subtypes that differ somewhat in their amino acid sequence; however, the domain architecture of the various domains, e.g., endopeptidase, translocation, and the cell-binding domains, are also conserved within the individual subtypes. For example, there are presently five BoNT/A subtypes, BoNT/A1, BoNT/A2, BoNT/A3 BoNT/A4 and BoNT/A5; which share approximately 89% overall amino acid identity. Other members of the superfamily, e.g., tetanus toxin (TeNT) produced by a uniform group of *C. tetani* and other related toxins produced by Clostridia species, e.g., BaNT (produced by *C. baratii*) and BuNT (produced by and *C. butyricum*) are also structurally similar to the aforementioned Clostridial toxins, e.g., BoNT/F and BoNT/E, for instance, with respect to amino acid sequence identity.

Existing pharmaceutical formulations contain the full-length Clostridial toxin. There is a need for Clostridial toxin fragments and variants which have biological activities that are comparable to, if not better than, full length, while offering an improved therapeutic profile, e.g., improved safety, enhanced stability and/or better in vivo efficacy, compared to the whole Clostridial toxin.

SUMMARY

Described herein are various cosmetic applications of BoNT polypeptides of the present disclosure. For instance, treatment of primary human dermal fibroblasts with a polypeptide containing the binding domain of BoNT/A ($H_C/A$), fragments, or variants thereof modulated the expression of a number of genes. Specifically, treatment with the polypeptides of the present disclosure resulted in initial increased expression of genes encoding matrix degrading enzymes like matrix metalloproteinases (MMPs) and proteins like TP63 (Transformation-related protein 63, a transcription factor identifying corneal and epidermal stem cells), followed by increased expression of genes encoding major matrix structure proteins like collagen and elastin, which indicate extracellular matrix (ECM) remodeling. Treatment of normal human primary fibroblast cells with the polypeptide of the disclosure, e.g., BoNT/A ($H_C/A$), increased expression of genes known to be involved with tissue and ECM homeostasis, re-modeling, renewal, and repair.

Additional studies conducted with fragments of the polypeptides of the disclosure, e.g., the N-terminal half of the binding domain of BoNT, also resulted in similar cellular effects on normal human primary fibroblast cells. Specifically, binding domain of BoNT/A ($H_C/A$) and the N-terminal half of the binding domain ($H_{CN}/A$), respectively, were equally effective in affecting expression of fibroblast-related genes; FGFR1, MMP1, MMP3, TIMP1, FGF7, TP63, SOD2, UBD, HAS2, HAS3, ADAMTS1, IGF-1, IL-6, IL-32, CCL2, and BDKRB1. These data point to the potential modulation of the structural and functional properties of skin dermis in human patients by the polypeptides of the disclosure.

Further studies on fibroblast cells showed that the polypeptides of the disclosure modulated fibronectin expression. Since fibronectin is associated with mediating changes in ECM structure and/or biomechanical properties of the skin, the data point to the potential effect of the polypeptides of the disclosure on changing physical and/or mechanical attributes of the skin.

Parallel studies with BoNT/DC ($H_C/DC$) on primary fibroblast cells showed similar results with respect to modulation of gene expression. For example, $H_C/DC$ treatment modulated the expression of a number of genes in primary fibroblasts. $H_C/DC$ was found to be more effective in modulating some genes expression relative to $H_{CN}/A$. These findings suggest that other additional BoNT serotypes could affect properties or attributes of skin in a manner that is analogous to BoNT/A (H$_C$/A) and BoNT/DC (H$_C$/DC).

Functional studies on sebocyte cells revealed that the polypeptides of the disclosure significantly inhibited oleic acid-induced lipogenesis in sebocyte cells. Since sebocyte lipogenesis is associated with cosmetic properties of the skin, these data point to the potential application of the polypeptides of the disclosure in modulating skin properties or attributes.

The present disclosure accordingly relates to the following non-limiting aspects:

In one aspect, polypeptides and polynucleotide sequences, and compositions comprising such polypeptides or polynucleotides, which comprise a binding domain sequence of a Clostridial toxin, such as botulinum toxin, are described. In one embodiment, polypeptide sequences are described that participate in cellular signaling and/or that modulate cellular gene expression to achieve an increased expression of extracellular matrix proteins such as for example fibronectin, elastin and/or collagen, and a corresponding change in cellular phenotype. In some embodiments, polypeptide sequences are described which significantly reduce lipogenesis in target cells, e.g., sebocyte cells.

In another aspect, there is provided a polypeptide comprising an amino acid sequence substantially identical to an amino acid sequence in a binding domain of a botulinum toxin. In some embodiments, the polypeptide has a molecular weight between about 1 kDa to about 90 kDa. In one embodiment, the molecular weight of the polypeptide is between about 4 kDa to about 60 kD. In one embodiment, the molecular weight of the polypeptide is between about 12 kDa to about 50 kD.

In another aspect, a polypeptide comprises a sequence of amino acids having at least 90% sequence identity to a binding domain of a botulinum toxin is provided. In some embodiments, the polypeptide has a molecular weight of the polypeptide is between about 1 kDa to about 90 kDa. In one embodiment, the molecular weight of the polypeptide is between about 4 kDa to about 60 kD. In one embodiment, the molecular weight of the polypeptide is between about 12 kDa to about 50 kD.

In some embodiments, the polypeptide comprises an amino acid sequence substantially identical to an amino acid sequence in the full-length of a botulinum toxin which is devoid of toxicity. In one embodiment, the polypeptide comprises an amino acid sequence substantially identical to the amino acid sequence of the full-length of a botulinum toxin which is devoid of toxicity. In some embodiments, the polypeptide comprises an amino acid sequence substantially identical to an amino acid sequence in the heavy chain of the botulinum toxin. In some embodiments, the polypeptide comprises an amino acid sequence substantially identical to an amino acid sequence in the carboxyl or C-terminal segment of the heavy chain of botulinum toxin (H$_C$). In one embodiment, the polypeptide comprises an amino acid sequence substantially identical to an amino acid sequence of the binding domain of the botulinum toxin. In one embodiment, the polypeptide comprises an amino acid sequence identical to the amino acid sequence of the binding domain of the botulinum toxin. In another embodiment, the polypeptide comprises an amino acid sequence substantially identical to an amino acid sequence in the amino or N-terminal half of the binding domain of the botulinum toxin (H$_{CN}$). In one embodiment, the polypeptide comprises an amino acid sequence identical to the N-terminal half of the binding domain of the botulinum toxin.

In one embodiment, the botulinum toxin is selected from the group consisting of Botulinum toxin serotype A (BoNT/A), Botulinum toxin serotype B (BoNT/B), Botulinum toxin serotype C$_1$ (BoNT/C$_1$), Botulinum toxin serotype D (BoNT/D), Botulinum toxin serotype E (BoNT/E), Botulinum toxin serotype F (BoNT/F), Botulinum toxin serotype G (BoNT/G), Botulinum toxin serotype H (BoNT/H), Botulinum toxin serotype X (BoNT/X), *Enterococcus* sp. BoNT/J (eBoNT/J), and mosaic Botulinum toxins and/or variants thereof. Examples of mosaic toxins include BoNT/DC, BoNT/CD, and BoNT/FA. In one embodiment, the botulinum toxin is not Botulinum toxin serotype A (BoNT/A).

In still another embodiment, the polypeptide is capable of modulating expression of fibroblast related genes. In some embodiments, the polypeptide is capable of modulating genes selected from FGFR1 (Fibroblast growth factor receptor 1), MMP1, MMP3 (Matrix metalloproteinases), TIMP1 (TIMP metallopeptidase inhibitor 1), FGF7 (Fibroblast growth factor 7), and TP63 (Tumor protein p63).

In other embodiments, the polypeptide is capable of modulating expression of a genetic signature comprising genes selected from FGFR1, MMP1, MMP3, TIMP1, FGF7, TP63, SOD2 (Superoxide dismutase 2, mitochondrial), UBD (Ubiquitin D), HAS2, HAS3 (Hyaluronan synthase), ADAMTS1 (A disintegrin and metalloproteinase with thrombospondin motifs 1), IGF-1 (Insulin-like growth factor 1), IL-6, IL-32 (Interleukin), CCL2 (C chemokine (C-C motif) ligand 2), and BDKRB1 (Bradykinin receptor B1).

In other embodiments, the polypeptide is capable of modulating expression of a genetic signature comprising genes selected from MC5R, AR, HSD3B1, HSD17B1 and PPARδ. In one embodiment, the polypeptide is capable of modulating induced expression of at least one gene selected from MC5R, AR, HSD3B1, HSD17B1 and PPARδ in sebocyte cells.

In other embodiments, the polypeptide is capable of elevating fibronectin expression or synthesis in a target cell. In some embodiments, the target cell comprises a fibroblast, a keratinocyte, a melanocyte, a sebocyte, an adipocyte, a neuron, or combinations thereof.

In another embodiment, the polypeptide is capable of changing a morphological or a functional feature of a target cell.

In another embodiment, the polypeptide is capable of changing a morphological feature of a target fibroblast cell.

In another embodiment, the polypeptide lacks botulinum toxin endopeptidase activity.

In still another embodiment, the polypeptide lacks botulinum toxin translocation activity. In one embodiment, the polypeptide lacks an amino acid sequence which is substantially identical to the amino acid sequence in the amino terminus of the heavy chain (H$_N$) of the botulinum toxin. In still another embodiment, the polypeptide consists of an amino acid sequence substantially identical to an amino acid sequence in a binding domain of a botulinum toxin.

In still another embodiment, the polypeptide comprises an amino acid sequence having at least 30%, at least 40%, at least 50%, at least 60%, at least 70%, at least 80%, at least 90% homology to a sequence selected from the group consisting of SEQ ID NO: 1, SEQ ID NO: 19, SEQ ID NOs: 3-5, SEQ ID NO: 6, SEQ ID NO: 20, SEQ ID Nos: 7-10, SEQ ID NO: 11, SEQ ID NO: 21, and SEQ ID NOs: 12-18.

In yet another embodiment, the polypeptide has at least about 90% sequence identity to a sequence selected from the group consisting of SEQ ID NO: 1, SEQ ID NO: 19, SEQ ID NOs: 3-5, SEQ ID NO: 6, SEQ ID NO: 20, SEQ ID Nos: 7-10, SEQ ID NO: 11, SEQ ID NO: 21, and SEQ ID NOs: 12-18.

In yet another embodiment, the polypeptide consists essentially of the polypeptide sequence set forth in SEQ ID NO: 1, SEQ ID NO: 19, SEQ ID NOs: 3-5, SEQ ID NO: 6, SEQ ID NO: 20, SEQ ID Nos: 7-10, SEQ ID NO: 11, SEQ ID NO: 21, and SEQ ID NOs: 12-18.

In some embodiments, the polypeptide comprises, consists essentially of, or consists of the polypeptide sequence set forth in SEQ ID NO: 1, SEQ ID NO: 19, SEQ ID NOs: 3-5, SEQ ID NO: 6, SEQ ID NO: 20, SEQ ID Nos: 7-10, SEQ ID NO: 11, SEQ ID NO: 21, and SEQ ID NOs: 12-18, with the proviso that the polypeptide contains 1, 2, 3, 4, or 5 mutations in the polypeptide sequence. Preferably, the mutant polypeptide contains 1, 2, 3, 4, or 5 mutations in the polypeptide sequence of SEQ ID NO: 1, e.g., a mutant polypeptide comprising, consisting essentially of, or consisting of the polypeptide sequence set forth in SEQ ID NO: 25, SEQ ID NO: 26 or SEQ ID NO: 27.

In another aspect, a fusion protein comprising the polypeptide described herein is provided.

In another aspect, a pharmaceutical composition is provided that comprises a polypeptide or a fusion protein as described herein and a pharmaceutically acceptable carrier.

In one embodiment, the pharmaceutical composition is formulated for topical or transdermal administration.

In yet another aspect, a kit is described that comprises the polypeptide or a fusion protein as described herein. In some embodiments, the kit further comprises and instructions for administration. In some embodiments, the kit comprises one or more packages.

In yet another aspect, a method for modulating a skin quality attribute in a subject is provided. In some embodiments, the method comprises administering to the subject a composition comprising a polypeptide having an amino acid sequence with at least about 90% sequence identity to an amino acid sequence in the full length of a botulinum toxin. In some embodiments, the method comprises administering to the subject a composition comprising a polypeptide having an amino acid sequence with at least about 90% sequence identity to an amino acid sequence in the binding domain of a botulinum toxin. In another embodiment, the method comprises administering to the subject a composition comprising a polypeptide having an amino acid sequence with at least about 90% sequence identity to an amino acid sequence in the amino or N-terminal half of the binding domain of the botulinum toxin ($H_{CN}$). In some embodiments, the polypeptide has a molecular weight between about 20 kDa to about 60 kDa. In one embodiment, modulating a skin quality attribute does not involve paralysis of a facial muscle. In some embodiments, the botulinum toxin is selected from the group consisting of Botulinum toxin serotype A (BoNT/A), Botulinum toxin serotype B (BoNT/B), Botulinum toxin serotype $C_1$ (BoNT/$C_1$), Botulinum toxin serotype D (BoNT/D), Botulinum toxin serotype E (BoNT/E), Botulinum toxin serotype F (BoNT/F), Botulinum toxin serotype G (BoNT/G), Botulinum toxin serotype H (BoNT/H), Botulinum toxin serotype X (BoNT/X), *Enterococcus* sp. BoNT/J (eBoNT/J), and mosaic Botulinum toxins and/or variants thereof. Examples of mosaic toxins include BoNT/DC, BoNT/CD, and BoNT/FA. In one embodiment, the botulinum toxin is not Botulinum toxin serotype A (BoNT/A).

In one embodiment, the skin quality attribute is selected from the group consisting of clarity, hydration, epidermal and dermal thickness, texture, elasticity, color, tone, pliability, firmness, tightness, smoothness, thickness, radiance, evenness, laxity, complexion, fine lines, wrinkles, pore size, and oiliness. In another embodiment, the modulation produces at least about 20% improvement in the attribute.

In still another aspect, a method for stimulating collagen production in a subject is provided. In some embodiments, the method comprises administering to the subject a composition comprising a polypeptide having an amino acid sequence with at least about 90% sequence identity to an amino acid sequence in the full length of a botulinum toxin. In some embodiments, the method comprises administering to the subject a composition comprising a polypeptide having an amino acid sequence with at least about 90% sequence identity to an amino acid sequence in the binding domain of a botulinum toxin. In another embodiment, the method comprises administering to the subject a composition comprising a polypeptide having an amino acid sequence with at least about 90% sequence identity to an amino acid sequence in the amino or N-terminal half of the binding domain of the botulinum toxin ($H_{CN}$). In some embodiments, the method comprises administering to the subject a composition comprising a polypeptide having an amino acid sequence with at least about 90% sequence identity to a binding domain of a botulinum toxin. In some embodiments, the polypeptide has a molecular weight between about 20 kDa to about 60 kDa. In one embodiment, stimulating collagen production does not involve paralysis of a facial muscle.

In still another aspect, a method for treating skin disorders associated with sebum dysregulation and/or abnormalities in a subject is provided. In some embodiments, the method comprises administering to the subject a composition comprising a polypeptide having an amino acid sequence with at least about 90% sequence identity to an amino acid sequence in the full length of a botulinum toxin. In some embodiments, the method comprises administering to the subject a composition comprising a polypeptide having an amino acid sequence with at least about 90% sequence identity to an amino acid sequence in the binding domain of a botulinum toxin. In another embodiment, the method comprises administering to the subject a composition comprising a polypeptide having an amino acid sequence with at least about 90% sequence identity to an amino acid sequence in the amino or N-terminal half of the binding domain of the botulinum toxin ($H_{CN}$). In some embodiments, the method comprises administering to the subject a composition comprising a polypeptide having an amino acid sequence with at least about 90% sequence identity to a binding domain of a botulinum toxin. In some embodiments, the polypeptide has a molecular weight between about 20 kDa to about 60 kDa. In one embodiment, treating skin disorders associated with sebum dysregulation and/or abnormalities does not involve paralysis of a facial muscle.

In still another aspect, a method for treating an infection associated with sebum dysregulation and/or abnormalities in a subject is provided. In some embodiments, the method comprises administering to the subject a composition comprising a polypeptide having an amino acid sequence with at least about 90% sequence identity to an amino acid sequence in the full length of a botulinum toxin. In some embodiments, the method comprises administering to the subject a composition comprising a polypeptide having an amino acid sequence with at least about 90% sequence identity to an amino acid sequence in the binding domain of a botulinum toxin. In another embodiment, the method comprises administering to the subject a composition comprising a polypeptide having an amino acid sequence with at least about 90% sequence identity to an amino acid sequence in the amino or N-terminal half of the binding domain of the botulinum toxin ($H_{CN}$). In some embodiments, the method comprises administering to the subject a composition comprising a polypeptide having an amino acid sequence with at least about 90% sequence identity to a binding domain of a botulinum toxin. In some embodiments, the polypeptide has a molecular weight between about 20 kDa to about 60 kDa. In one embodiment, treating an infection associated with sebum dysregulation and/or abnormalities does not involve paralysis of a facial muscle.

In still another aspect, a method for treating inflammation associated with sebum dysregulation and/or abnormalities in a subject is provided. In some embodiments, the method comprises administering to the subject a composition comprising a polypeptide having an amino acid sequence with at least about 90% sequence identity to an amino acid sequence in the full length of a botulinum toxin. In some embodiments, the method comprises administering to the subject a composition comprising a polypeptide having an amino acid sequence with at least about 90% sequence identity to an amino acid sequence in the binding domain of a botulinum toxin. In another embodiment, the method comprises administering to the subject a composition comprising a polypeptide having an amino acid sequence with at least about 90% sequence identity to an amino acid sequence in the amino or N-terminal half of the binding domain of the botulinum toxin ($H_{CN}$). In some embodiments, the method comprises administering to the subject a composition comprising a polypeptide having an amino acid sequence with at least about 90% sequence identity to a binding domain of a botulinum toxin. In some embodiments, the polypeptide has a molecular weight between about 20 kDa to about 60 kDa. In one embodiment, treating inflammation associated with sebum dysregulation and/or abnormalities does not involve paralysis of a facial muscle.

In still another aspect, a method for modulating sebum dysregulation and/or abnormalities in a subject is provided. In some embodiments, the method comprises administering to the subject a composition comprising a polypeptide having an amino acid sequence with at least about 90% sequence identity to an amino acid sequence in the full length of a botulinum toxin. In some embodiments, the method comprises administering to the subject a composition comprising a polypeptide having an amino acid sequence with at least about 90% sequence identity to an amino acid sequence in the binding domain of a botulinum toxin. In another embodiment, the method comprises administering to the subject a composition comprising a polypeptide having an amino acid sequence with at least about 90% sequence identity to an amino acid sequence in the amino or N-terminal half of the binding domain of the botulinum toxin ($H_{CN}$). In some embodiments, the method comprises administering to the subject a composition comprising a polypeptide having an amino acid sequence with at least about 90% sequence identity to a binding domain of a botulinum toxin. In some embodiments, the polypeptide has a molecular weight between about 20 kDa to about 60 kDa. In one embodiment, modulating sebum dysregulation and/or abnormalities n does not involve paralysis of a facial muscle.

In other embodiments, the composition is formulated for topical, transdermal or intradermal administration.

In one embodiment, the polypeptide for use in any of the methods has at least about 90% sequence identity to a sequence selected from the group consisting of SEQ ID NOs: 1, 19, 3-18, and 25-27.

In other aspects, a polynucleotide is provided that is selected from the group consisting of:
(a) a cDNA which encodes a polypeptide comprising the binding domain of a botulinum toxin, wherein the molecular weight of the polypeptide is between about 1 kDa to about 90 kDa;
(b) a synthetic DNA which encodes a polypeptide comprising the binding domain of a botulinum toxin, wherein the molecular weight of the polypeptide is between about 1 kDa to about 90 kDa;
(c) a codon-optimized DNA which encodes a polypeptide comprising the binding domain of a botulinum toxin, wherein the molecular weight of the polypeptide is between about 1 kDa to about 90 kDa; and
(d) a DNA which is complementary to the DNA of any one of (a)-(c).

In other aspects, a polynucleotide is provided that is selected from the group consisting of:
(a) a cDNA which encodes a polypeptide comprising the binding domain of a botulinum toxin, wherein the molecular weight of the polypeptide is less than 50 kDa;
(b) a synthetic DNA which encodes a polypeptide comprising the binding domain of a botulinum toxin, wherein the molecular weight of the polypeptide is less than 50 kDa;
(c) a codon-optimized DNA which encodes a polypeptide comprising the binding domain of a botulinum toxin, wherein the molecular weight of the polypeptide is less than 50 kDa; and
(d) a DNA which is complementary to the DNA of any one of (a)-(c).

In other aspects, a polynucleotide is provided that is selected from the group consisting of:
(a) a cDNA which encodes a polypeptide comprising the binding domain of a botulinum toxin, wherein the molecular weight of the polypeptide is greater than 1 kDa but less than 15 kDa;
(b) a synthetic DNA which encodes a polypeptide comprising the binding domain of a botulinum toxin, wherein the molecular weight of the polypeptide is greater than 1 kDa but less than 15 kDa;
(c) a codon-optimized DNA which encodes a polypeptide comprising the binding domain of a botulinum toxin, wherein the molecular weight of the polypeptide is greater than 1 kDa but less than 15 kDa; and
(d) a DNA which is complementary to the DNA of any one of (a)-(c).

In another still another aspect, a polynucleotide is provided which comprises at least 50%, at least 60%, at least 70%, at least 75%, at least 80%, at least 85%, at least 90% or greater % sequence identity to the polynucleotide sequence of SEQ ID NO: 2 or a nucleic acid encoding a polypeptide selected from the group consisting of SEQ ID NO: 1, SEQ ID NO: 19, SEQ ID NOs: 3-5, SEQ ID NO: 6, SEQ ID NO: 20, SEQ ID Nos: 7-10, SEQ ID NO: 11, SEQ ID NO: 21, SEQ ID NOs: 12-18, and SEQ ID NOs: 25-27 or a degenerate thereof or an RNA equivalent thereof.

In yet another embodiment, the polynucleotide consists essentially of the nucleic acid sequence set forth in SEQ ID NO: 2 or a degenerate thereof or an RNA equivalent thereof.

In another aspect, a vector comprising a polynucleotide as described herein is provided. In other aspects, a host cell comprising the vector is provided. In one embodiment, the host cell is not *Clostridium botulinum*.

In other aspects, kits, compositions, and methods of using the kits and compositions are provided. In one embodiment, a kit is provided, comprising, in one or more packages, a vector and instructions for expressing the polynucleotide in a suitable host cell. In another embodiment, a composition comprising a vector or a host cell and a pharmaceutical excipient is provided. In still another embodiment, a method to improve a skin quality attribute that comprises administering to a subject the composition comprising a vector or a host cell to achieve expression of the polypeptide is provided.

BRIEF DESCRIPTION OF THE SEQUENCES

SEQ ID NO: 1 is the amino acid sequence of the cell binding domain of BoNT/A1 (H$_C$/A):

TSILNLRYESNHLIDLSRYASKINIGSKVNFDPIDKNQIQLFNLESSKIE
VILKNAIVYNSMYENFSTSFWIRIPKYFNSISLNNEYTIINCMENNSGWK
VSLNYGEIIWTLQDTQEIKQRVVFKYSQMINISDYINRWIFVTITNNRLN
NSKIYINGRLIDQKPISNLGNIHASNNIMFKLDGCRDTHRYIWIKYFNLF
DKELNEKEIKDLYDNQSNSGILKDFWGDYLQYDKPYYMLNLYDPNKYVDV
NNVGIRGYMYLKGPRGSVMTTNIYLNSSLYRGTKFIIKKYASGNKDNIVR
NNDRVYINVVVKNKEYRLATNASQAGVEKILSALEIPDVGNLSQVVVMKS
KNDQGITNKCKMNLQDNNGNDIGFIGFHQFNNIAKLVASNWYNRQIERSS
RTLGCSWEFIPVDDGWGERPL

SEQ ID NO: 19 is the amino acid sequence of the cell binding domain of BoNT/A1 (H$_C$/A) further comprising a N-terminal his-tag (amino acids which make up the N-terminal tag are underlined):

MGSSHHHHHHSSGLVPRGSHMDTSILNLRYESNHLIDLSRYASKINIGSK
VNFDPIDKNQIQLFNLESSKIEVILKNAIVYNSMYENFSTSFWIRIPKYF
NSISLNNEYTIINCMENNSGWKVSLNYGEIIWTLQDTQEIKQRVVFKYSQ
MINISDYINRWIFVTITNNRLNNSKIYINGRLIDQKPISNLGNIHASNNI
MFKLDGCRDTHRYIWIKYFNLFDKELNEKEIKDLYDNQSNSGILKDFWGD
YLQYDKPYYMLNLYDPNKYVDVNNVGIRGYMYLKGPRGSVMTTNIYLNSS
LYRGTKFIIKKYASGNKDNIVRNNDRVYINVVVKNKEYRLATNASQAGVE
KILSALEIPDVGNLSQVVVMKSKNDQGITNKCKMNLQDNNGNDIGFIGFH
QFNNIAKLVASNWYNRQIERSSRTLGCSWEFIPVDDGWGERPLQ

SEQ ID NO: 2 is the DNA sequence of the cell binding domain of BoNT/A1:

accagcattctgaacctgcgttatgaaagcaaccatctgattgatctgag
ccgttatgcgagcaaaattaacattggcagcaaagtgaactttgatccga
ttgataagaaccagattcagctgtttaacctggaaagcagcaaaattgaa
gtgattctgaagaacgcgattgtgtataacagcatgtatgaaaactttag
caccagcttttggattcgtattccgaaatattttaacagcattagcctga
acaacgaatataccattattaactgcatggaaaacaacagcggctggaaa
gtgagcctgaactatggcgaaattatttggaccctgcaggatacccagga
aattaaacagcgtgtggtgtttaaatatagccagatgattaacattagcg
attatattaaccgttggatctttgtgaccattaccaacaaccgtctgaac aacagcaaaatttatattaacggccgtctgattgatcagaaaccgattag
caacctgggcaacattcatgcgagcaacaacattatgtttaaactggatg
gctgccgtgataccatcgttatatttggattaaatattttaacctgttt
gataaagagctcaacgagaaagaaattaaagatctgtatgataaccagag
caacagcggcattctgaaagatttctggggcgattatctgcagtatgata
aaccgtattatatgctgaacctgtatgatccgaacaaatatgtggatgtg
aacaacgtgggcattcgtggctatatgtatctgaaaggcccgcgtggcag
cgtgatgaccaccaacatttatctgaacagcagcctgtatcgtggcacca
aatttattattaagaagtatgcgagcggcaacaaagataacattgtgcgt
aacaacgatcgtgtgtatattaacgtggtggtgaagaacaaagaatatcg
tctggcgaccaacgcgagccaggcgggcgtggaaaagattctgagcgcgc
tggaaattccggatgtgggcaacctgagccaggtggtggtgatgaaaagc
aagaacgatcagggcattaccaacaaatgcaaaatgaacctgcaggataa
caacggcaacgatattggctttattggctttcatcagtttaacaacattg
cgaaactggtggcgagcaactggtataaccgtcagattgaacgtagcagc
cgtaccctgggctgcagctgggaatttattccggtggatgatggctgggg
cgaacgtccgctgtaa SEQ ID NO: 3 is an amino acid sequence of the binding domain region within the heavy chain of BoNT/B, H$_C$/B, (GENBANK Accession No. BAE48264):

NIILNLRYKDNNLIDLSGYGAKVEVYDGVELNDKNQFKLTSSANSKIRVT
QNQNIIFNSVFLDFSVSFWIRIPKYKNDGIQNYIHNEYTIINCMKNNSGW
KISIRGNRIIWTLIDINGKTKSVFFEYNIREDISEYINRWFFVTITNNLN
NAKIYINGKLESNTDIKDIREVIANGEIIFKLDGDIDRTQFIWMKYFSIF
NTELSQSNIEERYKIQSYSEYLKDFWGNPLMYNKEYYMFNAGNKNSYIKL
KKDSPVGEILTRSKYNQNSKYINYRDLYIGEKFIIRRKSNSQSINDDIVR
KEDYIYLDFFNLNQEWRVYTYKYFKKEEEKLFLAPISDSDEFYNTIQIKE
YDEQPTYSCQLLFKKDEESTDEIGLIGIHRFYESGIVFEEYKDYFCISKW
YLKEVKRKPYNLKLGCNWQFIPKDEGWTE

SEQ ID NO: 4 is an amino acid sequence of the binding domain region within the heavy chain of BoNT/C, H$_C$/C, (GENBANK Accession No. P18640):

SKILSLQNRKNTLVDTSGYNAEVSEEGDVQLNPIFPFDFKLGSSGEDRGK
VIVTQNENIVYNSMYESFSISFWIRINKWVSNLPGYTIIDSVKNNSGWSI
GIISNFLVFTLKQNEDSEQSINFSYDISNNAPGYNKWFFVTVTNNMMGNM
KIYINGKLIDTIKVKELTGINFSKTITFEINKIPDTGLITSDSDNINMWI
RDFYIFAKELDGKDINILFNSLQYTNVVKDYWGNDLRYNKEYYMVNIDYL
NRYMYANSRQIVFNTRRNNNDFNEGYKIIIKRIRGNTNDTRVRGGDILYF
DMTINNKAYNLFMKNETMYADNHSTEDIYAIGLREQTKDINDNIIFQIQP

-continued

MNNTYYYASQIFKSNFNGENISGICSIGTYRFRLGGDWYRHNYLVPTVKQ

GNYASLLESTSTHWGFVPVSE

SEQ ID NO: 5 is an amino acid sequence of the binding domain region within the heavy chain of BoNT/D, H$_C$/D, (GENBANK Accession No. P19321):

SKILSLQNKKNALVDTSGYNAEVRVGDNVQLNTIYTNDFKLSSSGDKIIV

NLNNNILYSAIYENSSVSFWIKISKDLTNSHNEYTIINSIEQNSGWKLCI

RNGNIEWILQDVNRKYKSLIFDYSESLSHTGYTNKWFFVTITNNIMGYMK

LYINGELKQSQKIEDLDEVKLDKTIVFGIDENIDENQMLWIRDFNIFSKE

LSNEDINIVYEGQILRNVIKDYWGNPLKFDTEYYIINDNYIDRYIAPESN

VLVLVQYPDRSKLYTGNPITIKSVSDKNPYSRILNGDNIILHMLYNSRKY

MIIRDTDTIYATQGGECSQNCVYALKLQSNLGNYGIGIFSIKNIVSKNKY

CSQIFSSFRENTMLLADIYKPWRFSFKNAYTPVAVTNYETKLLSTSSFWK

FISRDPGWVE

SEQ ID NO: 6 is an amino acid sequence of the binding domain region within the heavy chain of BoNT/DC, H$_C$/DC, (GENBANK Accession No. EF378947):

SKILSLQNKKNTLMDTSGYNAEVRVEGNVQLNPIFPFDFKLGSSGDDRGK

VIVTQNENIVYNAMYESFSISFWIRINKWVSNLPGYTIIDSVKNNSGWSI

GIISNFLVFTLKQNENSEQDINFSYDISKNAAGYNKWFFVTITTNMNIGN

MMIYINGKLIDTIKVKELTGINFSKTITFQMNKIPNTGLITSDSDNINMW

IRDFYIFAKELDDKDINILFNSLQYTNVVKDYWGNDLRYDKEYYMINVNY

MNRYMSKKGNGIVFNTRKNNNDFNEGYKIIIKRIRGNTNDTRVRGENVLY

NTTIDNKQYSLGMYKPSRNLGTDLVPLGALDQPMDEIRKYGSFIIQPCNT

FDYYASQLFLSSNATTNRLGILSIGSYSFKLGDDYWFNHEYLIPVIKIEH

YASLLESTSTHWVFVPASE

SEQ ID NO: 20 is an amino acid sequence of the binding domain region within the heavy chain of BoNT/DC further comprising a N-terminal his-tag (amino acids which make up the N-terminal tag are underlined) (GENBANK Accession No. EF378947):

<u>MGSSHHHHHHSSGLVPRGSHMD</u>SKILSLQNKKNTLMDTSGYNAEVRVEGN

VQLNPIFPFDFKLGSSGDDRGKVIVTQNENIVYNAMYESFSISFWIRONK

WVSNLPGYTIIDSVKNNSGWSIGIISNFLVFTLKQNENSEQDINFSYDIS

KNAAGYNKWFFVTITTNMMGNMMIYINGKLIDTIKVKELTGINFSKTITF

QMNKIPNTGLITSDSDNINMWIRDFYIFAKELDDKDINILFNSLQYTNVV

KDYWGNDLRYDKEYYMINVNYMNRYMSKKGNGIVFNTRKNNNDFNEGYKI

IIKRIRGNTNDTRVRGENVLYFNTTIDNKQYSLGMYKPSRNLGTDLVPLG

ALDQPMDEIRKYGSFIIQPCNTFDYYASQLFLSSNATTNRLGILSIGSYS

FKLGDDYWFNHEYLIPVIKIEHYASLLESTSTHWVFVPASEQ

SEQ ID NO: 7 is an amino acid sequence of the binding domain region within the heavy chain of BoNT/E, H$_C$/E, (GENBANK Accession No. AFV91344):

SSVLNMRYKNDKYVDTSGYDSNININGDVYKYPTNKNQFGIYNDKLSEVN

ISQNDYIIYDNKYKNFSISFWVRIPNYDNKIVNVNNEYTIINCMRDNNSG

WKVSLNHNEIIWTLQDNAGINQKLAFNYGNANGISDYINKWIFVTITNDR

LGDSKLYINGNLIDQKSILNLGNIHVSDNILFKIVNCSYTRYIGIRYFNV

FDKELDETEIQTLYSNEPNTNILKDFWGNYLLYDKEYYLLNVLKPNNFID

RRKDSTLSINNIRSTILLANRLYSGIKVKIQRVNNSSTNDNLVRKNDQVY

INFVASKTHLFPLYADTATTNKEKTIKISSSGNRFNQVVVMNSVGNNCTM

NFKNNNGNNIGLLGFKADTVVASTWYYTHMRDHTNSNGCFWNFISEEHGW

QEK

SEQ ID NO: 8 is an amino acid sequence of the binding domain region within the heavy chain of BoNT/F, H$_C$/F, (GENBANK Accession No. ABS41202):

NSILDMRYENNKFIDISGYGSNISINGDVYIYSTNRNQFGIYSSKPSEVN

IAQNNDIIYNGRYQNFSISFWVRIPKYFNKVNLNNEYTIIDCIRNNNSGW

KISLNYNKIIWTLQDTAGNNQKLVFNYTQMISISDYINKWIFVTITNNRL

GNSRIYINGNLIDEKSISNLGDIHVSDNILFKIVGCNDTRYVGIRYFKVF

DTELGKTEIETLYSDEPDPSILKDFWGNYLLYNKRYYLLNLLRTDKSITQ

NSNFLNINQQRGVYQKPNIFSNTRLYTGVEVIIRKNGSTDISNTDNFVRK

NDLAYINVVDRDVEYRLYADISIAKPEKIIKLIRTSNSNNSLGQIIVMDS

IGNNCTMNFQNNNGGNIGLLGFEISNNLVASSWYYNNIRKNTSSNGCFWS

FISKEHGWQEN

SEQ ID NO: 9 is an amino acid sequence of the binding domain region within the heavy chain of BoNT/G, H$_C$/G, (GENBANK Accession No. X74162):

NAILSLSYRGGRLIDSSGYGATMNVGSDVIFNDIGNGQFKLNNSENSNIT

AHQSKFVVYDSMFDNFSINFWVRTPKYNNNDIQTYLQNEYTIISCIKNDS

GWKVSIKGNRIIWTLIDVNAKSKSIFFEYSIKDNISDYINKWFSITITND

RLGNANIYINGSLKKSEKILNLDRINSSNDIDFKLINCTDTTKFVWIKDF

NIFGRELNATEVSSLYWIQSSTNTLKDFWGNPLRYDTQYYLFNQGMQNIY

IKYFSKASMGETAPRTNFNNAAINYQNLYLGLRFIIKKASNSRNINNDNI

VREGDYIYLNIDNISDESYRVYVLVNSKEIQTQLFLAPINDDPTFYDVLQ

IKKYYEKTTYNCQILCEKDTKTFGLFGIGKFVKDYGYVWDTYDNYFCISQ

WYLRRISENINKLRLGCNWQFIPVDEGWTE

SEQ ID NO: 10 is an amino acid sequence of the binding domain region within the heavy chain of BoNT/X, H$_C$/X, (GENBANK Accession No. BAQ12790):

VLNLGAEDGKIKDLSGTTSDINIGSDIELADGRENKAIKIKGSENSTIKI

AMNKYLRFSATDNFSISFWIKHPKPTNLLNNGIEYTLVENFNQRGWKISI

QDSKLIWYLRDHNNSIKIVTPDYIAFNGWNLITITNNRSKGSIVYVNGSK

IEEKDISSIWNTEVDDPIIFRLKNNRDTQAFTLLDQFSIYRKELNQNEVV

KLYNYYFNSNYIRDIWGNPLQYNKKYYLQTQDKPGKGLIREYWSSFGYDY

-continued

VILSDSKTITFPNNIRYGALYNGSKVLIKNSKKLDGLVRNKDFIQLEIDG

YNMGISADRFNEDTNYIGTTYGTTHDLTTDFEIIQRQEKYRNYCQLKTPY

NIFHKSGLMSTETSKPTFHDYRDWVYSSAWYFQNYENLNLRKHTKTNWYF

IPKDEGWDED

SEQ ID NO: 11 is an amino acid sequence corresponding to residues 1-218 of the amino acid sequence of the cell binding domain of BoNT/A1, referred to as the N-terminal fragment of the cell binding domain and abbreviated $H_{CN}/A$ (PDB ID: 3BTA, 4JRA):

TSILNLRYESNHLIDLSRYASKINIGSKVNFDPIDKNQIQLFNLESSKIE

VILKNAIVYNSMYENFSTSFWIRIPKYFNSISLNNEYTIINCMENNSGWK

VSLNYGEIIWTLQDTQEIKQRVVFKYSQMINISDYINRWIFVTITNNRLN

NSKIYINGRLIDQKPISNLGNIHASNNIMFKLDGCRDTHRYIWIKYFNLF

DKELNEKEIKDLYDNQSN

SEQ ID NO: 21 is an amino acid sequence that includes an N-terminal histidine tag and residues 1-218 of the amino acid sequence of the cell binding domain of BoNT/A1, referred to as the N-terminal fragment of the cell binding domain and abbreviated $H_{CN}/A$, (amino acids which make up the N-terminal tag are underlined):

MGSSHHHHHHSSGLVPRGSHMDTSILNLRYESNHLIDLSRYASKINIGSK

VNFDPIDKNQIQLFNLESSKIEVILKNAIVYNSMYENFSTSFWIRIPKYF

NSISLNNEYTIINCMENNSGWKVSLNYGEIIWTLQDTQEIKQRVVEKYSQ

MINISDYINRWIFVTITNNRLNNSKIYINGRLIDQKPISNLGNIHASNNI

MFKLDGCRDTHRYIWIKYFNLFDKELNEKEIKDLYDNQSN

SEQ ID NO: 12 is an amino acid sequence from the N-terminal region of the binding domain of BoNT/B, $H_{CN}/B$ (PDB ID: 2NM1):

NIILNLRYKDNNLIDLSGYGAKVEVYDGVELNDKNQFKLTSSANSKIRVT

QNQNIIFNSVFLDFSVSFWIRIPKYKNDGIQNYIHNEYTIINCMKNNSGW

KISIRGNRIIWTLIDINGKTKSVFFEYNIREDISEYINRWFFVTITNNLN

NAKIYINGKLESNTDIKDIREVIANGEIIFKLDGDIDRTQFIWMKYFSIF

NTELSQSNIEERYKIQSYSEY

SEQ ID NO: 13 is an amino acid sequence from the N-terminal region of the binding domain of BoNT/C, $H_{CN}/C$ (PDB ID: 3R4U):

SKILSLQNRKNTLVDTSGYNAEVSEEGDVQLNPIFPFDFKLGSSGEDRGK

VIVTQNENIVYNSMYESFSISFWIRINKWVSNLPGYTIIDSVKNNSGWSI

GIISNFLVFTLKQNEDSEQSINFSYDISNNAPGYNKWFFVTVTNNMNIGN

MKIYINGKLIDTIKVKELTGINFSKTITFEINKIPDTGLITSDSDNINMW

IRDFYIFAKELDGKDINILFNSLQYTN

SEQ ID NO: 14 is an amino acid sequence from the N-terminal region of the binding domain of BoNT/D, $H_{CN}/D$ (PDB ID: 3N7J):

SKILSLQNKKNALVDTSGYNAEVRVGDNVQLNTIYTNDFKLSSSGDKIIV

NLNNNILYSAIYENSSVSFWIKISKDLTNSHNEYTIINSIEQNSGWKLCI

RNGNIEWILQDVNRKYKSLIFDYSESLSHTGYTNKWFFVTITNNIMGYMK

LYINGELKQSQKIEDLDEVKLDKTIVFGIDENIDENQMLWIRDFNIFSKE

LSNEDINIVYEGQIL

SEQ ID NO: 15 is an amino acid sequence from the N-terminal region of the binding domain of BoNT/DC $H_{CN}/DC$ (PDB ID: 4ISQ):

SKILSLQNKKNTLMDTSGYNAEVRVEGNVQLNPIFPFDFKLGSSGDDRGK

VIVTQNENIVYNAMYESFSISFWIRINKWVSNLPGYTIIDSVKNNSGWSI

GIISNFLVFTLKQNENSEQDINFSYDISKNAAGYNKWFFVTITTNMMGNM

MIYINGKLIDTIKVKELTGINFSKTITFQMNKIPNTGLITSDSDNINMWI

RDFYIFAKELDDKDINILFNSLQYTN

SEQ ID NO: 16 is an amino acid sequence from the N-terminal region of the binding domain of BoNT/E, $H_{CN}/E$ (PDB: 4ZKT):

SSVLNMRYKNDKYVDTSGYDSNININGDVYKYPTNKNQFGIYNDKLSEVN

ISQNDYIIYDNKYKNFSISFWVRIPNYDNKIVNVNNEYTIINCMRDNNSG

WKVSLNHNEIIWTLQDNAGINQKLAFNYGNANGISDYINKWIFVTITNDR

LGDSKLYINGNLIDQKSILNLGNIHVSDNILFKIVNCSYTRYIGIRYFNV

FDKELDETEIQTLYSNEPNTN

SEQ ID NO: 17 is an amino acid sequence from the N-terminal region of the binding domain of BoNT/F, $H_{CN}/F$ (PDB ID: 3RSJ):

NSILDMRYENNKFIDISGYGSNISINGDVYIYSTNRNQFGIYSSKPSEVN

IAQNNDIIYNGRYQNFSISFWVRIPKYFNKVNLNNEYTIIDCIRNNNSGW

KISLNYNKIIWTLQDTAGNNQKLVFNYTQMISISDYINKWIFVTITNNRL

GNSRIYINGNLIDEKSISNLGDIHVSDNILFKIVGCNDTRYVGIRYFKVF

DTELGKTEIETLYSDEPD

SEQ ID NO: 18 is an amino acid sequence from the N-terminal region of the binding domain of BoNT/G, $H_{CN}/G$ (PDB ID: 2VXR):

NAILSLSYRGGRLIDSSGYGATMNVGSDVIFNDIGNGQFKLNNSENSNIT

AHQSKFVVYDSMFDNFSINFWVRTPKYNNNDIQTYLQNEYTIISCIKNDS

GWKVSIKGNRIIWTLIDVNAKSKSIFFEYSIKDNISDYINKWFSITITND

RLGNANIYINGSLKKSEKILNLDRINSSNDIDFKLINCTDTTKFVWIKDF

NIFGRELNATEVSSLYWIQSSTNT

BRIEF DESCRIPTION OF THE DRAWINGS

The details of one or more embodiments of the disclosure are set forth in the accompanying drawings/tables and the description below. Other features, objects, and advantages of the disclosure will be apparent from the drawings/tables and detailed description, and from the claims.

DETAILED DESCRIPTION

Figure 1:
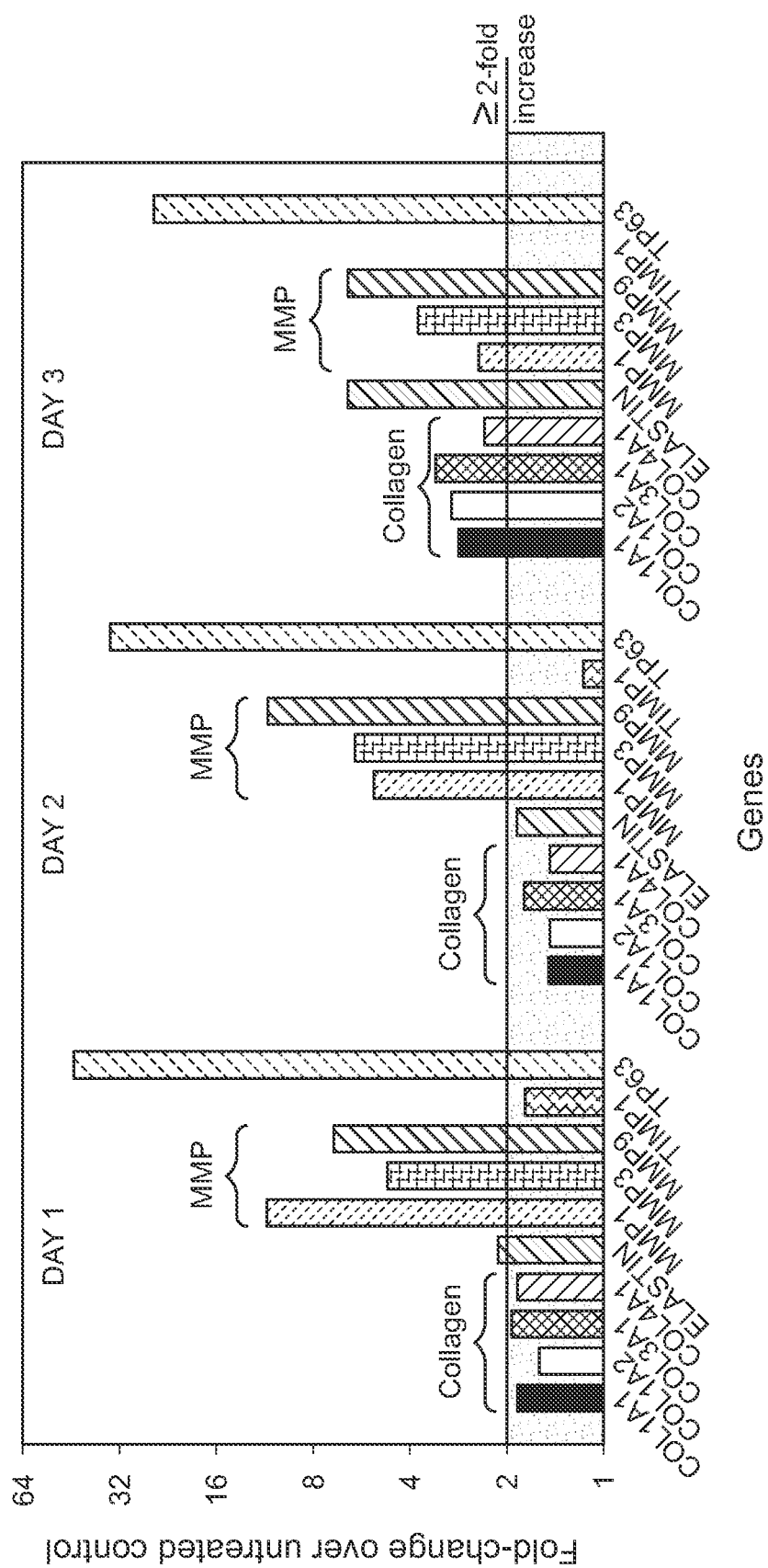
FIG. 1 is a bar graph showing the fold-change in expression of the indicated genes in normal human primary fibroblast cells after treatment with 1 µM of an exemplary polypeptide provided in accordance with aspects of the present disclosure, having an amino acid sequence of SEQ ID NO: 19 for 1, 2 or 3 days, where the fold-change is expressed relative to untreated control cells.

Various aspects will be described more fully hereinafter. Such aspects may, however, be embodied in many different forms and should not be construed as limited to the embodiments set forth herein; rather, these embodiments are provided so that this disclosure will be thorough and complete.

Definitions

Where a range of values is provided in this disclosure, it is intended that each intervening value between the upper and lower limit of that range and any other stated or intervening value in that stated range is encompassed within the disclosure. For example, if a range of 1 µM to 8 µM is stated, it is intended that 2 µM, 3 µM, 4 µM, 5 µM, 6 µM, and 7 µM are also explicitly disclosed, as well as the range of values greater than or equal to 1 µM and the range of values less than or equal to 8 µM.

The singular forms "a," "an," and "the" include plural referents unless the context clearly dictates otherwise. Thus, for example, reference to an "amino acid" includes a single amino acid as well as two or more of the same or different amino acids.

The word "about" means a range of plus or minus 10% of that value, e.g., "about 50" means 45 to 55, "about 25,000" means 22,500 to 27,500, etc., unless the context of the disclosure indicates otherwise, or is inconsistent with such an interpretation. For example, in a list of numerical values such as "about 49, about 50, about 55, "about 50" means a range extending to less than half the interval(s) between the preceding and subsequent values, e.g., more than 49.5 to less than 52.5.

"Administration", or "to administer" means the step of giving (i.e. administering) a pharmaceutical composition to a subject, or alternatively a subject receiving a pharmaceutical composition. The pharmaceutical compositions disclosed herein can be locally administered by various methods. For example, intramuscular, intradermal, subcutaneous administration, intrathecal administration, intraperitoneal administration, topical (transdermal), instillation, and implantation (for example, of a slow-release device such as polymeric implant or miniosmotic pump) can all be appropriate routes of administration.

"Alleviating" means a reduction in the occurrence of a pain, of a headache, or of any symptom or cause of a condition or disorder. Thus, alleviating includes some reduction, significant reduction, near total reduction, and total reduction.

The term "amino acid" means a naturally occurring or synthetic amino acid, as well as amino acid analogs, stereoisomers, and amino acid mimetics that function similarly to the naturally occurring amino acids. Included by this definition are natural amino acids such as: (1) histidine (His; H) (2) isoleucine (Ile; I) (3) leucine (Leu; L) (4) Lysine (Lys; K) (5) methionine (Met; M) (6) phenylalanine (Phe; F) (7) threonine (Thr; T) (8) tryptophan (Trp; W) (9) valine (Val; V) (10) arginine (Arg; R) (11) cysteine (Cys; C) (12) glutamine (Gln; Q) (13) glycine (Gly; G) (14) proline (Pro; P) (15) serine (Ser; S) (16) tyrosine (Tyr; Y) (17) alanine (Ala; A) (18) asparagine (Asn; N) (19) aspartic acid (Asp; D) (20) glutamic acid (Glu; E) (21) selenocysteine (Sec; U); including unnatural amino acids: (a) citrulline (Cit); (b) cystine; (c) gamma-amino butyric acid (GABA); (d) ornithine (Orn); (f) theanine; (g) homocysteine (Hcy); (h) thyroxine (Thx); and amino acid derivatives such as betaine; carnitine; carnosine creatine; hydroxytryptophan; hydroxyproline (Hyp); N-acetyl cysteine; S-Adenosyl methionine (SAM-e); taurine; tyramine.

"Amino acid residue" means the individual amino acid units incorporated into a polypeptide.

"Animal protein free" means the absence of blood derived, blood pooled and other animal derived products or compounds. "Animal" means a mammal (such as a human), bird, reptile, fish, insect, spider or other animal species. "Animal" excludes microorganisms, such as bacteria. Thus, an animal protein free pharmaceutical composition can include a botulinum neurotoxin. For example, an "animal protein free" pharmaceutical composition means a pharmaceutical composition which is either substantially free or essentially free or entirely free of a serum derived albumin, gelatin and other animal derived proteins, such as immunoglobulins. An example of an animal protein free pharmaceutical composition is a pharmaceutical composition which comprises or which consists of a botulinum toxin (as the active ingredient) and a suitable polysaccharide as a stabilizer or excipient.

"Binding domain" of a toxin as used herein encompasses the wild type binding domain, variants and/or fragments thereof.

"Botulinum toxin" means a neurotoxin produced by *Clostridium botulinum*, as well as a botulinum toxin (or the light chain or the heavy chain thereof) made recombinantly by a non-Clostridial species. The phrase "botulinum toxin", as used herein, encompasses the botulinum toxin serotypes A, B, C, D, E, F, G, H and X, and their subtypes, mosaic toxins, such as BoNT/DC and BoNT/CD, and any other types of subtypes thereof, or any re-engineered proteins, analogs, derivatives, homologs, parts, sub-parts, variants, or versions, in each case, of any of the foregoing. "Botulinum toxin", as used herein, also encompasses a "modified botulinum toxin". Further "botulinum toxin" as used herein also encompasses a botulinum toxin complex, (for example, the 300, 600 and 900 kDa complexes), as well as the neurotoxic component of the botulinum toxin (150 kDa) that is unassociated with the complex proteins.

"Clostridial toxin" refers to any toxin produced by a Clostridial toxin strain that can execute the overall cellular mechanism whereby a Clostridial toxin intoxicates a cell and encompasses the binding of a Clostridial toxin to a low or high affinity Clostridial toxin receptor, the internalization of the toxin/receptor complex, the translocation of the Clostridial toxin light chain into the cytoplasm and the enzymatic modification of a Clostridial toxin substrate. Non-limiting examples of Clostridial toxins include Botulinum toxins, such as a BoNT/A, a BoNT/B, a BoNT/$C_1$, a BoNT/D, a BoNT/CD, a BoNT/DC, a BoNT/E, a BoNT/F, a BoNT/G, a BoNT/H (aka type FA or HA), a BoNT/X, a BoNT/J, a Tetanus toxin (TeNT), a Baratii toxin (BaNT), and a Butyricum toxin (BuNT). The BoNT/$C_2$ cytotoxin and BoNT/$C_3$ cytotoxin, not being neurotoxins, are excluded from the term "Clostridial toxin." The term Clostridial toxin also includes the approximately 150-kDa Clostridial toxin alone (i.e. without the NAPs). A Clostridial toxin includes naturally occurring Clostridial toxin variants, such as, e.g., Clostridial toxin isoforms and Clostridial toxin subtypes; non-naturally occurring Clostridial toxin variants, such as, e.g., conservative Clostridial toxin variants, non-conservative Clostridial toxin variants, Clostridial toxin chimeric variants and active Clostridial toxin fragments thereof, or any combination thereof. A Clostridial toxin also includes Clostridial toxin complexes, which refers to a complex comprising a Clostridial toxin and non-toxin associated proteins (NAPs), such as, e.g., a Botulinum toxin complex, a Tetanus toxin complex, a Baratii toxin complex, and a Butyricum toxin complex. Non-limiting examples of Clostridial toxin complexes include those produced by a *Clostridium botulinum*, such as, e.g., a 900-kDa BoNT/A complex, a 500-kDa BoNT/A complex, a 300-kDa BoNT/A complex, a 500-kDa BoNT/B complex, a 500-kDa BoNT/$C_1$ complex, a 500-kDa BoNT/D complex, a 300-kDa BoNT/D complex, a 300-kDa BoNT/E complex, and a 300-kDa BoNT/F complex.

"Cellular phenotype" refers to any change in gene expression, protein expression, synthesis of factors, and/or secretion of proteins and factors that affect the structure and/or function of a cell and/or the tissue that the cell is a part of, including extracellular matrix structure and sebum.

"Effective amount" as applied to the biologically active ingredient means that amount of the ingredient which is generally sufficient to affect a desired change in the subject. For example, where the desired effect is a reduction in sebum, an effective amount of the ingredient is that amount which causes at least a substantial reduction of sebum, and without resulting in significant toxicity.

"Effective amount" when used in reference to the amount of an excipient or specific combination of excipients added to a Clostridial toxin composition, refers to the amount of each excipient that is necessary to achieve the desired initial recovered potency of a Clostridial toxin active ingredient. In aspects of this embodiment, an effective amount of an excipient or combination of excipients results in an initial recovered potency of, e.g., at least 10%, at least 20%, at least 30%, at least 40%, at least 50%, at least 60%, at least 70%, at least 80%, at least 90% or at least 100%. In other aspects of this embodiment, a therapeutically effective concentration of a Clostridial toxin active ingredient reduces a symptom associated with the aliment being treated by, e.g., at most 10%, at most 20%, at most 30%, at most 40%, at most 50%, at most 60%, at most 70%, at most 80%, at most 90% or at most 100%.

"Heavy chain" means the heavy chain of a botulinum neurotoxin. It has a molecular weight of about 100 kDa and can be referred to as the H chain, or as H.

$H_C$ means a fragment (about 50 kDa) derived from the H chain of a botulinum neurotoxin which is approximately equivalent to the carboxyl end segment of the H chain, or the portion corresponding to that fragment in the intact H chain. It is believed to contain the portion of the natural or wild type botulinum neurotoxin involved in high affinity, presynaptic binding to motor neurons.

$H_N$ means a fragment (about 50 kDa) derived from the H chain of a botulinum neurotoxin which is approximately equivalent to the amino end segment of the H chain, or the portion corresponding to that fragment in the intact in the H chain. It is believed to contain the portion of the natural or wild type botulinum neurotoxin involved in the translocation of the L chain across an intracellular endosomal membrane.

"Homolog" means a protein in a group of proteins that perform the same biological function, e.g., proteins that belong to the same Clostridial toxin family and that provide a common activity, e.g., receptor-binding activity. Homologs are generally expressed by homologous genes.

"Isolated" means a nucleic acid sequence or a polypeptide sequence that is separated from the wild or native sequence in which it naturally occurs or is in an environment different from that in which the sequence naturally occurs.

"Light chain" means the light chain of a Clostridial neurotoxin. It has a molecular weight of about 50 kDa, and can be referred to as the L chain, L, or as the proteolytic domain (amino acid sequence) of a botulinum neurotoxin.

$LH_N$ or $L-H_N$ means a fragment derived from a Clostridial neurotoxin that contains the L chain, or a functional fragment thereof coupled to the $H_N$ domain. It can be obtained from the intact Clostridial neurotoxin by proteolysis, so as to remove or to modify the $H_C$ domain.

"Implant" means a controlled release (e.g., pulsatile or continuous) composition or drug delivery system. The implant can be, for example, injected, inserted or implanted into a human body.

"Local administration" means direct administration of a pharmaceutical at or to the vicinity of a site on or within an animal body, at which site a biological effect of the pharmaceutical is desired, such as via, for example, intramuscular or intra- or subdermal injection or topical administration. Local administration excludes systemic routes of administration, such as intravenous or oral administration. Topical administration is a type of local administration in which a pharmaceutical agent is applied to a patient's skin.

"Modified botulinum toxin" means a botulinum toxin that has had at least one of its amino acids deleted, modified, or replaced, as compared to a native botulinum toxin. Additionally, the modified botulinum toxin can be a recombinantly produced neurotoxin, or a derivative or fragment of a recombinantly made neurotoxin. A modified botulinum toxin retains at least one biological activity of the native botulinum toxin, such as, the ability to bind to a botulinum toxin receptor, or the ability to inhibit neurotransmitter release from a neuron. One example of a modified botulinum toxin is a botulinum toxin that has a light chain from one botulinum toxin serotype (such as serotype A), and a heavy chain from a different botulinum toxin serotype (such as serotype B). Another example of a modified botulinum toxin is a botulinum toxin coupled to a neurotransmitter, such as substance P.

"Mutation" means a structural modification of a naturally occurring protein or nucleic acid sequence. For example, in the case of nucleic acid mutations, a mutation can be a deletion, addition or substitution of one or more nucleotides in the DNA sequence. In the case of a protein sequence mutation, the mutation can be a deletion, addition or substitution of one or more amino acids in a protein sequence. For example, a specific amino acid comprising a protein sequence can be substituted for another amino acid, for example, an amino acid selected from a group which includes the amino acids alanine, asparagine, cysteine, aspartic acid, glutamic acid, phenylalanine, glycine, histidine, isoleucine, lysine, leucine, methionine, proline, glutamine, arginine, serine, threonine, valine, tryptophan, tyrosine or any other natural or non-naturally occurring amino acid or chemically modified amino acids. Mutations to a protein sequence can be the result of mutations to DNA sequences that when transcribed, and the resulting mRNA translated, produce the mutated protein sequence. Mutations to a protein sequence can also be created by fusing a peptide sequence containing the desired mutation to a desired protein sequence.

"Patient" means a human or non-human subject receiving medical or veterinary care. Accordingly, the compositions as disclosed herein can be used in treating any animal, such as, for example, mammals, or the like.

"Peptide" and "polypeptide" refer to any polymer made up of a chain of amino acid residues linked by peptide bonds, regardless of its size. Although "protein" is often used in reference to relatively large polypeptides, and "peptide" is often used in reference to small polypeptides, usage of these terms in the art overlaps and varies. Thus, for simplicity, the term "polypeptide" will be used herein, although in some cases the art may refer to the same polymer as a "protein." Unless otherwise indicated, the sequence for a polypeptide is given in the order from the amino terminus to the carboxyl terminus.

An amino acid sequence or a nucleotide sequence is "substantially identical", "substantially the same as" or "substantially similar to" a reference sequence if the amino sequence or nucleotide sequence has at least 85% sequence identity with the reference sequence over a given comparison window. Thus, substantially similar sequences include those having, for example, at least 85% sequence identity, at least 90%, 91%, 92%, 93%, 94%, 95%, 96%, 97%, 98%, or 99% sequence identity. Two sequences that are identical to each other are also substantially similar. The comparison window or the length of comparison sequence will generally be at least the length of the binding domain of a Botulinum toxin or binding domain of Botulinum toxin fragment, e.g., a fragment comprising about 20, 25, 30, 35, 40, 45, 50, 55, 60, 70, 80, 90, 100, 120, 140, 150, 160, 180, 200, 225, 250, 275, 300, 325, 350, 375, 400, 425 contiguous amino acids of the binding domain of a Botulinum toxin. Sequence identity is calculated based on the reference sequence, and algorithms for sequence analysis are known in the art. Thus, to determine percent sequence identity of two amino acid sequences, the sequences are aligned for optimal comparison purposes (e.g., gaps can be introduced in the sequence of one polypeptide for optimal alignment with the other polypeptide). The amino acid residues at corresponding acid positions are then compared. When a position in one sequence is occupied by the same amino acid residue as the corresponding position in the other sequence, then the molecules are identical at that position. The percent sequence identity between the two sequences is a function of the number of identical positions shared by the sequences (i.e., percent sequence identity=numbers of identical positions/total numbers of positions×100). Percent sequence identity between two polypeptide sequences can be determined using the Vector NTI software package (Invitrogen Corp., Carlsbad, Calif.). A gap opening penalty of 10 and a gap extension penalty of 0.1 may be used for determining the percent identity of two polypeptides. All other parameters may be set at the default settings. Another software tool for determining sequence homology is The Basic Local Alignment Search Tool (BLAST) from National Center for Biotechnology Information (NCBI). For example, BLAST can compare protein sequences and calculate the percentage of identical or similar amino acid residues, homology, gaps, etc.

"Peripherally administering" or "peripheral administration" means subdermal, intradermal, transdermal, or subcutaneous administration, but excludes intramuscular administration. "Peripheral" means in a subdermal location, and excludes visceral sites.

"Pharmaceutical composition" means a composition comprising an active pharmaceutical ingredient, such as, for example, a Clostridial toxin active ingredient such as a botulinum toxin, and at least one additional ingredient, such as, for example, a stabilizer or excipient or the like. A pharmaceutical composition is therefore a formulation which is suitable for diagnostic or therapeutic administration to a subject, such as a human patient. The pharmaceutical composition can be, for example, in a lyophilized or vacuum dried condition, a solution formed after reconstitution of the lyophilized or vacuum dried pharmaceutical composition, or as a solution or solid which does not require reconstitution.

"Pharmacologically acceptable excipient" is synonymous with "pharmacological excipient" or "excipient" and refers to any excipient that has substantially no long term or permanent detrimental effect when administered to mammal and encompasses compounds such as, e.g., stabilizing agent, a bulking agent, a cryo-protectant, a lyo-protectant, an additive, a vehicle, a carrier, a diluent, or an auxiliary. An excipient generally is mixed with an active ingredient, or permitted to dilute or enclose the active ingredient and can be a solid, semi-solid, or liquid agent. It is also envisioned that a pharmaceutical composition comprising a Clostridial toxin active ingredient can include one or more pharmaceutically acceptable excipients that facilitate processing of an active ingredient into pharmaceutically acceptable compositions. Insofar as any pharmacologically acceptable excipient is not incompatible with the Clostridial toxin active ingredient, its use in pharmaceutically acceptable compositions is contemplated. Non-limiting examples of pharmacologically acceptable excipients can be found in, e.g., Pharmaceutical Dosage Forms and Drug Delivery Systems (Howard C. Ansel et al., eds., Lippincott Williams & Wilkins Publishers, $7^{th}$ ed. 1999); Remington: The Science and Practice of Pharmacy (Alfonso R. Gennaro ed., Lippincott, Williams & Wilkins, $20^{th}$ ed. 2000); Goodman & Gilman's The Pharmacological Basis of Therapeutics (Joel G. Hardman et al., eds., McGraw-Hill Professional, $10^{th}$ ed. 2001); and Handbook of Pharmaceutical Excipients (Raymond C. Rowe et al., APhA Publications, $4^{th}$ edition 2003), each of which is hereby incorporated by reference in its entirety.

The constituent ingredients of a pharmaceutical composition can be included in a single composition (that is, all the constituent ingredients, except for any required reconstitution fluid, are present at the time of initial compounding of the pharmaceutical composition) or as a two-component system, for example a vacuum-dried composition reconstituted with a reconstitution vehicle which can, for example, contain an ingredient not present in the initial compounding of the pharmaceutical composition. A two-component system can provide several benefits, including that of allowing incorporation of ingredients which are not sufficiently compatible for long-term shelf storage with the first component of the two-component system. For example, the reconstitution vehicle may include a preservative which provides sufficient protection against microbial growth for the use period, for example one-week of refrigerated storage, but is not present during the two-year freezer storage period during which time it might degrade the toxin. Other ingredients, which may not be compatible with a botulinum toxin or other ingredients for long periods of time, can be incorporated in this manner; that is, added in a second vehicle (e.g. in the reconstitution vehicle) at the approximate time of use. A pharmaceutical composition can also include preservative agents such as benzyl alcohol, benzoic acid, phenol, parabens and sorbic acid. Pharmaceutical compositions can include, for example, excipients, such as surface active agents; dispersing agents; inert diluents; granulating and disintegrating agents; binding agents; lubricating agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; antioxidants; stabilizing agents; and pharmaceutically acceptable polymeric or hydrophobic materials and other ingredients known in the art and described, for example in Genaro, ed., 1985, Remington's Pharmaceutical Sciences, Mack Publishing Co., Easton, Pa., which is incorporated herein by reference.

"Polysaccharide" means a polymer of more than two saccharide molecule monomers. The monomers can be identical or different.

"Stabilizing agent", "stabilization agent" or "stabilizer" means a substance that acts to stabilize a Clostridial toxin active ingredient such that the potency of the pharmaceutical composition is increased relative to an unstabilized composition.

"Stabilizers" can include excipients, and can include protein and non-protein molecules.

"Surfactant" refers to a natural or synthetic amphiphilic compound. A surfactant can be non-ionic, zwitterionic, or ionic. Non-limiting examples of surfactants include a poloxamer, a polysorbate, and combinations thereof.

"Therapeutic formulation" means a formulation can be used to treat and thereby alleviate a disorder or a disease, such as, for example, a disorder or a disease characterized by hyperactivity (i.e. seborrhea) of a sebaceous gland.

"Therapeutically effective concentration", "therapeutically effective amount," "effective amount," "effective dose," and "therapeutically effective dose" refer to the minimum dose of a Clostridial toxin active ingredient necessary to achieve the desired therapeutic effect and includes a dose sufficient to reduce a symptom associated with aliment being treated.

"Topical administration" excludes systemic administration of the neurotoxin. In other words, and unlike conventional therapeutic transdermal methods, topical administration of botulinum toxin does not result in significant amounts, such as the majority of, the neurotoxin passing into the circulatory system of the patient.

"Treating" means to alleviate (or to eliminate) at least one symptom of a condition or disorder, such as, for example, wrinkles, laxity, dryness, spottiness, unevenness, redness, large pores, oiliness, or the like, either temporarily or permanently.

"Variant" as used herein refers to a biomolecule (e.g., polypeptide or nucleic acid) whose sequence that differs from that of a parent sequence by virtue of at least one modification or amino acid (or nucleic acid) substitution. Accordingly, variant polypeptides comprise at least one modification or substitution of an amino acid residue. Types of modifications that give raise to variant polypeptides include, e.g., addition, deletion, substitution, transposition, etc. of one or more amino acid residues.

Polypeptides and Compositions Comprising the Polypeptides

As mentioned above, in one aspect, a polypeptide is provided that comprises an amino acid sequence substantially identical to an amino acid sequence in a binding domain, of a Clostridial toxin. In one embodiment, the Clostridial toxin is a botulinum toxin. In some embodiments, the polypeptide comprises an amino acid sequence substantially identical to an amino acid sequence in the full-length of a botulinum toxin which is devoid of toxicity. In one embodiment, the polypeptide comprises an amino acid sequence substantially identical to the amino acid sequence of the full-length of a botulinum toxin which is devoid of toxicity. In some embodiments, the polypeptide comprises an amino acid sequence substantially identical to an amino acid sequence in the heavy chain of the botulinum toxin. In some embodiments, the polypeptide comprises an amino acid sequence substantially identical to an amino acid sequence in the carboxyl or C-terminal segment of the heavy chain of botulinum toxin ($H_C$). In one embodiment, the polypeptide comprises an amino acid sequence substantially identical to an amino acid sequence of the binding domain of the botulinum toxin. In one embodiment, the polypeptide comprises an amino acid sequence identical to the amino acid sequence of the binding domain of the botulinum toxin. In another embodiment, the polypeptide comprises an amino acid sequence substantially identical to an amino acid sequence in the amino or N-terminal half of the binding domain of the botulinum toxin ($H_{CN}$). In one embodiment, the polypeptide comprises an amino acid sequence identical to the N-terminal half of the binding domain of the botulinum toxin. In one embodiment, the botulinum toxin is a BoNT/A. In another embodiment, the botulinum toxin is a mosaic toxin. In one embodiment, the botulinum toxin is BoNT/DC. In alternative embodiments, the botulinum toxin is not a BoNT/A.

In another aspect, a polypeptide comprises a sequence of amino acids having at least 90% sequence identity to a binding domain of a botulinum toxin. In one embodiment, the molecular weight of the polypeptide is between about 1 kDa to about 90 kD, or between about 20 kDa to about 60 kD, or between about 22 kDa to about 50 kD.

The amino acid sequences of the botulinum toxin serotypes and subtypes are known and Table 1 gives approximate boundary regions for translocation, endopeptidase and binding domains, as well as exemplary GENBANK/UNIPROT accession number(s) thereof. Representative serotypes of BoNT toxins, e.g., type A, type B, type $C_1$, type D, type E, type F, type G, including, related members are also disclosed in U.S. Pat. Nos. 7,892,565 and 8,486,422. A potential eighth type ("type H") was described in Dover et al., *J Infect Dis.*, 209(2):192-202, 2014 (PMID: 24106295). Recent reports have variously described this novel neurotoxin as BoNT/H, BoNT/FA or BoNT/HA. See, Maslanka et al., *J Infect Dis.*, 213(3): 379-385, 2016; Peck et al., *Toxins* (Review), 9(1): 38, 2017. Mosaic botulinum toxins are also known, such as BoNT/DC and BoNT/CD.

TABLE 1

| Toxin | ACCESSION # | LC | HN | HC |
|---|---|---|---|---|
| BoNT/A | P0DPI1 | M1-K448 | A449-K871 | N872-L1296 |
| BoNT/B | P10844 | M1-K441 | A442-S858 | E859-E1291 |
| BoNT/$C_1$ | P18640 | M1-K449 | T450-N866 | N867-E1291 |
| BoNT/D | P19321 | M1-R445 | D446-N862 | S863-E1276 |
| BoNT/E | Q00496 | M1-R422 | K423-K845 | R846-K1252 |
| BoNT/F | P30996 | M1-K439 | A440-K864 | K865-E1274 |
| BoNT/G | Q60393 | M1-K446 | S447-S863 | N864-E1297 |
| BoNT/H | KGO15617 | M1-K434 | N435-S843 | Y844-L1288 |
| BoNT/DC | ABP48747 | M1-K500 | V501-K831 | V832-E1285 |
| TeNT | P04958 | M1-A457 | S458-V879 | I880-D1315 |
| BaNT | Q45851 | M1-K431 | N432-I857 | I858-E1268 |
| BuNT | P30995 | M1-R422 | K423-I847 | K848-K1251 |
| eBoNT/J | A0A242DI27 | M1-Q432 | R433-I860 | D861-D1279 |

In one embodiment, the Clostridial toxin is derived from BoNT/A. In an alternate embodiment, the Clostridial toxin is not derived from BoNT/A, e.g., the Clostridial toxin is a Clostridial toxin derived from BoNT/B, BoNT/$C_1$, BoNT/D, BoNT/E, BoNT/F, BoNT/G, BoNT/H, BoNT/DC, BoNT/CD, BoNT/FA, BoNT/HA, BoNT/X, eBoNT/J, TeNT, BaNT, BuNT, or a combination thereof.

In another embodiment, Clostridial toxins are derived from various subtypes of Clostridial toxins. As used herein the term "subtype" may refer to any of two or more functionally similar proteins that have identical or similar amino acid sequences and are either encoded by different genes, or by RNA transcripts from the same gene which have had different exons removed. "Subtype" also may refer to any of the sequences encoding such proteins, including mature and immature sequences. Thus, "subtype" includes the genes encoding one or more of the aforementioned Clostridial toxins, as well as the protein products of the genes, unless stated or otherwise understood by context to refer to only one or the other. At least 40 unique BoNTs, often called subtypes, have been identified by DNA sequencing; some have an impact on BoNT function (Rossetto et al., *Nature Reviews Microbiol.*, 12, 535-49, 2014). For instance, molecular studies have provided evidence for cross-reactive serological observations of a single BoNT containing structural components of BoNT serotypes C and D. See, Arndt et al. (*J Mol Biol.*, 362(4):733-42, 2006) and Hill et al., (*J Bacteriol.*, 189:818-32, 2007). In some instances, sequences of BoNT/F were found to be particularly variable (Raphael et al., *Appl Environ Microbiol.*, 76(14):4805-12, 2012), leading to functional diversity with regard to cleavage of synaptic vesicle membrane proteins such as VAMP-2 (Kalb et al., *Anal Chem.*, 86:3254-62, 2014).

In one embodiment, the Clostridial toxin is derived from various BoNT/A subtypes, such as, e.g., A1, A2, A3, A4, A5, A6, A7, A9, A10; BoNT/B subtypes, such as, e.g., B1, B2, B3, B4, B5, B6, B7, B8, Bnp, and Bbv; BoNT/C subtypes, such as, e.g., C and CD; BoNT/D subtypes, such as, e.g., D and DC; BoNT/E subtypes, such as, e.g., E1, E2, E3, E4, E5, E6, E7, E8, E9; BoNT/F subtypes, such as, e.g., F1, F2, F3, F4, F5, F6, F7; and BoNT/G subtypes, such as, e.g., subtype G. BoNT subtypes include chimeric BoNTs e.g., BoNT/DC, BoNT/CD, BoNT/FA, etc. See, Rossetto et al., *Nature Reviews Microbiol.*, 12, 535-49, 2014; Montecucco et al., *MBio* 6:e02131-14, 2015; U.S. Pat. Nos. 8,841,111 and 8,697,413. Analysis of sequence alignment, for example, performed via software such as VECTOR NTI (Thermo Fisher, Carlsbad, Calif.), reveals a high degree of sequence identity between the individual BoNT/A subtypes. For example, in one embodiment, there is about 78.9% (e.g., between 75%-80%, depending on the alignment software) overall sequence identity and an even greater sequence identity of about 99.3% (e.g., between 95% and 99.9%, depending on the alignment software) at the consensus positions.

In one embodiment, the disclosure relates to homologs of Clostridial toxins. The term "homolog" means a protein in a group of proteins that perform the same biological function, e.g., proteins that belong to the same Clostridial toxin family and that provide a common activity. Homologs are generally expressed by homologous genes. With reference to homologous genes, homologs include orthologs, e.g., genes expressed in different species that evolved from a common ancestral gene by speciation and encode proteins retain the same function, but do not include paralogs, e.g., genes that are related by duplication but have evolved to encode proteins with different functions. Homologous genes include naturally occurring alleles and artificially-created variants. Degeneracy of the genetic code provides the possibility to substitute at least one base of the protein encoding sequence of a gene with a different base without causing the amino acid sequence of the polypeptide produced from the gene to be changed. When optimally aligned, homolog proteins have typically at least about 50%, about 55%, about 60%, about 65%, about 70%, about 75%, about 80%, about 85%, about 90%, about 92%, about 94%, about 95%, about 96%, about 97%, about 98%, about 99%, about 99.5% or greater % identity or similarity compared to a subject protein, e.g., BoNT/A1 or a fragment thereof comprising the $H_C$ domain, particularly the $H_{CN}$ domain, especially the N-terminal half of the H$_{CN}$ domain. In another aspect of the disclosure homolog proteins have an amino acid sequences that have at least about 50%, about 55%, about 60%, about 65%, about 70%, about 75%, about 80%, about 85%, about 90% or greater % identity or similarity to the polypeptides of SEQ ID NO: 1, SEQ ID NO: 19, SEQ ID NOs: 3-5, SEQ ID NO: 6, SEQ ID NO: 20, SEQ ID Nos: 7-10, SEQ ID NO: 11, SEQ ID NO: 21, SEQ ID NOs: 12-18 and SEQ ID NOs: 25-27.

In one embodiment, homologous Clostridial toxins are grouped on the basis of percent homology, which is defined as the percent of either identical or similar residues (consensus) within a protein sequence relative to a reference protein sequence, divided by the length of the reference sequence, after aligning the sequences and introducing gaps, if necessary, to achieve the maximum percent sequence homology. Consensus substitutions are those substitutions that allow an amino acid to be substituted with a similar amino acid. Amino acids can be similar in several characteristics, for example, size, shape, hydrophobicity, hydrophilicity, charge, isoelectric point, polarity, aromaticity, etc. Alignment for purposes of determining percent amino acid sequence homology can be achieved in various ways that are within the ordinary skill of those persons of skill in the art. In some cases, amino acid sequences can be aligned using publicly available computer software such as BLAST, BLAST-2, ALIGN or MEGALIGN (DNASTAR) software. In one embodiment, the percent homology is computed using Basic Local Alignment Search Tool (BLAST) available via the NCBI, which conducts a pairwise alignment and provides a raw score using the matrix of residue substitution. Herein, the bit score computed by BLAST is a normalized score which considered the sequence length and gap size. As is understood in bioinformatics, a score of 283 bits means to find a better alignment than what is presented, the search would have to encompass a space of $2^{283}$ (or $2 \times 10^{85}$) units (e.g., amino acids or nucleic acids). Thus, the higher the bit score, the more highly significant the match. Those skilled in the art can determine appropriate parameters for measuring alignment, including any algorithms needed to achieve maximal alignment over the full length of the sequences being compared. Sequence homology is then calculated relative to the longer sequence, i.e., even if a shorter sequence shows 100% sequence identity with a portion of a longer sequence, the overall sequence identity will be less than 100%.

Under an alternate embodiment, the variant Clostridial toxin may comprise a sequence which shares at least about 30%, 35%, 40%, 45%, 50%, 55%, 60%, 65%, 70%, 75%, 80%, 85%, 90%, 95%, 96%, 97%, 98%, 99%, or greater degree of identity to one or more of the aforementioned Clostridial toxins. For example, in one embodiment, variant Clostridial toxins may comprise at least about 50%, 55%, 60%, 65%, 70%, 75%, 80%, 85%, 90%, 95%, 96%, 97%, 98%, 99%, or greater, e.g., about 99.9%, sequence identity to the amino acid sequence set forth in UNIPROT Accession Nos. P0DPI1 (e.g., type A); P10844 (e.g., type B); P18640 (e.g., type C$_1$); P19321 (e.g., type D); Q00496 (GENBANK #CAA44558) (e.g., type E); P30996 (e.g., type F); Q60393 (e.g., type G); GENBANK ID: KGO15617 (UNIPARC ID: 00052C1529) for type H; GENBANK ID: BAQ12790 (UNIPARC ID: 0005822796) for type X; UNIPROT Accession Nos. P04958 (e.g., TeNT); Q45851 (e.g., BaNT); or P30995 (e.g., BuNT).

In another embodiment, variant Clostridial toxins may comprise at least about 30%, 40%, 50%, 55%, 60%, 65%, 70%, 75%, 80%, 85%, 90%, 95%, 96%, 97%, 98%, 99%, or greater, e.g., about 99.9%, sequence identity to the nucleic acid or amino acid sequence set forth in (a) GENBANK Accession Nos. AF488749 (nucleic acid) and AAQ06331 (protein) for toxins derived from BoNT/A; (b) GENBANK Accession Nos. AB232927 (nucleic acid) or BAE48264 (protein) for toxins derived from BoNT/B; (c) GENBANK # CAA47060 (nucleic acid); UNIPROT #P18640 (protein) for toxins derived from BoNT/C1; (d) GENBANK # X54254 (nucleic acid); UNIPROT # P19321 (protein) for toxins derived from BoNT/D; (e) GENBANK # EF378947 (nucleic acid); ABP48747 (protein) for toxins derived from BoNT/DC; (f) GENBANK #JX424539 (nucleic acid); AFV91344 (protein) for toxins derived from BoNT/E; (g) GENBANK # ABS41202 (protein); DNA (e.g., cDNA) encoding ABS41202 for toxins derived from BoNT/F; (h) GENBANK # X74162 (nucleic acid); UNIPROT # Q60393 (protein) for toxins derived from BoNT/G; (i) GENBANK ID: BAQ12790 (protein) for toxins derived from BoNT/X; or (j) GENBANK # OTO22244; UNIPROT # A0A242DI27 (protein) for toxins derived from eBoNT/J.

In yet another embodiment, variant Clostridial toxins may comprise at least about 30%, 40%, 50%, 55%, 60%, 65%, 70%, 75%, 80%, 85%, 90%, 95%, 96%, 97%, 98%, 99%, or greater, e.g., about 99.9%, sequence identity to the nucleic acid or amino acid sequence set forth in (1) GENBANK # AB443580 (nucleic acid); BAH03558 (protein) for a toxin derived from BoNT/A2 Chiba strain; (b) GENBANK # X73423 (nucleic acid); CAA51824 (protein)) for toxins derived from Kyoto-F strain; (c) GENBANK # DQ185900 (nucleic acid); ABA29017 (protein) for toxins derived from BoNT/A3 Loch Maree strain; (d) (GENBANK # EU341307 (nucleic acid); ABY56338 (protein)) for toxins derived from BoNT/A4 657Ba strain; (e) (GENBANK #HM153705 (nucleic acid); ADJ68235 (protein) for toxins derived from BoNT/A5A 661222 strain; (f) GENBANK # FJ981696 (nucleic acid); ACW83602 (protein) for toxins derived from BoNT/A6 CDC41370 strain; GENBANK # JQ954969 (nucleic acid); AFV13854 (protein) for toxins derived from BoNT/A7 2008-148 strain.

In some embodiments, the variant Clostridial toxins include mutant Clostridial toxins or a fragment thereof. Typically, mutant Clostridial toxins comprise at least 1, 2, 3, 4, 5, or more, e.g., up to 10 mutations in a core Clostridial toxin polypeptide sequence or a fragment thereof, e.g., full-length BoNT/A sequence or the H$_C$ fragment of SEQ ID NO: 1. Representative examples of such mutant Clostridial toxins include, e.g., a first BoNT/A mutant comprising W1266L and Y1267S or a fragment thereof (e.g., a H$_C$ fragment of the BoNT/A mutant comprising W391L and Y392S in SEQ ID NO: 1; mutant sequence set forth in SEQ ID NO: 26) or a second BoNT/A mutant comprising T1145A and T1146A or a fragment thereof (e.g., a H$_C$ fragment of the BoNT/A mutant comprising T270A and T271A in SEQ ID NO: 1; mutant sequence set forth in SEQ ID NO: 25) or a third BoNT/A mutant comprising G1292R or a fragment thereof (e.g., a H$_C$ fragment of the BoNT/A mutant comprising G417R in SEQ ID NO: 1; mutant sequence set forth in SEQ ID NO: 27). In some embodiments, the mutant polypeptides or fragments thereof have modulated, e.g., diminished, in vitro or in vivo activity compared to the non-muted Clostridial toxins or fragments thereof and the mutant polypeptides may therefore be used to modulate the pharmacological properties of the non-muted Clostridial toxins or fragments thereof.

Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the art and from the teaching herein.

In one embodiment, the variant Clostridial toxin comprises one or more amino acid substitutions, which are selected so as to preserve activity of the variant Clostridial toxin. Residues that are semi-conserved may tolerate changes that preserve charge, polarity, and/or size. For example, a variant Clostridial toxin comprising the amino acid sequence set forth in the aforementioned accessioned UNIPROT and/or GENBANK sequences may have one or more substitutions, wherein the substituted amino acid may be any one of the known 20 amino acids, wherein the variant Clostridial toxin maintains its activity, e.g., cell-binding activity or cell-signaling activity or a combination thereof (see Examples section). Preferably, the amino acids are substituted in a conserved or semi-conserved manner. Exemplary types of conserved amino acid substitutions include, e.g., a substitution of a non-polar (hydrophobic) residue for another non-polar (hydrophobic) residue such as I, V, L or M for one another, a substitution of one polar (hydrophilic), non-charged residue for another polar, non-charged residue such as Q for N, G for S, or vice versa, or a substitution of a charged residue for another similarly charged residue such as K, R or H for one another, or D for E or vice versa. On the other hand, non-conservative substitutions include the substitution of a non-polar (hydrophobic) residue such as I, V, L, A, M for a polar (hydrophilic) residue such as C, Q, D, K and/or vice versa. In one embodiment, the term "conserved substitution" indicates an amino acid substitution within one of the following "strong" groups: STA, NEQK, NHQK, NDEQ, QHRK, MILV, MILF, HY, and/or FYW; and the term "semi-conserved substitution" indicates an amino acid substitution within one of the following "weak" groups: CSA, ATV, SAG, STNK, STPA, SGND, SNDEQK, NDEQHK, NEQHRK, FVLIM, and/or HFY. Methods of making conserved or semi-conserved amino acid substitutions are known in the art, e.g., Risler et al., *J. Mol. Biol.*, 204:1019-1029, 1988; Niefind et al., *J. Mol. Biol.* 219:481-497, 1991; and Overington et al. *Protein Science*, 1:216-226, 1992. Exemplary types of conserved and semi-conserved amino acid substitutions in the core Clostridial toxin sequence (e.g., BoNT/A sequence) are observable via a CLUSTAL multiple sequence alignment, wherein the asterisk (*) indicates identity, the semicolon (:) indicates conserved substitution and the period (.) indicates a semi-conserved substitution.

Clostridial toxin variants of the present disclosure may be a naturally-occurring variant or a non-naturally-occurring variant. As used herein, the term "naturally occurring Clostridial toxin variant" refers to any Clostridial toxin produced without the aid of any human manipulation, including, without limitation, Clostridial toxin isoforms produced from alternatively-spliced transcripts, Clostridial toxin isoforms produced by spontaneous mutation and Clostridial toxin subtypes. As used herein, the term "non-naturally occurring Clostridial toxin variant" refers to any Clostridial toxin produced with the aid of human manipulation, including, without limitation, Clostridial toxins produced by genetic engineering using random mutagenesis or rational design and Clostridial toxins produced by chemical synthesis. Non-limiting examples of non-naturally occurring Clostridial toxin variants include, e.g., conservative Clostridial toxin variants, non-conservative Clostridial toxin variants, and active Clostridial toxin fragments. Non-natural Clostridial toxins further include natural Clostridial toxins that have been post-translationally modified, e.g., via addition of chemical moieties, tags, ligands, and the like.

As used herein, the term "conservative Clostridial toxin variant" refers to a Clostridial toxin that has at least one amino acid substituted by another amino acid or an amino acid analog that has at least one property similar to that of the original amino acid from the reference Clostridial toxin sequence (see, e.g., Table 1). Examples of such properties include, without limitation, similar size, topography, charge, hydrophobicity, hydrophilicity, lipophilicity, covalent-bonding capacity, hydrogen-bonding capacity, a physicochemical property, of the like, or any combination thereof. A conservative Clostridial toxin variant can function in substantially the same manner as the reference Clostridial toxin on which the conservative Clostridial toxin variant is based, and can be substituted for the reference Clostridial toxin in any aspect of the present specification. A conservative Clostridial toxin variant may substitute 1, 2, 3, 4, 5, 10, 20, 30, 40, 50, 75, 100, 200, 300, 400, or 500 or more amino acids from the reference Clostridial toxin on which the conservative Clostridial toxin variant is based. A conservative Clostridial toxin variant can also substitute at least 5, 10, 15, 20, or 25 contiguous amino acids from the reference Clostridial toxin on which the conservative Clostridial toxin variant is based. Non-limiting examples of a conservative Clostridial toxin variant include, e.g., conservative BoNT/A variants, conservative BoNT/B variants, conservative BoNT/C$_1$ variants, conservative BoNT/D variants, conservative BoNT/E variants, conservative BoNT/F variants, conservative BoNT/G variants, conservative BoNT/H variants, conservative BoNT/X variants, conservative eBoNT/J variants, conservative TeNT variants, conservative BaNT variants and conservative BuNT variants.

As used herein, the term "non-conservative Clostridial toxin variant" refers to a Clostridial toxin in which (a) at least one amino acid is deleted from the reference Clostridial toxin on which the non-conservative Clostridial toxin variant is based; (b) at least one amino acid added to the reference Clostridial toxin on which the non-conservative Clostridial toxin is based; or (c) at least one amino acid is substituted by another amino acid or an amino acid analog that does not share any property similar to that of the original amino acid from the reference Clostridial toxin sequence (see, e.g., Table 1). A non-conservative Clostridial toxin variant can function in substantially the same manner as the reference Clostridial toxin on which the non-conservative Clostridial toxin variant is based, and can be substituted for the reference Clostridial toxin in any aspect of the present specification. A non-conservative Clostridial toxin variant can delete one or more amino acids, two or more amino acids, three or more amino acids, four or more amino acids, five or more amino acids, and ten or more amino acids from the reference Clostridial toxin on which the non-conservative Clostridial toxin variant is based. A non-conservative Clostridial toxin variant can add one or more amino acids, two or more amino acids, three or more amino acids, four or more amino acids, five or more amino acids, and ten or more amino acids to the reference Clostridial toxin on which the non-conservative Clostridial toxin variant is based. A non-conservative Clostridial toxin variant may substitute 1, 2, 3, 4, 5, 10, 20, 30, 40, 50, 75, 100, 200, 300, 400, or 500 or more amino acids from the reference Clostridial toxin on which the non-conservative Clostridial toxin variant is based. A non-conservative Clostridial toxin variant can also substitute at least 5, 10, 15, 20, or 25 contiguous amino acids from the reference Clostridial toxin on which the non-conservative Clostridial toxin variant is based. Non-limiting examples of a non-conservative Clostridial toxin variant include, e.g., non-conservative BoNT/A variants, non-conservative BoNT/B variants, non-conservative BoNT/C₁ variants, non-conservative BoNT/D variants, non-conservative BoNT/E variants, non-conservative BoNT/F variants, non-conservative BoNT/G variants, non-conservative BoNT/H variants, non-conservative BoNT/X variants, non-conservative eBoNT/J variants, non-conservative TeNT variants, non-conservative BaNT variants and non-conservative BuNT variants. It is also envisioned that any of a variety of Clostridial toxin fragments can be useful in aspects of the present specification with the proviso that these active fragments can execute the overall cellular mechanism whereby a Clostridial toxin binds to a binding partner, e.g., synaptic vesicle glycoprotein. Thus, aspects of this embodiment can include Clostridial toxin fragments having a length of, e.g., at least 600, 700, 800, 900, 1000, 1100, or at least 1200 amino acids. Other aspects of this embodiment, can include Clostridial toxin fragments having a length of, e.g., at most 600, 700, 800, 900, 1000, 1100, or at most 1200 amino acids.

Embodiments of the disclosure further relate to variant Clostridial toxin polypeptides. As used herein, the term "polypeptide" includes a molecule comprising a linear chain or branched amino acids, peptidomimetics, as well as pharmaceutically acceptable salts thereof. Typically, a polypeptide comprises a plurality of amino acid residues, e.g., 2, 5, 10, 25, 50, 75, 100, 150, 200, 250, 300, 350, 400, 450, 500, or more amino acid residues which are bonded to each other via covalent bonds, e.g., a peptide bond. "Amino acid residue" means the individual amino acid units incorporated into the polypeptides of the disclosure. As used herein, the term "amino acid" means a naturally occurring or synthetic amino acid, as well as amino acid analogs, stereoisomers, and amino acid mimetics that function similarly to the naturally occurring amino acids. Included by this definition are natural amino acids such as: (1) histidine (His; H) (2) isoleucine (Ile; I) (3) leucine (Leu; L) (4) Lysine (Lys; K) (5) methionine (Met; M) (6) phenylalanine (Phe; F) (7) threonine (Thr; T) (8) tryptophan (Trp; W) (9) valine (Val; V) (10) arginine (Arg; R) (11) cysteine (Cys; C) (12) glutamine (Gln; Q) (13) glycine (Gly; G) (14) proline (Pro; P) (15) serine (Ser; S) (16) tyrosine (Tyr; Y) (17) alanine (Ala; A) (18) asparagine (Asn; N) (19) aspartic acid (Asp; D) (20) glutamic acid (Glu; E) (21) selenocysteine (Sec; U); including unnatural amino acids: (a) citrulline (Cit); (b) cystine; (c) gama-amino butyric acid (GABA); (d) ornithine (Orn); (f) theanine; (g) homocysteine (Hey); (h) thyroxine (Thx); and amino acid derivatives such as betaine; carnitine; carnosine creatine; hydroxytryptophan; hydroxyproline (Hyp); N-acetyl cysteine; S-Adenosyl methionine (SAM-e); taurine; tyramine.

In one embodiment, the Clostridial toxin comprises derivatives of parent Clostridial toxins, e.g., derivatives of the amino acid sequence set forth in UNIPROT Accession Nos. P0DPI1 (e.g., type A); P10844 (e.g., type B); P18640 (e.g., type C₁); P19321 (e.g., type D); Q00496 (GENBANK #CAA44558) (e.g., type E); P30996 (e.g., type F); Q60393 (e.g., type G); GENBANK ID: KGO15617 (UNIPARC ID: 00052C1529) for type H; GENBANK ID: BAQ12790 (UNIPARC ID: 0005822796) for type X; UNIPROT Accession Nos. P04958 (e.g., TeNT); Q45851 (e.g., BaNT); or P30995 (e.g., BuNT). As used herein, the term "derivative" includes salts, amides, esters, acids, bases, solvates, hydrates, polymorphs or prodrugs of the individual amino acids or the aforementioned polypeptides, including fragments thereof. Such derivatives may be readily prepared by those of skill in this art using known methods for such derivatization. The derivatives suitable for use in the methods described herein may be administered to animals or humans without substantial toxic effects and either are biologically active or are prodrugs.

In one example, the derivatives comprise salts of the amino acids or the toxin polypeptides. The term "salt" includes salts derived from any suitable of organic and inorganic counter ions well known in the art and include, by way of example, hydrochloric acid salt or a hydrobromic acid salt or an alkaline or an acidic salt of the aforementioned amino acids.

If desired, the derivative can, in addition or alternatively, be a solvent addition forms, e.g., a solvate or alcoholate. Solvates contain either stoichiometric or non-stoichiometric amounts of a solvent, and may be formed during the process of crystallization with acceptable solvents such as water, ethanol, and the like. Hydrates are formed when the solvent is water; alcoholates are formed when the solvent is alcohol. Solvates of compounds described herein can be conveniently prepared or formed using routine techniques.

In another embodiment, disclosed herein are polymorphs of Clostridial toxins. Polymorphs refer to alternate crystal forms of the Clostridial toxins described herein. Polymorphic purity of protein (or a polypeptide) samples can be checked using techniques such as powder X-ray diffraction, IR/Raman spectroscopy, and utilizing the differences in their optical properties in some cases (Thomas et al., *Chemical Communications*, 48: 10559-10561 (2012)).

The derivative can further comprise amides or esters of the amino acids and/or isomers (e.g., tautomers or stereoisomers) of the amino acids, as desired.

Domains

Embodiments of the disclosure further relate to domains and sites present in the aforementioned Clostridial toxins, e.g., the translocation domain ($H_N$), the endopeptidase domain, or the cell-binding domain, including, including sub-domains thereof, e.g., $H_{CN}$ sub-domain or $H_{CC}$ subdomain. In one embodiment, the disclosure relates to a polypeptide comprising a cell-binding site located within one or more domains or subdomains in the Clostridial toxin. Such polypeptides can comprise, e.g., one or more amino acid motifs of Clostridial toxin cell-binding domains. Boundary regions for each domain and subdomain found in exemplary Clostridial toxins are disclosed for example in U.S. Pat. No. 8,697,413, incorporated entirely herein by reference. Boundary regions of various domains may be approximated using art-known bioinformatics tools (e.g., INTERPRO or PROSITE). Accordingly, the boundary regions as disclosed in the '413 patent are not absolute and minor variations, e.g., a difference of 1, 2, 3, 4, 5, 7, 10, 15, 20, or more amino acids, each representing a change of less than about 5%, about 4%, about 3%, about 2%, about 1% or a smaller % in the length and/or the molecular weight of the individual domains, is permissible, as disclosed for example in U.S. Pat. Nos. 8,841,111 and 8,512,992, incorporated entirely herein by reference.

The binding activity of the Clostridial toxin or fragments thereof may be assayed using routine techniques, e.g., radio-labeled assay, competitive binding assay, in vitro binding assays such as BIAcore Surface Plasmon (SPR) technology, receptor phosphorylation, dimerization or signaling assay, etc. A representative assay for assessing the biological activity of a polypeptide corresponding to a Clostridial toxin fragment, comprising, e.g., assessing modulation in gene expression mediated by Clostridial toxin variants, comprising, detecting a level of plurality of genes described in the Examples section. In another embodiment, biological activity can be assessed functionally, e.g., via measurement of fibronectin synthesis and/or effect on a target cell such as fibroblasts, keratinocytes, melanocytes, adipocytes, neurons, etc. A representative method involving microscopic evaluation of the morphology of target cells such as fibroblasts is provided in the Examples.

In one embodiment, the biologically active fragments comprise at least 100, 300, 500, 600, 800, 1000, 1200 or more contiguous amino acids of the Clostridial toxin. Fragments of the Clostridial toxins described herein can be generated by methods known to those skilled in the art (e.g., recombinant biotechnological techniques). Fragment polypeptides may be detected using art-known methods (e.g., immunogenic techniques such as immunoblotting or ELISA or protein staining techniques such as silver staining).

In certain embodiments, the fragment polypeptides may be secreted when expressed in a suitable host, e.g., baculovirus, *E. coli*, yeast, insect cell, or mammalian cells. As used herein, "secreted" means that the expressed polypeptide is secreted from the host cell into the culture medium at a level that is detectable using a conventional technique, e.g., ELISA assay. Methods for synthesizing proteins in secretory forms are known in the art. In one embodiment, the disclosure relates to Clostridial toxin fragments comprising the carboxy terminal regions of the heavy chains ($H_C$ regions) comprising a Clostridial toxin binding domain, which upon binding to a receptor complex located at the surface of a target cell and modulates gene expression and/or metabolic activity of the target cell. The $H_C$ regions from the heavy chains of Clostridial toxins are approximately 400-440 amino acids in length and comprise a binding domain (Table 1). Thus, aspects of this embodiment can include Clostridial toxin $H_C$ regions comprising a binding domain having a length of, e.g., at least 20, 30, 40, 50, 75, 100, 125, 150, 175, 200, 225, 250, 275, 300, 325, 350, 375, 400, or 425 amino acids. Other aspects of this embodiment can include Clostridial toxin $H_C$ regions comprising a binding domain having a length of, e.g., at most 20, 30, 40, 50, 75, 100, 125, 150, 175, 200, 225, 250, 275, 300, 325, 350, 375, 400, or 425 amino acids.

In one embodiment, the disclosure relates to the following binding domain fragments: amino acids N872-L1296 of BoNT/A (e.g., UNIPROT # P0DPI1); amino acids E859-E1291 of BoNT/B (e.g., UNIPROT #P10844); amino acids N867-E1291 of BoNT/$C_1$ (e.g., UNIPROT #P18640); amino acids S863-E1276 of BoNT/D (e.g., UNIPROT #P19321); amino acids R846-K1252 of BoNT/E (e.g., UNIPROT #Q00496 or GENBANK #CAA44558); amino acids K865-E1274 of BoNT/F (e.g., UNIPROT #P30996); amino acids N864-E1297 of BoNT/G (e.g., UNIPROT #Q60393); amino acids Y844-L1288 of BoNT/H (e.g., GENBANK #KGO15617); amino acids I880-D1315 of TeNT (e.g., UNIPROT #P04958); amino acids I858-E1268 of BaNT (e.g., UNIPROT #Q45851); or amino acids K848-K1251 of BuNT (e.g., UNIPROT #P30995).

In another embodiment, the disclosure relates to a polypeptide comprising an amino acid sequence substantially identical to an amino acid sequence of the full-length botulinum toxin which is devoid of toxicity. In one embodiment, the polypeptide comprises a sequence of amino acids having at least 90% sequence identity to the full-length of a botulinum toxin which is devoid of toxicity.

In another embodiment, the polypeptide comprises an amino acid sequence substantially identical to an amino acid sequence of the carboxyl or C-terminal segment of the heavy chain of botulinum toxin ($H_C$). In one embodiment, the polypeptide comprises an amino acid sequence having at least 90% sequence identity to the C-terminal segment of the heavy chain of a botulinum toxin. In one embodiment, the polypeptide comprises an amino acid sequence substantially identical to an amino acid sequence of the binding domain of the botulinum toxin. In one embodiment, the polypeptide comprises an amino acid sequence having at least 90% sequence identity to a binding domain of a botulinum toxin. In one embodiment, the polypeptide comprises an amino acid sequence substantially identical to an amino acid sequence of the N-terminal half of a binding domain of a botulinum toxin. In one embodiment, the polypeptide comprises an amino acid sequence having at least 90% sequence identity to the N-terminal half of a binding domain of a botulinum toxin.

In some embodiments, the botulinum toxin is selected from the group consisting of Botulinum toxin serotype A (BoNT/A), Botulinum toxin serotype B (BoNT/B), Botulinum toxin serotype $C_1$ (BoNT/$C_1$), Botulinum toxin serotype D (BoNT/D), Botulinum toxin serotype E (BoNT/E), Botulinum toxin serotype F (BoNT/F), Botulinum toxin serotype G (BoNT/G), Botulinum toxin serotype H (BoNT/H), Botulinum toxin serotype X (BoNT/X), *Enterococcus* sp. BoNT/J (eBoNT/J), and mosaic Botulinum toxins and/or variants thereof. Examples of mosaic toxins include BoNT/DC, BoNT/CD, and BoNT/FA. In one embodiment, the botulinum toxin is not Botulinum toxin serotype A (BoNT/A).

In another embodiment, the disclosure relates to Clostridial toxins fragments having an average molecular weight in the range of, e.g., about 1 kDa to about 160 kDa, about 5 kDa to about 160 kDa, about 20 kDa to about 150 kDa, about 40 kDa to about 120 kDa, about 50 kDa to about 80 kDa, about 5 kDa to about 15 kDa, about 10 kDa to about 20 kDa, about 20 kDa to about 30 kDa, about 30 kDa to about 40 kDa, about 40 kDa to about 50 kDa, about 50 kDa to about 60 kDa, about 60 kDa to about 70 kDa, about 70 kDa to about 80 kDa, about 80 kDa to about 90 kDa, about 90 kDa to about 100 kDa, about 100 kDa to about 110 kDa, about 110 kDa to about 120 kDa, about 120 kDa to about 130 kDa, about 130 kDa to about 140 kDa, about 140 kDa to about 150 kDa, or more, including all values in between, e.g., about 1 kDa, 2 kDa, 3 kDa, 4 kDa, 5 kDa, 6 kDa, 7 kDa, 8 kDa, 9 kDa, 10 kDa, 11 kDa, 12 kDa, 13 kDa, 14 kDa, 15 kDa, 16 kDa, 17 kDa, 18 kDa, 19 kDa, 20 kDa, 21 kDa, 22 kDa, 23 kDa, 24 kDa, 25 kDa, 26 kDa, 27 kDa, 28 kDa, 29 kDa, 30 kDa, 31 kDa, 32 kDa, 33 kDa, 34 kDa, 35 kDa, 36 kDa, 37 kDa, 38 kDa, 39 kDa, 40 kDa, 41 kDa, 42 kDa, 43 kDa, 44 kDa, 45 kDa, 46 kDa, 47 kDa, 48 kDa, 49 kDa, 50 kDa, 51 kDa, 52 kDa, 53 kDa, 54 kDa, 55 kDa, 56 kDa, 57 kDa, 58 kDa, 59 kDa, 60 kDa, 61 kDa, 62 kDa, 63 kDa, 64 kDa, 65 kDa, 66 kDa, 67 kDa, 68 kDa, 69 kDa, 70 kDa, 71 kDa, 72 kDa, 173 kDa, 74 kDa, 75 kDa, 76 kDa, 77 kDa, 78 kDa, 79 kDa, 80 kDa, 81 kDa, 82 kDa, 83 kDa, 84 kDa, 85 kDa, 86 kDa, 87 kDa, 88 kDa, 89 kDa, 90 kDa, 91 kDa, 92 kDa, 93 kDa, 94 kDa, 95 kDa, 96 kDa, 97 kDa, 98 kDa, 99 kDa, 100 kDa, 101 kDa, 102 kDa, 103 kDa, 104 kDa, 105 kDa, 106 kDa, 107 kDa, 108 kDa, 109 kDa, 110 kDa, 111 kDa, 112 kDa, 113 kDa, 114 kDa, 115 kDa, 116 kDa, 117 kDa, 118 kDa, 119 kDa, 120 kDa, 121 kDa, 122 kDa, 123 kDa, 124 kDa, 125 kDa, 126 kDa, 127 kDa, 128 kDa, 129 kDa, 130 kDa, 131 kDa, 132 kDa, 133 kDa, 134 kDa, 135 kDa, 136 kDa, 137 kDa, 138 kDa, 139 kDa, 140 kDa, 141 kDa, 142 kDa, 143 kDa, 144 kDa, 145 kDa, 146 kDa, 147 kDa, 148 kDa, 149 kDa, 150 kDa, or more, e.g., to about 155 kDa, about 160 kDa, about 165 kDa, about 170 kDa, about 175 kDa, about 180 kDa, about 190 kDa, about 200 kDa, about 225 kDa, about 250 kDa, about 275 kDa or more. In one embodiment, the disclosure relates to an N-terminal sub-domain ($H_{CN}$) of the binding domain of a Clostridial toxin having molecular weight in the range of, e.g., about 1 kDa to about 50 kDa, about 5 kDa to about 35 kDa, about 10 kDa to about 30 kDa, about 15 kDa to about 25 kDa, about 5 kDa to about 15 kDa, about 5 kDa to about 10 kDa, about 10 kDa to about 20 kDa, about 10 kDa to about 15 kDa, about 20 kDa to about 30 kDa, about 20 kDa to about 25 kDa, or more than 50 kDa, including all values in between, e.g., about 1 kDa, 2 kDa, 3 kDa, 4 kDa, 5 kDa, 6 kDa, 7 kDa, 8 kDa, 9 kDa, 10 kDa, 11 kDa, 12 kDa, 13 kDa, 14 kDa, 15 kDa, 16 kDa, 17 kDa, 18 kDa, 19 kDa, 20 kDa, 21 kDa, 22 kDa, 23 kDa, 24 kDa, 25 kDa, 26 kDa, 27 kDa, 28 kDa, 29 kDa, 30 kDa, 31 kDa, 32 kDa, 33 kDa, 34 kDa, 35 kDa, 36 kDa, 37 kDa, 38 kDa, 39 kDa, 40 kDa, 41 kDa, 42 kDa, 43 kDa, 44 kDa, 45 kDa, 46 kDa, 47 kDa, 48 kDa, 49 kDa, 50 kDa, or more. In one embodiment, the disclosure relates to a polypeptide comprising an amino acid sequence substantially identical to the amino or N-terminal half of the binding domain of the botulinum toxin ($H_{CN}$). In another embodiment, the disclosure relates to a polypeptide comprising an amino acid sequence substantially identical to an amino-terminal (N-terminal) half of the binding domain of a Clostridial toxin comprising the first 10, 20, 30, 40, 50, 60, 70, 80, 90, 100, 110, 120, 140, 150, 160, 170, 180, 190, 200, 210, 220, 230, 240, 250 or a greater number of contiguous amino acids from the N-terminal half of the binding domain of Clostridial toxins. In such embodiments, the polypeptide may have a molecular weight in the range of, e.g., about 1 kDa to about 25 kDa, about 5 kDa to about 20 kDa, about 6 kDa to about 15 kDa, about 8 kDa to about 15 kDa, about 8 kDa to about 14 kDa, about 6 kDa to about 25 kDa, about 8 kDa to about 20 kDa, about 10 kDa to about 15 kDa, including all values in between, e.g., about 1 kDa, 2 kDa, 3 kDa, 4 kDa, 5 kDa, 5.5 kDa, 6 kDa, 6.5 kDa, 7 kDa, 7.5 kDa, 8 kDa, 8.5 kDa, 9 kDa, 9.5 kDa, 10 kDa, 10.5 kDa, 11 kDa, 11.5 kDa, 12 kDa, 12.5 kDa, 13 kDa, 13.5 kDa, 14 kDa, 14.5 kDa, 15 kDa, 15.5 kDa, 16 kDa, 16.5 kDa, 17 kDa, 17.5 kDa, 18 kDa, 19 kDa, 20 kDa, or more.

In a related embodiment, the disclosure relates to a polypeptide comprising an amino acid sequence substantially identical to the C-terminal sub-domain ($H_{CC}$) of the binding domain of a Clostridial toxin having molecular weight in the range of, e.g., about 1 kDa to about 50 kDa, about 5 kDa to about 35 kDa, about 10 kDa to about 30 kDa, about 15 kDa to about 25 kDa, about 5 kDa to about 15 kDa, about 5 kDa to about 10 kDa, about 10 kDa to about 20 kDa, about 10 kDa to about 15 kDa, about 20 kDa to about 30 kDa, about 20 kDa to about 25 kDa, or more than 50 kDa, including all values in between, e.g., about 1 kDa, 2 kDa, 3 kDa, 4 kDa, 5 kDa, 6 kDa, 7 kDa, 8 kDa, 9 kDa, 10 kDa, 11 kDa, 12 kDa, 13 kDa, 14 kDa, 15 kDa, 16 kDa, 17 kDa, 18 kDa, 19 kDa, 20 kDa, 21 kDa, 22 kDa, 23 kDa, 24 kDa, 25 kDa, 26 kDa, 27 kDa, 28 kDa, 29 kDa, 30 kDa, 31 kDa, 32 kDa, 33 kDa, 34 kDa, 35 kDa, 36 kDa, 37 kDa, 38 kDa, 39 kDa, 40 kDa, 41 kDa, 42 kDa, 43 kDa, 44 kDa, 45 kDa, 46 kDa, 47 kDa, 48 kDa, 49 kDa, 50 kDa, or more.

In another embodiment, the present disclosure provides for Clostridial toxins fragments having the aforementioned molecular weights, e.g., between about 1 kDa to about 150 kDa, particularly between about 5 kDa to about 90 kDa, especially between about 10 kDa to about 70 kDa, as determined by reducing gel electrophoresis.

In other embodiment, the molecular weight of the Clostridial toxins, including fragments thereof, are theoretically computed using art-known bioinformatics tools (e.g., PROTPARAM or COMPUTE pI/MW). For instance, based on PROTPARAM, the full-length BoNT/A (UNIPROT # P0DPI1) has a theoretical molecular weight of about 149.3 kDa, while the $H_C$ domain comprising amino acids 449 to 1296 (848 amino acids) has a theoretical MW of about 98.2 kDa. In a particular embodiment, an $H_{CN}$ domain of BoNT/A (UNIPROT # P0DPI19) spanning amino acids 873 to 1092 has a theoretical molecular weight of about 26.1 kDa based on PROTPARAM. Still in a further embodiment, the proximal N-terminal fragment of an $H_{CN}$ domain of BoNT/A (UNIPROT # P0DPI1) spanning amino acids 873 to 980 has a theoretical molecular weight of about 12.65 kDa.

Representative amino acid sequences of the BoNT $H_C$ domains and $H_{CN}$ domains derived from various serotypes of BoNT, which were used in the sequence alignment analysis for the identification of identical and consensus sequences, are identified herein as SEQ ID NOs: 3-9.

Modifications

In some cases, a Clostridial toxin (or a domain or a sub-domain thereof) comprises one or more modifications. For example, the Clostridial toxin, or fragments thereof, can be cyclized. As another example, the Clostridial toxin, or fragments thereof, can have one or more amino acid modifications, e.g., inclusion of one or more D-amino acids. Modifications of interest that do not alter primary sequence include chemical derivatization of polypeptides, e.g., acetylation or carboxylation. Also included are modifications of glycosylation, e.g. those made by modifying the glycosylation patterns of a polypeptide during its synthesis and processing or in further processing steps; e.g., by exposing the polypeptide to enzymes which affect glycosylation, such as mammalian glycosylating or deglycosylating enzymes. Also embraced are polypeptides that have phosphorylated amino acid residues, e.g., phosphotyrosine, phosphoserine, or phosphothreonine.

Also provided are Clostridial toxins, or fragments thereof, that have been modified using ordinary molecular biological techniques and/or synthetic chemistry so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids.

A toxin may be joined to a wide variety of other oligopeptides or proteins for a variety of purposes. By providing for expression of the subject polypeptides, various post-translational modifications may be achieved. For example, by employing the appropriate coding sequences, one may provide farnesylation or prenylation. For example, the toxin can be bound to a lipid group at a terminus, so as to be able to be bound to a lipid membrane, such as a liposome.

Other suitable modifications on the Clostridial toxin or fragments thereof include, e.g., (1) end-cappings of the terminal of the polypeptides, such as amidation of the C-terminus and/or acetylation or deamination of the N-terminus; (2) introducing peptidomimetic elements in the structure; and (3) cyclization, in which the cyclization of the polypeptide can occur through natural amino acids or non-naturally-occurring building blocks.

A modified Clostridial toxin or a fragment thereof can be a peptoid (N-substituted oligoglycines), e.g., in which an amino acid side chain is connected to the nitrogen of the polypeptide backbone, instead of the α-carbon. See, e.g., Zuckermann et al., *J. Am. Chem. Soc.* 114, 10646, 1992).

A subject toxin can include naturally-occurring and non-naturally occurring amino acids. A Clostridial toxin or a fragment thereof can comprise D-amino acids, a combination of D- and L-amino acids, and various "designer" amino acids (e.g., β-methyl amino acids, Cα-methyl amino acids, and Nα-methyl amino acids, etc.) to convey special properties to polypeptides.

Fusion Proteins and Linked Proteins

It is understood that a modified Clostridial toxin or a fragment thereof disclosed in the present specification can optionally include one or more additional components. As a non-limiting example of an optional component, a modified Clostridial toxin or a fragment thereof can further comprise a flexible region comprising a flexible spacer. Non-limiting examples of a flexible spacer include, e.g., a G-spacer GGGGS (SEQ ID NO: 22) or an A-spacer EAAAK (SEQ ID NO: 23). A flexible region comprising flexible spacers can be used to adjust the length of a polypeptide region in order to optimize a characteristic, attribute or property of a polypeptide. Such a flexible region is operably-linked in-frame to the modified Clostridial toxin or a fragment thereof as a fusion protein. As a non-limiting example, a polypeptide region comprising one or more flexible spacers in tandem can be used to better expose a protease cleavage site thereby facilitating cleavage of that site by a protease. As another non-limiting example, a polypeptide region comprising one or more flexible spacers in tandem can be used to better present a ligand domain, thereby facilitating the binding of that ligand domain to its binding domain on a receptor.

Thus, in an embodiment, a modified Clostridial toxin or a fragment thereof disclosed in the present specification can further comprise a flexible region comprising a flexible spacer. In another embodiment, a modified Clostridial toxin or a fragment thereof disclosed in the present specification can further comprise flexible region comprising a plurality of flexible spacers in tandem. In aspects of this embodiment, a flexible region can comprise in tandem, e.g., at least 1 G-spacer, at least 2 G-spacers, at least 3 G-spacers, at least 4 G-spacers or at least 5 G-spacers. In other aspects of this embodiment, a flexible region can comprise in tandem, e.g., at most 1 G-spacer, at most 2 G-spacers, at most 3 G-spacers, at most 4 G-spacers or at most 5 G-spacers. In still other aspects of this embodiment, a flexible region can comprise in tandem, e.g., at least 1 A-spacer, at least 2 A-spacers, at least 3 A-spacers, at least 4 A-spacers or at least 5 A-spacers. In still other aspects of this embodiment, a flexible region can comprise in tandem, e.g., at most 1 A-spacer, at most 2 A-spacers, at most 3 A-spacers, at most 4 A-spacers or at most 5 A-spacers. In another aspect of this embodiment, a modified Clostridial toxin or a fragment thereof can comprise a flexible region comprising one or more copies of the same flexible spacers, one or more copies of different flexible-spacer regions, or any combination thereof.

Properties of the Clostridial Toxins

Lack of Toxicity Profile

In one embodiment, the present disclosure contemplates compositions and methods directed to Clostridial toxins (e.g., BoNT/A) or fragments thereof of modified toxicity, including reduced toxicity or devoid of toxicity. As is known in the art, toxic activity of Clostridial toxins is particularly contained in the light chain, which is a zinc ($Zn^{2+}$) endopeptidase that selectively cleaves soluble NSF attachment protein receptor ("SNARE") proteins. SNARE proteins are important for recognition and docking of neurotransmitter-containing vesicles with the cytoplasmic surface of the plasma membrane, and fusion of the vesicles with the plasma membrane. TeNT, BoNT/B BoNT/D, BoNT/F, and BoNT/G cause degradation of synaptobrevin (also called vesicle-associated membrane protein (VAMP)), a synaptosomal membrane protein. Most of the cytosolic domain of VAMP extending from the surface of the synaptic vesicle is removed as a result of any one of these cleavage events. BoNT/A and BoNT/E selectively cleave the plasma membrane-associated protein SNAP-25, which is predominantly bound to and present on the cytosolic surface of the plasma membrane. BoNT/C cleaves syntaxin, an integral protein having most of its mass exposed to the cytosol. Syntaxin interacts with the calcium channels at presynaptic terminal active zones. In some embodiments, the toxicity of the Clostridial toxin or a fragment thereof is assayed in terms of induction of neuromuscular paralysis (which is an indication of the toxin molecules' ability to enter the cell and thence to inhibit neurotransmitter release. In some embodiments, the toxicity of Clostridial toxin or a fragment thereof is assayed in terms of $LD_{50}$ values, which is the amount of toxin that induces death in 50% (one half) of a group of test animals, e.g., mice, upon intraperitoneal injection of the toxin construct. See, U.S. Pat. Nos. 7,749,514 and 9,284,545.

In aspects of this embodiment, the Clostridial toxin or a fragment thereof is, e.g., about 0%, 10%, 20%, 30%, 40%, 50%, 60%, 70%, 80%, 90%, 95%, or >99% as toxic as a naturally-occurring Clostridial toxin. In aspects of this embodiment, the modified Clostridial toxin or a fragment thereof is, e.g., at most 10% as toxic as a naturally-occurring Clostridial toxin, at most 1%, 10%, 20%, 30%, 40%, 50%, 60%, 70%, 80%, 90%, 95%, or <95% as toxic as a naturally-occurring Clostridial toxin. Preferably, the Clostridial toxin fragments or variants of the disclosure are devoid of toxicity, e.g., when applied in a conventional manner to a subject.

In one embodiment, the Clostridial toxins of modified toxicity or fragments thereof disclosed herein finds applications including, but not limited to: (a) research (i.e., for example, into the mechanism of action of BoNT/A, including its binding, translocation, and pharmacokinetics, and for its use to develop and test an antidote); (c) assessing risks and diagnostics for indoor release; (d) for examining pharmacokinetics in mammals, including primates; (d) vaccine development; (e) antibody development (for therapy and diagnostics); and (f) clinical therapeutic applications.

Toxicities of Clostridial toxins can be assessed using routine methods. As is known in the art, a multi-step mechanism is involved in the cell intoxication by BoNTs (Chaddock et al., Trends Biochem. Sci. 27, 552-558, 2002). The neurotoxin binds to the pre-synaptic nerve endings of neurons through a heavy chain (H) and enters by receptor-mediated endocytosis (Schiand et al., Physio. Rev. 80, 717-755, 2000). The low pH of endosome is believed to induce channel formation by the $H_{CN}$, which allows translocation of the LC into the cytosol (Li et al., Biochemistry 39, 6466-6474, 2000). It is believed that LC works as a zinc endopeptidase to cleave specifically one of the three different SNARE proteins essential for synaptic vesicle fusion (Montecucco et al., Trends Biochem. Sci. 18, 324-327, 1993; Li et al., Toxin Rev. 18, 95-112, 1999). In one embodiment, BoNT/A and BoNT/E, independently, cleave synaptosomal-associated protein 25 (SNAP-25), a component of the trans-SNARE complex, which is proposed to account for the specificity of membrane fusion and to directly execute fusion by forming a tight complex that brings the synaptic vesicle and plasma membranes together. In another embodiment, TeNT and/or BoNT/B, /D, /F and/G cleave cellubrevin, a protein involved in the docking and/or fusion of synaptic vesicles with the presynaptic membrane. In one embodiment, BoNT/$C_1$ cleaves syntaxin and SNAP-25. Once a SNARE protein is cleaved, the release of a neurotransmitter (i.e., for example, acetylcholine) is prevented, ultimately leading to the flaccid muscle paralysis (Montecucco et al., *Q. Rev. Biophys,* 28:423-472 (1995). The botulinum neurotoxin active site is believed to comprise of a HEXXH+E zinc-binding motif (Li et al., *Biochemistry* 39, 2399-2405, 2000). The general conformation and active site residues appear conserved in all of the Clostridial neurotoxins (Agarwal et al., *Biochemistry* 44, 8291-8302, 2005). For example, the amino acid residues in BoNT/A active site comprise H223-E224-L225-I226-H227+E262 ("H223-E224-L225-I226-H227" disclosed as SEQ ID NO: 24), which are conserved in most, if not all, BoNT subtypes.

Accordingly, the present disclosure relates to a non-toxic form of Clostridial toxin that is devoid of endopeptidase activity or translocation activity or both endopeptidase activity and translocation activity. In one embodiment, provided herein are Clostridial toxin variants lacking endopeptidase activity. Such variants may comprise, for example, mutations or deletions of one or more amino acid residues making up the active site, which confers endopeptidase activity. In another embodiment, the Clostridial toxin variants lacking endopeptidase activity may comprise deletion of a substantial portion, e.g., deletion of about 40%, about 50%, about 60%, about 70%, about 80%, about 90%, about 95%, or >99%, of the amino acids making up the light chain (LC) domain. In another embodiment, the Clostridial toxin variant is devoid of both endopeptidase activity and translocation activity. In this embodiment, the Clostridial toxin variant may comprises deletion of a substantial portion of (a) the amino acids making up the light chain (LC) domain and (b) the amino acids making up the translocation domain.

In the context of BoNT/A, the disclosure contemplates fragments that do not cleave SNAP-25. Reagents and assays for measuring SNAP-25 cleavage activity are known in the art. See, e.g., Mizanur et al., *PLoS One,* 9(4), e95188, 2014.

The disclosure further relates to inactive Clostridial toxins, including fragments thereof. The term "inactive Clostridial toxin" means a Clostridial toxin that is not toxic to a cell. For example, an inactive Clostridial toxin has minimal or no ability to interfere with the release of neurotransmitters from a cell or nerve endings. In some embodiments, the inactive Clostridial toxin has less than about 50%, e.g., about 40%, about 25%, about 10%, about 5%, or a lesser %, e.g., about 2%, of the neurotoxic effect (e.g., ability to inhibit release of neurotransmitter) of an identical Clostridial toxin that is active. For example, an inactive botulinum toxin (iBoNT) has less than about 50%, e.g., about 40%, about 25%, about 10%, about 5%, or a lesser %, e.g., about 2%, of the neurotoxic effect of an identical BoNT that is active (e.g., full-length BoNT). Full-length inactive botulinum toxins are disclosed in, e.g., U.S. Pat. Nos. 6,051,239 and 7,172,764. In some embodiments, the inactive Clostridial toxin comprises a heavy chain that is modified (e.g., glycosylated) as to reduce antigenicity. In some embodiments, inactive Clostridial toxin is a single chain polypeptide. Preferably, the inactive Clostridial toxin of the disclosure comprises a fragment of full length Clostridial toxin that is devoid of the light chain (LC) domain and/or the translocation domain, wherein the fragment Clostridial toxin is further optionally glycosylated so as to reduce antigenicity.

The term "reduced antigenicity," as used herein, means the ability of the inactive Clostridial toxin to induce the production of antibody in a mammal is less than the antigenic effect of a full-length Clostridial toxin, e.g., less than about 100%, less than about 90%, less than about 80%, less than about 70%, less than about 60%, less than about 50%, e.g., about 40%, about 25%, about 10%, about 5%, or a lesser %, e.g., about 2%, of the antigenic effect of a full-length Clostridial toxin. For example, molecules which are glycosylated may have reduced antigenicity because they have minimal or no ability to induce an immune response for the production of antibody in a mammal. Also, epitope regions on a molecule are responsible for the induction of antibodies in a mammal. Thus, molecules with epitope regions mutated or deleted may have reduced antigenicity because these regions are no longer present on the molecule to stimulate antibody production. See, U.S. Pat. No. 7,172,764. For example, an iBoNT comprising a mutated or deleted epitope region within its heavy chain at the carboxy terminal (Hc) can have a reduced antigenicity compared to full-length Clostridial toxin. In some embodiments, the administration of a glycosylated BoNT into a mammal induces less production of antibody as compared to an administration of an identical BoNT which is not glycosylated, by about 2-fold, preferably 4-fold, more preferably 8-fold, or more. The antigenicity of the Clostridial toxins of the instant disclosure can be determined using methods and tools known in the art, e.g., Atassi et al., *Protein J.,* 23(1): 39-52, 2004.

Embodiments disclosed herein further relate to methods for assaying for the toxicity of Clostridial toxins, including fragments and variants thereof, comprising, e.g., biochemical assays, in vitro cell-based assays, in vivo pharmacological assays, and the like. In one embodiment, the Clostridial toxin fragment or variant lacks endopeptidase activity in a standard endopeptidase assay (see, U.S. Pat. Nos. 8,618,261; 8,067,231; 8,124,357; 7,645,570 for variations in the in vitro assay). In another embodiment, the Clostridial toxin fragment or variant is non-lethal.

Modulation of Cell Signaling

In a related embodiment, provided herein are Clostridial toxins, sub-domains or fragments thereof or variants thereof, which modulate the expression of one or more skin quality associated genes, including but not limited to for example FGFR1, MMP1, MMP3, TIMP1, FGF7, TP63, SOD2, UBD, HAS2, HAS3, ADAMTS1, IGF-1, IL-6, IL-32, CCL2, BDKRB1, MC5R, AR, HSD3B1, HSD17B1 and PPARδ.

Changes in expression of these skin quality associated genes affect structural and functional characteristics of skin quality associated cells, tissues and/or organs, including the extracellular matrix structure, resulting in changes in biomechanical properties of the skin, such as for example elasticity and pliability. By "modulate," it is meant that the Clostridial toxin or a fragment or variant thereof, when contacted with a target cell, e.g., fibroblast, keratinocyte, melanocyte, sebocyte, immune cells or neuron, effectuates a change of at least 5%, at least 10%, at least 15%, at least 20%, at least 25%, at least 30%, at least 40%, at least 50%, at least 60%, at least 70%, at least 80%, at least 90%, at least 1-fold, at least 1.5-fold, at least 2-fold, at least 2.5-fold, at least 3-fold, at least 3.5-fold, at least 4-fold, at least 5-fold, at least 6-fold, at least 7-fold, at least 8-fold, at least 10-fold, at least 15-fold, at least 20-fold, at least 30-fold, at least 50-fold, or more, in the expression of one or more of the aforementioned genes compared to a control (e.g., BSA treatment). Methods of measuring gene expression are known in the art, e.g., microarray analysis or quantitative PCR assay. Representative methods are illustrated in the Examples section.

Particularly, provided herein are Clostridial toxins, sub-domains or fragments or variants thereof, which, when contacted with a target cell, e.g., fibroblast or keratinocyte, modulate the expression of one or more genes selected from FGFR1, MMP1, MMP3, TIMP1, FGF7, and TP63. Especially, the Clostridial toxins or fragments or variants thereof increase the expression of each gene in the aforementioned six-gene signature by at least 25%, at least 30%, at least 40%, at least 50%, at least 60%, at least 70%, at least 80%, at least 90%, at least 1-fold, at least 1.5-fold, at least 2-fold, at least 2.5-fold, or more. Changes in expression of these skin quality associated genes affect structural and functional characteristics of skin quality associated cells, tissues and/or organs, including the extracellular matrix structure, resulting in changes in biomechanical properties of the skin, such as for example elasticity and pliability.

Additionally, the disclosure relates to Clostridial toxins or fragments or variants thereof which increase the expression of fibronectin. "Fibronectin," as used herein, refers to a high-molecular weight (~440 kDa) glycoprotein of the extracellular matrix that binds to component proteins in the ECM, e.g., collagen, fibrin, and heparan sulfate proteoglycans. In one embodiment, the Clostridial toxins or fragments or variants thereof, when contacted with a cell, e.g., fibroblast or keratinocyte, increase the expression of fibronectin by at least 25%, at least 30%, at least 40%, at least 50%, at least 60%, at least 70%, at least 80%, at least 90%, at least 1-fold, at least 1.5-fold, at least 2-fold, at least 2.5-fold, at least 3-fold, at least 5-fold, or more. Increase in fibronectin expression affects the structure and function of the dermis, including the extracellular matrix structure, resulting in changes in biomechanical properties of the skin, including elasticity and pliability.

Effect on Target Cells

The disclosure further relates to Clostridial toxins or fragments or variants thereof which change one or more features of the target cells, e.g., cells to which they bind. In one embodiment, the feature is a physical attribute such as size, shape, density, and the number/size of microvilli. In another embodiment, the feature is a functional attribute such as growth, migration, differentiation, secretion (e.g., ECM components) and adhesion (to each other and to the matrix). In yet another embodiment, the feature is differential production of a metabolite such as a lipid, a sugar, a peptide, or a hormone. In a particular embodiment, the feature is attenuated production of a metabolite in the presence of a mediator, e.g., attenuation of oleic acid-induced production of sebum in sebocytes. As shown in the Examples, when contacted with the target cells, e.g., fibroblast cells, the Clostridial toxin fragments effectuate an appreciable change in cellular morphology and/or function. Additionally, when sebum-producing cells, e.g., sebocytes, were treated with the Clostridial toxin fragments, the effect of oleic acid in the overproduction of sebum was significantly attenuated.

The cellular effects of the Clostridial toxins or fragments or variants thereof can be assayed using techniques that are described in detail in the Examples. A variety of target cells, e.g., fibroblasts, keratinocytes, adipocytes, melanocytes, sebocytes; neurons; cell-lines; and tissues may be used to assay for the effect of the Clostridial toxins or fragments or variants thereof at the cellular level.

Polynucleotides

Aspects of the present disclosure provide, in part, polynucleotide molecules. As used herein, the term "polynucleotide molecule" is synonymous with "nucleic acid molecule" and means a polymeric form of nucleotides, such as, e.g., ribonucleotides and deoxyribonucleotides, of any length. It is envisioned that any and all polynucleotide molecules that can encode a modified Clostridial toxin disclosed in the present specification can be useful, including, without limitation naturally-occurring and non-naturally-occurring DNA molecules and naturally-occurring and non-naturally-occurring RNA molecules. Non-limiting examples of naturally-occurring and non-naturally-occurring DNA molecules include single-stranded DNA molecules, double-stranded DNA molecules, genomic DNA molecules, cDNA molecules, vector constructs, such as, e.g., plasmid constructs, phagemid constructs, bacteriophage constructs, retroviral constructs and artificial chromosome constructs. Non-limiting examples of naturally-occurring and non-naturally-occurring RNA molecules include single-stranded RNA, double stranded RNA and mRNA.

In one embodiment, the polynucleotide molecules encode one or more of the aforementioned Clostridial toxins, mutants or variants thereof, domains and/or sub-domains thereof, biologically-active or immunogenic fragments thereof, multimers thereof, chimeras and fusion constructs thereof, tagged constructs thereof, mimetics thereof, or other forms of engineered or synthetic derivatives thereof. Particularly, the polynucleotide molecule is a DNA molecule and especially, the polynucleotide is a cDNA molecule. Also included are polynucleotides which are complementary to the polynucleotides encoding one or more of the aforementioned Clostridial toxins, including, mutants, variants, or fragments thereof. Especially, the polynucleotide is a cDNA molecule encoding the cell-binding domain of BoNT/A or mutants thereof, including, homologs thereof, e.g., cell-binding domains of BoNT/B, BoNT/$C_1$, BoNT/D, BoNT/E, BoNT/F, BoNT/G, BoNT/H, TeNT, BaNT or BuNT. Particularly preferably, the polynucleotide is a cDNA molecule encoding the heavy chain N-terminal sub-domain ($H_{CN}$) of cell-binding domain of BoNT/A or a mutant thereof, including, homologs thereof, e.g., $H_{CN}$ sub-domains of BoNT/B, BoNT/$C_1$, BoNT/D, BoNT/E, BoNT/F, BoNT/G, BoNT/H, BoNT/X, eBoNT/J, TeNT, BaNT or BuNT.

The present disclosure also provides synthetic nucleic acids, e.g., non-natural nucleic acids, comprising nucleotide sequence encoding one or more of the aforementioned Clostridial toxins, including fragments thereof.

Included herein are nucleic acids encoding Clostridial toxin fragment sequences set forth in SEQ ID NO: 1, SEQ ID NO: 19, SEQ ID NOs: 3-5, SEQ ID NO: 6, SEQ ID NO: 20, SEQ ID Nos: 7-10, SEQ ID NO: 11, SEQ ID NO: 21, and SEQ ID NOs: 12-18, or a variant thereof having 1, 2, 3, 4, 5, 7, 10, 15, 20, 25, 30 or more amino substitutions (preferably conserved or semi-conserved amino acid substitutions), or a homolog thereof, including the complementary strand thereto, or the RNA equivalent thereof, or a complementary RNA equivalent thereof.

Also, included herein are nucleic acids encoding Clostridial toxin fragment sequences of SEQ ID NO: 1, SEQ ID NO: 19, SEQ ID NOs: 3-5, SEQ ID NO: 6, SEQ ID NO: 20, SEQ ID Nos: 7-10, SEQ ID NO: 11, SEQ ID NO: 21, and SEQ ID NOs: 12-18, or a variant thereof having 1, 2, 3, 4, 5, 4-10, 5-10, or 5 to 15 amino acid substitutions (preferably conserved or semi-conserved amino acid substitutions), or a homolog thereof, including the complementary strand thereto, or the RNA equivalent thereof, or a complementary RNA equivalent thereof. In some embodiments, the nucleic acids of the disclosure encode fragments of BoNT/A mutants, comprising, consisting of, or consisting of the sequence set forth in SEQ ID NO: 25, SEQ ID NO: 26, or SEQ ID NO: 27.

The disclosure further relates to nucleic acids homologs of Clostridial toxins fragments, e.g., a fragment which encodes the $H_C$ domain, particularly the $H_{CN}$ domain and especially the N-terminal half of the $H_{CN}$ domain of a Clostridial toxin selected from the group consisting of BoNT/A, BoNT/B, BoNT/C₁, BoNT/D, BoNT/E, BoNT/F, BoNT/G, BoNT/H, BoNT/DC, BoNT/X, eBoNT/J, TeNT, BaNT, BuNT, including the aforementioned subtypes thereof. Sequences having substantial homology include nucleic acid sequences having at least 50%, particularly at least 65%, and especially at least 80% identity or greater % identity with the sequences as shown in SEQ ID NO: 2 or a nucleic acid encoding SEQ ID NO: 1, SEQ ID NO: 19, SEQ ID NOs: 3-5, SEQ ID NO: 6, SEQ ID NO: 20, SEQ ID Nos: 7-10, SEQ ID NO: 11, SEQ ID NO: 21, and SEQ ID NOs: 12-18. Sequence identity can be calculated according to methods known in the art, e.g., using BLAST v2.1. See also, Altschul et al., *J. Mol. Biol.* 215:403-410, 1990; Gish et al., *Nature Genet.* 3:266-272, 1993; Madden et al., *Meth. Enzymol.* 266:131-141, 1996; Altschul et al., *Nucleic Acids Res.* 25:3389-3402, 1997; Zhang et al., *Genome Res.* 7:649-656, 1997.

Embodiments disclosed herein further relate to methods of making the above-disclosed polynucleotides. Well-established molecular biology techniques that may be necessary to make a polynucleotide molecule encoding a modified Clostridial toxin disclosed in the present specification including, but not limited to, procedures involving polymerase chain reaction (PCR) amplification, restriction enzyme reactions, agarose gel electrophoresis, nucleic acid ligation, bacterial transformation, nucleic acid purification, nucleic acid sequencing and recombination-based techniques are routine procedures well within the scope of one skilled in the art and from the teaching herein. Non-limiting examples of specific protocols necessary to make a polynucleotide molecule encoding a modified Clostridial toxin are described in e.g., CURRENT PROTOCOLS IN MOLECULAR BIOLOGY (Frederick M. Ausubel et al., eds. John Wiley & Sons, 2004). Additionally, a variety of commercially available products useful for making a polynucleotide molecule encoding a modified Clostridial toxin are widely available. These protocols are routine procedures well within the scope of one skilled in the art and from the teaching herein.

Another aspect of the present disclosure provides a method of producing a Clostridial toxin or fragments or variants thereof comprising, e.g., the steps of introducing an expression construct comprising a polynucleotide molecule encoding the Clostridial toxin or a fragment or variant thereof into a cell and expressing the expression construct in the cell.

The methods disclosed in the present specification include, in part, all Clostridial toxins or fragments or variants thereof disclosed in the present specification. Thus, aspects of this embodiment include producing, without limitation, naturally occurring Clostridial toxins, naturally occurring Clostridial toxins variants, such as, e.g., Clostridial toxins isoforms and Clostridial toxins subtypes, non-naturally occurring Clostridial toxins variants, such as, e.g., conservative or semi-conservative Clostridial toxins variants, non-conservative Clostridial toxins variants, chimeric or fusion constructs comprising one or more of the aforementioned toxins, Clostridial toxins fragments, e.g., biologically active fragments or immunogenic fragments, comprising at least one domain (for example the binding domain of the heavy chain) or a sub-domain of Clostridial toxin (for example the N-terminal half of the binding domain), chimeric or fusion constructs comprising such Clostridial toxins or fragments or variants thereof, tagged constructs, engineered constructs, synthetic constructs, or any combination thereof.

The methods disclosed in the present specification include, in part, a polynucleotide molecule. Particularly, the polynucleotide molecule encodes any Clostridial toxin or a fragment or variant thereof disclosed herein, including, a fusion protein comprising the Clostridial toxin or a fragment or variant thereof. It is envisioned that any and all polynucleotide molecules disclosed in the present specification can be used. Thus, aspects of this embodiment include, without limitation, naturally-occurring and non-naturally-occurring DNA molecules include single-stranded DNA molecules, double-stranded DNA molecules, genomic DNA molecules, cDNA molecules, vector constructs, such as, e.g., plasmid constructs, phagemid constructs, bacteriophage constructs, retroviral constructs and artificial chromosome constructs. Non-limiting examples of naturally-occurring and non-naturally-occurring RNA molecules include single-stranded RNA, double stranded RNA and mRNA.

The methods disclosed in the present specification include, in part, an expression construct. An expression construct comprises a polynucleotide molecule disclosed in the present specification operably-linked to an expression vector useful for expressing the polynucleotide molecule in a cell or cell-free extract. A wide variety of expression vectors can be employed for expressing a polynucleotide molecule encoding a modified Clostridial toxin or a fragment or variant thereof, including, without limitation, a viral expression vector; a prokaryotic expression vector; eukaryotic expression vectors, such as, e.g., a yeast expression vector, an insect expression vector and a mammalian expression vector; and a cell-free extract expression vector. It is further understood that expression vectors useful to practice aspects of these methods may include those which express a modified Clostridial toxin or a fragment or variant thereof under control of a constitutive, tissue-specific, cell-specific or inducible promoter element, enhancer element or both. Non-limiting examples of expression vectors, along with well-established reagents and conditions for making and using an expression construct from such expression vectors are readily available from commercial vendors. The selection, making and use of an appropriate expression vector are routine procedures well within the scope of one skilled in the art and from the teachings herein.

Thus, aspects of this embodiment include, without limitation, a viral expression vector operably-linked to a polynucleotide molecule encoding a modified Clostridial toxin or a fragment or variant thereof; a prokaryotic expression vector operably-linked to a polynucleotide molecule encoding a modified Clostridial toxin or a fragment or variant thereof; a yeast expression vector operably-linked to a polynucleotide molecule encoding a modified Clostridial toxin or a fragment or variant thereof; an insect expression vector operably-linked to a polynucleotide molecule encoding a modified Clostridial toxin or a fragment or variant thereof; and a mammalian expression vector operably-linked to a polynucleotide molecule encoding a modified Clostridial toxin or a fragment or variant thereof. Other aspects of this embodiment include, without limitation, expression constructs suitable for expressing a modified Clostridial toxin or a fragment or variant thereof disclosed in the present specification using a cell-free extract comprising a cell-free extract expression vector operably linked to a polynucleotide molecule encoding a modified Clostridial toxin or a fragment or variant thereof.

The methods disclosed in the present specification include, in part, a cell. It is envisioned that any and all cells can be used. Thus, aspects of this embodiment include, without limitation, prokaryotic cells including, without limitation, strains of aerobic, microaerophilic, capnophilic, facultative, anaerobic, gram-negative and gram-positive bacterial cells such as those derived from, e.g., *Escherichia coli, Bacillus subtilis, Bacillus licheniformis, Bacteroides fragilis, Clostridia perfringens, Clostridia difficile, Caulobacter crescentus, Lactococcus lactis, Methylobacterium extorquens, Neisseria meningitis, Neisseria meningitidis, Pseudomonas fluorescens* and *Salmonella typhimurium*; and eukaryotic cells including, without limitation, yeast strains, such as, e.g., those derived from *Pichia pastoris, Pichia methanolica, Pichia angusta, Schizosaccharomyces pombe, Saccharomyces cerevisiae* and *Yarrowia lipolytica*; insect cells and cell lines derived from insects, such as, e.g., those derived from *Spodoptera frugiperda, Trichoplusia ni, Drosophila melanogaster* and *Manduca Sexta*; stinging cells (specifically, cnidocytes, nematocytes, or ptychocytes) of an organism belonging to the phylum Cnidaria (for example, hydras, sea anemones, jellyfish or corals, e.g., *Aiptasia* sp.) and/or a genetically transformed organism from the phylum Cnidaria; see, U.S. Pat. No. 6,923,976) and mammalian cells and cell-lines derived from mammalian cells, such as, e.g., those derived from mouse, rat, hamster, porcine, bovine, equine, primate and human. Cell lines may be obtained from the American Type Culture Collection (2004); European Collection of Cell Cultures (2204); and the German Collection of Microorganisms and Cell Cultures (2004). Non-limiting examples of specific protocols for selecting, making and using an appropriate cell line are described in e.g., INSECT CELL CULTURE ENGINEERING (Mattheus F. A. Goosen et al. eds., Marcel Dekker, 1993); INSECT CELL CULTURES: FUNDAMENTAL AND APPLIED ASPECTS (J. M. Vlak et al. eds., Kluwer Academic Publishers, 1996); Maureen A. Harrison & Ian F. Rae, GENERAL TECHNIQUES OF CELL CULTURE (Cambridge University Press, 1997); CELL AND TISSUE CULTURE: LABORATORY PROCEDURES (Alan Doyle et al., eds., John Wiley and Sons, 1998); R. Ian Freshney, CULTURE OF ANIMAL CELLS: A MANUAL OF BASIC TECHNIQUE (Wiley-Liss, $4^{th}$ ed. 2000); ANIMAL CELL CULTURE: A PRACTICAL APPROACH (John R. W. Masters ed., Oxford University Press, $3^{rd}$ ed. 2000); MOLECULAR CLONING A LABORATORY MANUAL, supra, (2001); BASIC CELL CULTURE: A PRACTICAL APPROACH (John M. Davis, Oxford Press, $2^{nd}$ ed. 2002); and CURRENT PROTOCOLS IN MOLECULAR BIOLOGY, supra, (2004). Wherein the cell is a Cnidarian cell, it can be transformed using routine techniques of electroporation or using double-stranded RNA. See, Wittlieb et al., *PNAS USA*, 103(16):6208-11, 2006; Pankow et al., *PLoS One*, 2(9): e782, 2007; Khalturin et al., *PLoS Biol.*, 6(11):e278, 2008. These protocols are routine procedures within the scope of one skilled in the art and from the teaching herein.

The methods disclosed in the present specification include, in part, introducing a polynucleotide molecule into a cell. A polynucleotide molecule introduced into a cell can be transiently or stably maintained by that cell. Stably-maintained polynucleotide molecules may be extra-chromosomal and replicate autonomously, or they may be integrated into the chromosomal material of the cell and replicate non-autonomously. It is envisioned that any and all methods for introducing a polynucleotide molecule disclosed in the present specification into a cell can be used. Methods useful for introducing a nucleic acid molecule into a cell include, without limitation, chemical-mediated transfection such as, e.g., calcium phosphate-mediated, diethyl-aminoethyl (DEAE) dextran-mediated, lipid-mediated, polyethyleneimine (PEI)-mediated, polylysine-mediated and polybrene-mediated; physical-mediated transfection, such as, e.g., biolistic particle delivery, microinjection, protoplast fusion and electroporation; and viral-mediated transfection, such as, e.g., retroviral-mediated transfection, see, e.g., Introducing Cloned Genes into Cultured Mammalian Cells, pp. 16.1-16.62 (Sambrook & Russell, eds., Molecular Cloning A Laboratory Manual, Vol. 3, $3^{rd}$ ed. 2001). One skilled in the art understands that selection of a specific method to introduce an expression construct into a cell will depend, in part, on whether the cell will transiently contain an expression construct or whether the cell will stably contain an expression construct. These protocols are routine procedures within the scope of one skilled in the art and from the teaching herein.

In an aspect of this embodiment, a chemical-mediated method, termed transfection, is used to introduce a polynucleotide molecule encoding a modified Clostridial toxin or a fragment or variant thereof into a cell. In chemical-mediated methods of transfection the chemical reagent forms a complex with the nucleic acid that facilitates its uptake into the cells. Such chemical reagents include, without limitation, calcium phosphate-mediated, see, e.g., Martin Jordan & Florian Worm, *Transfection of Adherent and Suspended Cells by Calcium Phosphate,* 33(2) Methods 136-143 (2004); diethyl-aminoethyl (DEAE) dextran-mediated, lipid-mediated, cationic polymer-mediated like polyethyleneimine (PEI)-mediated and polylysine-mediated and polybrene-mediated, see, e.g., Chun Zhang et al., *Polyethylenimine Strategies for Plasmid Delivery to Brain-Derived Cells,* 33(2) *Methods* 144-150 (2004). Such chemical-mediated delivery systems can be prepared by standard methods and are commercially available, see, e.g., CELLPHECT Transfection Kit (Amersham Biosciences, Piscataway, N.J., USA); Mammalian Transfection Kit, Calcium phosphate and DEAE Dextran, (Stratagene, Inc.); LIPOFECTAMINE™ Transfection Reagent (Invitrogen, Inc., Carlsbad, Calif.); EXGEN 500 Transfection kit (Fermentas, Inc., Hanover, Md., USA), and SUPERFECT and EFFECTINE Transfection Kits (Qiagen, Inc., Valencia, Calif., USA).

In another aspect of this embodiment, a physical-mediated method is used to introduce a polynucleotide molecule encoding a modified Clostridial toxin or a fragment or variant thereof into a cell. Physical techniques include, without limitation, electroporation, biolistic and microinjection. Biolistics and microinjection techniques perforate the cell wall in order to introduce the nucleic acid molecule into the cell, see, e.g., Biewenga et al., *J. Neurosci. Methods,* 71(1), 67-75 (1997); and O'Brien et al., *Methods* 33(2), 121-125 (2004). Electroporation, also termed electro permeabilization, uses brief, high-voltage, electrical pulses to create transient pores in the membrane through which the nucleic acid molecules enter and can be used effectively for stable and transient transfections of all cell types, see, e.g., M. Golzio et al., 33(2) *Methods* 126-135 (2004); and Gresch et al., 33(2) *Methods* 151-163 (2004).

In another aspect of this embodiment, a viral-mediated method, termed transduction, is used to introduce a polynucleotide molecule encoding a modified Clostridial toxin or a fragment or variant thereof into a cell. In viral-mediated methods of transient transduction, the process by which viral particles infect and replicate in a host cell has been manipulated in order to use this mechanism to introduce a nucleic acid molecule into the cell. Viral-mediated methods have been developed from a wide variety of viruses including, without limitation, retroviruses, adenoviruses, adeno-associated viruses, herpes simplex viruses, picornaviruses, alphaviruses and baculoviruses, see, e.g., Blesch et al., 33(2) *Methods* 164-172 (2004); and Federico et al., 229 *Methods Mol. Biol.* 3-15 (2003); Poeschla et al., 5(5) *Curr. Opin. Mol. Ther.* 529-540 (2003); Benihoud et al., 10(5) *Curr. Opin. Biotechnol.* 440-447 (1999); Bueler et al., 380(6) *Biol. Chem.* 613-622 (1999); Lai et al., 21(12) *DNA Cell Biol.* 895-913 (2002); Burton et al., 21(12) *DNA Cell Biol.* 915-936 (2002); Grandi et al., 33(2) *Methods* 179-186 (2004); Frolov et al., 93(21) *PNAS* USA 11371-11377 (1996); Ehrengruber et al., 59(1) *Brain Res. Bull.* 13-22 (2002); Kost et al., 20(4) *Trends Biotechnol.* 173-180 (2002); and Huser et al., 3(1) *Am. J Pharmacogenomics* 53-63 (2003).

Adenoviruses, which are non-enveloped, double-stranded DNA viruses, are often selected for mammalian cell transduction because adenoviruses handle relatively large polynucleotide molecules of about 36 kb, are produced at high titer, and can efficiently infect a wide variety of both dividing and non-dividing cells, see, e.g., Hermens et al., 71(1) *J. Neurosci. Methods* 85-98 (1997); and Mizuguchi et al., 52(3) *Adv. Drug Deliv. Rev.* 165-176 (2001). Transduction using adenoviral-based system do not support prolonged protein expression because the nucleic acid molecule is carried from an episome in the cell nucleus, rather than being integrated into the host cell chromosome. Adenoviral vector systems and specific protocols for how to use such vectors are disclosed in, e.g., VIRAPOWER™ Adenoviral Expression System (Invitrogen, Inc., Carlsbad, Calif., USA) and VIRAPOWER™ Adenoviral Expression System Instruction Manual 25-0543 version A, Invitrogen, Inc.; and ADEASY™ Adenoviral Vector System (Stratagene, Inc., La Jolla, Calif., USA) and ADEASY™ Adenoviral Vector System Instruction Manual, Stratagene, Inc.

Polynucleotide molecule delivery can also use single-stranded RNA retroviruses, such as, e.g., oncoretroviruses and lentiviruses. Retroviral-mediated transduction often produce transduction efficiencies close to 100%, can easily control the proviral copy number by varying the multiplicity of infection (MOI), and can be used to either transiently or stably transduce cells, see, e.g., Tonini et al., 285 *Methods Mol. Biol.* 141-148 (2004); Blesch et al., 33(2) *Methods* 164-172 (2004); Recillas-Targa et al., 267 *Methods Mol. Biol.* 417-433 (2004); and Wolkowicz et al., 246 *Methods Mol. Biol.* 391-411 (2004). Retroviral particles consist of an RNA genome packaged in a protein capsid, surrounded by a lipid envelope. The retrovirus infects a host cell by injecting its RNA into the cytoplasm along with the reverse transcriptase enzyme. The RNA template is then reverse transcribed into a linear, double stranded cDNA that replicates itself by integrating into the host cell genome. Viral particles are spread both vertically (from parent cell to daughter cells via the provirus) as well as horizontally (from cell to cell via virions). This replication strategy enables long-term persistent expression since the nucleic acid molecules of interest are stably integrated into a chromosome of the host cell, thereby enabling long-term expression of the protein. For instance, animal studies have shown that lentiviral vectors injected into a variety of tissues produced sustained protein expression for more than 1 year, see, e.g., Naldini et al., 272(5259) *Science* 263-267 (1996). The Oncoretroviruses-derived vector systems, such as, e.g., Moloney murine leukemia virus (MMLV), are widely used and infect many different non-dividing cells. Lentiviruses can also infect many different cell types, including dividing and non-dividing cells and possess complex envelope proteins, which allows for highly specific cellular targeting.

Retroviral vectors and specific protocols for how to use such vectors are disclosed in, e.g., U.S. Pat. Nos. 5,464,758; 5,814,618; 5,514,578; 5,364,791; 5,874,534; and 5,935,934. Furthermore, such viral delivery systems can be prepared by standard methods and are commercially available, see, e.g., BD™ TET-OFF and TET-ON Gene Expression Systems (BD Biosciences-Clontech, Palo Alto, Calif., USA) and BD™ TET-OFF and TET-ON Gene Expression Systems User Manual, BD Biosciences, GENESWITCH™ System (Invitrogen, Inc., Carlsbad, Calif., USA) and GENE-SWITCH™ System A Mifepristone-Regulated Expression System for Mammalian Cells version D, 25-0313, Invitrogen, Inc., (Nov. 4, 2002); VIRAPOWER™ Lentiviral Expression System (Invitrogen, Inc., Carlsbad, Calif., USA) and VIRAPOWER™ Lentiviral Expression System Instruction Manual, Invitrogen, Inc.; and COMPLETE CONTROL® Retroviral Inducible Mammalian Expression System (Stratagene, La Jolla, Calif., USA) and COMPLETE CONTROL® Retroviral Inducible Mammalian Expression System Instruction Manual.

The methods disclosed in the present specification include, in part, expressing a modified Clostridial toxin or a fragment or variant thereof from a polynucleotide molecule. It is envisioned that any of a variety of expression systems may be useful for expressing a modified Clostridial toxin or a fragment or variant thereof from a polynucleotide molecule disclosed in the present specification, including, without limitation, cell-based systems and cell-free expression systems. Cell-based systems include, without limitation, viral expression systems, prokaryotic expression systems, yeast expression systems, baculoviral expression systems, insect expression systems and mammalian expression systems. Cell-free systems include, without limitation, wheat germ extracts, rabbit reticulocyte extracts and *E. coli* extracts and generally are equivalent to the method disclosed herein. Expression of a polynucleotide molecule using an expression system can include any of a variety of characteristics including, without limitation, inducible expression, non-inducible expression, constitutive expression, viral-mediated expression, stably-integrated expression, and transient expression. Expression systems that include well-characterized vectors, reagents, conditions and cells are well-established and are readily available from commercial vendors that include, without limitation, Ambion, Inc., Austin, Tex.; BD Biosciences-Clontech, Palo Alto, Calif.; BD Biosciences Pharmingen, San Diego, Calif.; Invitrogen, Inc., Carlsbad, Calif.; QIAGEN, Inc., Valencia, Calif.; Roche Applied Science, Indianapolis, Ind.; and Stratagene, La Jolla, Calif. Non-limiting examples on the selection and use of appropriate heterologous expression systems are described in e.g., PROTEIN EXPRESSION. A PRACTICAL APPROACH (S. J. Higgins and B. David Hames eds., Oxford University Press, 1999); Joseph M. Fernandez & James P. Hoeffler, GENE EXPRESSION SYSTEMS. USING NATURE FOR THE ART OF EXPRESSION (Academic Press, 1999); and Rai et al., 80(9) *Curr. Sci.* 1121-1128, (2001). These protocols are routine procedures well within the scope of one skilled in the art and from the teaching herein.

A variety of cell-based expression procedures are useful for expressing a modified Clostridial toxin or a fragment or variant thereof encoded by polynucleotide molecule disclosed in the present specification. Examples included, without limitation, viral expression systems, prokaryotic expression systems, yeast expression systems, baculoviral expression systems, insect expression systems and mammalian expression systems. Viral expression systems include, without limitation, the VIRAPOWER™ Lentiviral (Invitrogen, Inc.) the Adenoviral Expression Systems (Invitrogen, Inc.), the ADEASY™ XL Adenoviral Vector System (Stratagene) and the VIRAPORT® Retroviral Gene Expression System (Stratagene). Non-limiting examples of prokaryotic expression systems include the CHAMPION™ pET Expression System (EMD Biosciences-Novagen, Madison, Wis., USA), the TRIEX™ Bacterial Expression Systems (EMD Biosciences-Novagen, Madison, Wis., USA), the QIAEXPRESS® Expression System (QIAGEN, Inc.), and the AFFINITY® Protein Expression and Purification System (Stratagene). Yeast expression systems include, without limitation, the EASYSELECT™ Pichia Expression Kit (Invitrogen, Inc.), the YES-ECHO™ Expression Vector Kits (Invitrogen, Inc.) and the SPECTRA™ S. pombe Expression System (Invitrogen, Inc., Carlsbad, Calif.). Non-limiting examples of baculoviral expression systems include the BACULODIRECT™ (Invitrogen, Inc.), the BAC-TO-BAC® (Invitrogen, Inc.), and the BD BACULOGOLD™ (BD Biosciences-Pharmigen, San Diego, Calif., USA). Insect expression systems include, without limitation, the Drosophila Expression System (DES®) (Invitrogen, Inc., Carlsbad, Calif.), INSECTSELECT™ System (Invitrogen, Inc.) and INSECTDIRECT™ System (EMD Biosciences-Novagen). Non-limiting examples of mammalian expression systems include the T-REX™ (Tetracycline-Regulated Expression) System (Invitrogen, Inc.), the FLP-IN™ T-REx™ System (Invitrogen, Inc.), the PCDNA™ system (Invitrogen, Inc.), the pSecTag2 system (Invitrogen, Inc.), the EXCHANGER® System, INTERPLAY™ Mammalian TAP System (Stratagene), COMPLETE CONTROL® Inducible Mammalian Expression System (Stratagene) and LACSWITCH® II Inducible Mammalian Expression System (Stratagene).

Another procedure of expressing a modified Clostridial toxin or a fragment or variant thereof encoded by polynucleotide molecule disclosed in the present specification employs a cell-free expression system such as, without limitation, prokaryotic extracts and eukaryotic extracts. Non-limiting examples of prokaryotic cell extracts include the RTS 100 E. coli HY Kit (Roche Applied Science, Indianapolis, Ind., USA), the ACTIVEPRO In vitro Translation Kit (Ambion, Inc., Austin, Tex., USA), the ECO-PRO™ System (EMD Biosciences) and the EXPRESSWAY™ Plus Expression System (Invitrogen, Inc.). Eukaryotic cell extract includes, without limitation, the RTS 100 Wheat Germ CECF Kit (Roche Applied Science, Indianapolis, Ind., USA), the TNT® Coupled Wheat Germ Extract Systems (Promega Corp.), the Wheat Germ IVT™ Kit (Ambion, Inc.), the Retic Lysate IVT™ Kit (Ambion, Inc.), the PROTEINSCRIPT® II System (Ambion, Inc.) and the TNT® Coupled Reticulocyte Lysate Systems (Promega Corp.).

Codon Optimized Sequences

Included herein are codon-optimized sequences of the aforementioned nucleic acid sequences and vectors. Codon optimization for expression in a host cell, e.g., bacteria such as E. coli or insect Hi5 cells, may be performed using Codon Optimization Tool (CODONOPT), available freely from Integrated DNA Technologies, Inc., Coralville, Iowa, USA.

Compositions

Embodiments of the disclosure further relate to compositions containing one or more Clostridial toxins, including, fragments or variants thereof and a carrier. Further embodiments relate to compositions comprising nucleic acids, codon-optimized nucleic acids, vectors, and production systems, e.g., host cells, encoding one or more Clostridial toxins, including, fragments or variants thereof. Still further, embodiments of the disclosure relate to compositions comprising antibodies which bind with specificity to one or more Clostridial toxins, including, fragments or variants thereof.

In one aspect, the disclosure relates to a pharmaceutical composition which is pharmaceutically acceptable. As used herein, the term "pharmaceutically acceptable" refers to any molecular entity or composition that does not produce an adverse, allergic, or other untoward or unwanted reaction when administered to an individual. As used herein, the term "pharmaceutically acceptable composition" is synonymous with "pharmaceutical composition" and refers to a therapeutically effective concentration of an active ingredient, such as, e.g., any of the Clostridial toxins, fragments, variants, or chimeras disclosed in the present specification. A pharmaceutical composition comprising a Clostridial toxin or Clostridial toxin fragment or a variant thereof is useful for medical and veterinary applications. A pharmaceutical composition may be administered to a patient alone, or in combination with other supplementary active ingredients, agents, drugs or hormones. The pharmaceutical compositions may be manufactured using any of a variety of processes, including, without limitation, conventional mixing, dissolving, granulating, levigating, emulsifying, encapsulating, entrapping, and lyophilizing. The pharmaceutical composition can take any of a variety of forms including, without limitation, a sterile solution, suspension, emulsion, lyophilizate, tablet, pill, pellet, capsule, powder, syrup, elixir or any other dosage form suitable for administration.

It is also envisioned that a pharmaceutical composition comprising a Clostridial toxin or Clostridial toxin fragment or variant disclosed in the present specification can optionally include pharmaceutically acceptable carriers that facilitate processing of an active ingredient into pharmaceutically acceptable compositions. As used herein, the term "pharmaceutically acceptable carrier" and refers to any carrier that has substantially no long term or permanent detrimental effect when administered and encompasses terms such as "pharmaceutically acceptable vehicle, stabilizer, diluent, additive, auxiliary, or excipient." Such a carrier generally is mixed with an active compound or is permitted to dilute or enclose the active compound and can be a solid, semi-solid, or liquid agent. It is understood that the active ingredients can be soluble or can be delivered as a suspension in the desired carrier or diluent. Any of a variety of pharmaceutically acceptable carriers can be used including, without limitation, aqueous media such as, e.g., water, saline, glycine, hyaluronic acid and the like; solid carriers such as, e.g., mannitol, lactose, starch, magnesium stearate, sodium saccharin, talcum, cellulose, glucose, sucrose, magnesium carbonate, and the like; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in PHARMACEUTICAL DOSAGE FORMS AND DRUG DELIVERY SYSTEMS (Howard C. Ansel et al., eds., Lippincott Williams & Wilkins Publishers, 7th ed. 1999); REMINGTON: THE SCIENCE AND PRACTICE OF PHARMACY (Alfonso R. Gennaro ed., Lippincott, Williams & Wilkins, 20th ed. 2000); GOODMAN & GILMAN'S THE PHARMACOLOGICAL BASIS OF THERAPEUTICS (Joel G. Hardman et al., eds., McGraw-Hill Professional, 10th ed.

2001); and HANDBOOK OF PHARMACEUTICAL EXCIPIENTS (Raymond C. Rowe et al., APhA Publications, 4th edition 2003). These protocols are routine procedures and any modifications are well within the scope of one skilled in the art and from the teaching herein.

It is further envisioned that a pharmaceutical composition disclosed in the present specification can optionally include, without limitation, other pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, sweetening or flavoring agents, and the like. Various buffers and refers to for adjusting pH can be used to prepare a pharmaceutical composition disclosed in the present specification, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate, a stabilized oxy chloro composition, such as, e.g., PURITE® and chelants, such as, e.g., DTPA or DTPA-bisamide, calcium DTPA, and CaNaDTPA-bisamide. Tonicity adjustors useful in a pharmaceutical composition include, without limitation, salts such as, e.g., sodium chloride, potassium chloride, mannitol or glycerin and other pharmaceutically acceptable tonicity adjustor. The pharmaceutical composition may be provided as a salt and can be formed with many different acids, including, but not limited to, hydrochloric, sulfuric, acetic, lactic, tartaric, malic, and succinic. Salts tend to be more soluble in aqueous or other protonic solvents than are the corresponding free base forms. It is understood that these and other substances known in the art of pharmacology can be included in a pharmaceutical composition useful in the specification.

In an embodiment, a composition comprises a Clostridial toxin or Clostridial toxin fragment or variant and a viscous carrier. "Viscous carrier" means a biocompatible compound which when formulated with a botulinum neurotoxin provides upon in vivo local injection of the formulation a depot from which the Clostridial toxin or a fragment or variant thereof is released in amounts such that the extent of diffusion of the Clostridial toxin or a fragment or variant thereof away from the site of the local injection and/or the amount of the Clostridial toxin or a fragment or variant thereof which diffuses away from the site of local injection is significantly reduced. Any suitable viscous carrier, for example, ophthalmically acceptable viscous carrier, may be employed in accordance with the present disclosure. The viscous carrier is present in an amount effective in providing the desired viscosity to the drug delivery system. Advantageously, the viscous carrier is present in an amount in a range of from about 0.5 wt % to about 95 wt % of the drug delivery system. The specific amount of the viscous carrier used depends upon a number of factors including, for example and without limitation, the specific viscous carrier used, the molecular weight of the viscous carrier used, the viscosity desired for the present drug delivery system being produced and/or used and like factors.

Examples of useful viscous carriers include, but are not limited to, hyaluronic acid, carbomers, polyacrylic acid, cellulosic derivatives, polycarbophil, polyvinylpyrrolidone, gelatin, dextrin, polysaccharides, polyacrylamide, polyvinyl alcohol, polyvinyl acetate, heparin, proteoglycan (HSPG), heparin sulfate (HS), derivatives thereof and mixtures thereof. Representative types of viscous carriers are disclosed in U.S. Pat. Nos. 9,044,477; 9,622,957; 9,050,336.

A dermal filler can also be used as the viscous carrier. Suitable dermal fillers for that purpose include collagen (sterile collagen is sold under the trade names ZYDERM, ZYPLAST, COSMODERM, COSMOPLAST and AUTOLGEN), HYLAFORM® (hyaluronic acid), RESTYLANE® (hyaluronic acid), SCULPTRA™ (polylactic acid), RADIESSE™ (calcium hydroxyl apatite) and JUVEDERM™. JUVEDERM™, available from Allergan, Inc. (Irvine, Calif., USA) comprises a sterile, biodegradable, non-pyrogenic, viscoelastic, clear, colorless, homogenized gel consisting of cross-linked hyaluronic acid formulated at a concentration of 24 mg/ml in a physiologic buffer. Representative types of dermal fillers are disclosed in U.S. Pat. Nos. 9,622,957; 9,161,970; 9,050,336.

The molecular weight of the presently useful viscous carrier can be in a range of about 10,000 Daltons or less to about 2 million Daltons or more. In one particularly useful embodiment, the molecular weight of the viscous carrier is in a range of about 100,000 Daltons or about 200,000 Daltons to about 1 million Daltons or about 1.5 million Daltons. Again, the molecular weight of the viscous carrier useful in accordance with the present disclosure, may vary over a substantial range based on the type of viscous carrier employed, and the desired final viscosity of the present drug delivery system in question, as well as, possibly other factors.

In one very useful embodiment, the carrier is a polymeric hyaluronate component, for example, a metal hyaluronate component, preferably selected from alkali metal hyaluronates, alkaline earth metal hyaluronates and mixtures thereof, and still more preferably selected from sodium hyaluronates, and mixtures thereof. The molecular weight of such hyaluronate component preferably is in a range of about 50,000 Daltons or about 100,000 Daltons to about 1.3 million Daltons or about 2 million Daltons. In one embodiment, the present compositions include a polymeric hyaluronate component in an amount in a range about 0.05% to about 0.5% (w/v). In a further useful embodiment, the hyaluronate component is present in an amount in a range of about 1% to about 4% (w/v) of the composition. In this latter case, the very high polymer viscosity forms a gel that slows particle sedimentation rate to the extent that often no resuspension processing is necessary over the estimated shelf life, for example, at least about 2 years, of the drug delivery system. Such a drug delivery system can be marketed in pre-filled syringes since the gel cannot be easily removed by a needle and syringe from a bulk container.

In another embodiment, the carrier is a thermo-reversible gelling agent, such as, e.g., poloxamer-407, which is described in U.S. Pat. No. 9,107,815. Such compositions comprising thermo-reversible gels can be administered (as by injection) as a low viscosity liquid that rapidly increases in viscosity after injection. The resulting high viscosity matrix is adhesive, biodegradable and biocompatible and upon administration forms a depot from which the botulinum toxin can be released, thereby providing a sustained or extended release drug delivery system. In this manner, a lower dose of the botulinum toxin can be used. Such a pharmaceutical composition can be administered pre-mixed or as a simple reconstitution vehicle or its several compartments combined at the time of administration, as by use of a dual chamber syringe. Representative types of thermoreversible gelling agents are disclosed in, e.g., U.S. Pat. Nos. 8,168,206; 8,642,047; and 9,278,140.

In some embodiments, to increase the resident time of the Clostridial toxin or a fragment or variant thereof in the joint, the Clostridial toxin or a fragment or variant thereof is provided in a controlled release system comprising a polymeric matrix encapsulating the Clostridial toxin or a fragment or variant thereof, wherein fractional amount of the Clostridial toxin or a fragment or variant thereof is released from the polymeric matrix over a prolonged period of time in a controlled manner. Controlled release neurotoxin systems have been disclosed, for example, in U.S. Pat. Nos. 6,585,993; 6,585,993; 6,306,423; and 6,312,708.

In one embodiment, the disclosure relates to topical compositions comprising a Clostridial toxin or a fragment or variant thereof. Representative examples include, e.g., a topical cream comprising BoNT/A fragments, e.g., the full-length heavy chain ($H_C$) or the N-terminal domain thereof ($H_{CN}$) of Clostridial toxins, or variants thereof, which are delivered via commercially viable ionic nanoparticle technology, INPART® (Transdermal Corp., Birmingham, Mich., USA). See U.S. Pat. Nos. 7,838,011; 7,727,537; 8,568,740.

Pharmaceutical compounds and formulations for topical administration may include ointments, lotions (e.g., skin care lotion), creams, gels, drops, suppositories, sprays, liquids and powders. Conventional pharmaceutical carriers, aqueous, powder or oily bases, thickeners and the like may be used. Preferred topical formulations include those in which the compounds of the invention are in admixture with a topical delivery agent such as lipids, liposomes, fatty acids, fatty acid esters, steroids, chelating agents and surfactants. Preferred lipids and liposomes include neutral (e.g., dioleoylphosphatidyl DOPE ethanolamine, dimyristoylphosphatidyl choline DMPC, distearolyphosphatidyl choline) negative (e.g., dimyristoylphosphatidyl glycerol DMPG) and cationic (e.g., dioleoyltetramethylaminopropyl DOTAP and dioleoylphosphatidyl ethanolamine DOTMA). The Clostridial toxins of the disclosure or fragments or variants thereof may be encapsulated within liposomes or may form complexes thereto, in particular to cationic liposomes. Alternatively, compounds may be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acetylcholine, or a $C_{1-10}$ alkyl ester (e.g., isopropylmyristate IPM), monoglyceride, diglyceride or pharmaceutically acceptable salt thereof. Topical formulations are described in detail in U.S. Pat. No. 6,747,014.

In another embodiment, the disclosure relates to relates to transdermal compositions comprising a Clostridial toxin or a fragment or variant thereof, more specifically to such compositions that enable the transport or delivery of a Clostridial toxin or a fragment or variant thereof through the skin or epithelium (also referred to as "transdermal delivery"). Such compositions may be used as topical applications for providing a botulinum toxin to a subject, for various therapeutic, aesthetic and/or cosmetic purposes, as described herein. For instance, the composition for topical delivery may comprise a positively charged carrier molecule having efficiency groups, such that the toxin is administered transdermally to muscles and/or other skin-associated structures. The transport occurs without covalent modification of the botulinum toxin. Exemplary compositions and delivery systems are provided in patches developed by Revance Therapeutics, e.g., U.S. Pat. Nos. 8,568,740; 8,518,414; 9,180,081; 8,404,249; 8,962,548; 9,211,248; 8,398,997; 8,974,774; 8,926,991; and 8,092,788. See also U.S. Pat. Nos. 8,404,249; 9,144,692; and 7,704,524. In one embodiment, the transdermal delivery system is a patch. Transdermal patches are generally characterized as having an adhesive layer, which will be applied to a person's skin, a depot or reservoir for holding a pharmaceutical agent, and an exterior surface that prevents leakage of the pharmaceutical from the depot. The exterior surface of a patch is typically non-adhesive. In accordance with the present disclosure, the Clostridial toxin or a fragment or variant thereof is incorporated into the patch so that the neurotoxin remains stable for extended periods of time. The Clostridial toxin or a fragment or variant thereof may be incorporated into a polymeric matrix that stabilizes the Clostridial toxin or a fragment or variant thereof, and permits the Clostridial toxin or a fragment or variant thereof to diffuse from the matrix and the patch. In one embodiment of the disclosure, the composition containing the toxin and the enhancing agent is provided in an adhesive patch. The Clostridial toxin or a fragment or variant thereof may also be incorporated into the adhesive layer of the patch so that once the patch is applied to the skin, the Clostridial toxin or a fragment or variant thereof may diffuse through the skin. Examples of adhesive patches for the delivery of proteins are well known. For example, see U.S. Pat. Nos. 296,006 (design patent); 6,010,715; 5,591,767; 5,008,110; 5,683,712; 5,948,433; and 5,965,154. In some embodiments, the patches may include lipid vesicles (see, U.S. Pat. No. 6,165,500). In some embodiments, the patches may include stinging cells (specifically, cnidocytes, nematocytes, or ptychocytes) of an organism belonging to the phylum Cnidaria (e.g., *Aiptasia* sp.) which have been transformed with a vector comprising a nucleic acid encoding the Clostridial toxin of the disclosure or a fragment or variant thereof. In some embodiments, the patches may include a transgenic organism of the phylum Cnidaria which expresses the Clostridial toxin of the disclosure or a fragment or variant thereof in specialized cells, e.g., stinging cells.

Kits

Another aspect of the disclosure relates to a kit comprising a Clostridial toxin or a fragment or variant thereof, including nucleic acids encoding the Clostridial toxin or a fragment or variant thereof, or an antibody binding to the Clostridial toxin or a fragment or variant thereof and an instructional material. In one embodiment, the Clostridial toxin or a fragment or variant thereof is part of an immunogenic composition. In another embodiment, the Clostridial toxin or a fragment or variant thereof is part of a conjugate, e.g., a tagged protein. As used herein, an "instructional material" includes a publication, a recording, a diagram, or any other medium of expression which is used to communicate the usefulness of the Clostridial toxin or a fragment or variant thereof for diagnosing, imaging, treating, ameliorating, relieving, inhibiting, preventing, or reducing a disorder in a subject or for administering such a composition via a route described herein. The instructional material may also, for example, describe an appropriate dose of the Clostridial toxin or a fragment or variant thereof. The instructional material of the kit of the disclosure may, for example, be affixed to a container which contains a Clostridial toxin or a fragment or variant thereof or be shipped together with a container which contains the Clostridial toxin or a fragment or variant thereof. Alternatively, the instructional material may be shipped separately from the container with the intention that the instructional material and the modified BoNT/A polypeptide be used cooperatively by the recipient.

The disclosure also includes a kit comprising Clostridial toxin or a fragment or variant thereof and a delivery device for delivering the polypeptide to a subject. By way of example, the delivery device may be a squeezable spray bottle, a metered-dose spray bottle, an aerosol spray device, an atomizer, a dry powder delivery device, a self-propelling solvent/powder dispensing device, a syringe, a needle, a tampon, or a dosage measuring container. The kit may further comprise an instructional material as described herein.

Typically, the container may hold one or more formulations and a label on, or associated with, the container that may indicate directions for reconstitution and/or use. For example, the label may indicate that the formulation is reconstituted to concentrations as described above. The label may further indicate that the formulation is useful or intended for, for example, cutaneous administration. In some embodiments, a container may contain a single dose of a stable formulation containing the Clostridial toxin or a fragment or variant thereof. In various embodiments, a single dose of the stable formulation is present in a volume of less than about 0.5 ml or less. Alternatively, a container holding the formulation may be a multi-use vial, which allows for repeat administrations (e.g., from 2-6 administrations) of the formulation. Kits or other articles of manufacture may further include a second container comprising a suitable diluent (e.g., BWFI, saline, buffered saline). Upon mixing of the diluent and the formulation, the final polypeptide concentration in the reconstituted formulation will generally be at least 1 pg/ml (e.g., at least 5 pg/ml, at least 10 pg/ml, at least 20 pg/ml, at least 50 pg/ml, at least 100 pg/ml, at least 300 pg/ml, at least 500 pg/ml, at least 1 ng/ml, at least 3 ng/ml, at least 10 ng/ml, 0.1 µg/ml, 0.3 µg/ml, 1 g/ml, 3 µg/ml, 10 µg/ml, 30 µg/ml, 100 µg/ml, or more). Kits or other articles of manufacture may further include other materials desirable from a commercial and user standpoint, including other buffers, diluents, filters, needles, syringes, and package inserts with instructions for use. In some embodiments, kits or other articles of manufacture may include an instruction for administration.

Devices and Systems

Embodiments of the present disclosure further relate to devices and/or systems comprising the Clostridial toxins, including, fragments or variants thereof. Representative examples of delivery systems include, e.g., polyether ester copolymer microspheres for encapsulation and controlled delivery of a variety of protein drugs, including tetanus and botulinum antitoxins (see, U.S. Pat. No. 5,980,948); microspherical particles comprising a continuous matrix of biodegradable polymer containing discrete regions containing botulinum toxins (U.S. Pat. No. 5,902,565). In another embodiment, the delivery systems include implants for pulsatile or continuous in vivo release of a neurotoxin over a period ranging from several days to a few years (see, e.g., U.S. Pat. Nos. 6,383,509; 6,506,399; 6,312,708; 6,585,993; and 6,306,423). As used herein, "implant" generally relates to a controlled release (e.g., pulsatile or continuous) composition or drug delivery system. The implant can be, for example, injected, inserted or implanted into a subject's body. The implant may be administered for a few days up to a year or more, e.g., 7 days, 15 days, 30 days, 1 month, 3 months, 6 months, 1 year, or more.

In one specific embodiment, provided herein are delivery systems for delivering the Clostridial toxins into the skin of a subject. Human skin has two distinct layers and varies in thickness from about 1.5 to about 4 mm or more, depending on the regions of the body. The first layer is the superficial layer called the epidermis. It is a relatively thick epithelium. Deep to the epidermis is the second layer called the dermis. The dermis is a fibrous connective tissue and comprises sweat glands and nerves, or nerve terminals, innervating such sweat glands. Just below the skin lies a fatty layer called the hypodermis, which may also be considered a part of a subcutaneous layer. Beneath the hypodermis or subcutaneous layer lies the deep fascial investment of the specialized structures of the body, for example the muscles.

Accordingly, in one embodiment the delivery delivers a Clostridial toxin, or DNA encoding the Clostridial toxin, to a tissue of an animal or a human subject. In one embodiment, the Clostridial toxin is delivered to the layer of the skin in which nerve terminals are found. For example, delivery is to the dermis layer. In another embodiment, delivery is to at least one layer of the skin and substantially to tissues beneath. For example, the Clostridial toxin or a fragment or variant thereof is delivered to the dermis layer of the skin and to the subcutaneous layer. In another embodiment, the Clostridial toxin is delivered to the skin and to muscle tissues beneath. In still another embodiment, Clostridial toxin is delivered substantially to the muscle tissue.

The delivery of a composition comprising a carrier and a Clostridial toxin and/or DNA encoding a Clostridial toxin to a site may be accomplished via any means known in the art, e.g., needle-based delivery methods or needle-less delivery methods.

In one embodiment, the compositions are delivered via needleless delivery. Needleless injectors and their use are well known in the art. See for example, U.S. Pat. Nos. 6,053,889; 6,013,050; 6,010,478; 6,004,286 and 5,899,880, which disclose needleless injectors. In one embodiment, the needleless injector comprises an elongated tubular nozzle and is connected to or capable of connection to a suitable energizing means for producing a supersonic gas flow, for example a burst of helium, which accelerates mediums to high velocity toward a skin surface and into the skin surface. Such a device may be purchased from POWDERJECT Pharmaceuticals, Oxford, UK. In one embodiment, the gas pressure provided must be sufficient to discharge the compositions into a targeted site, for example the dermis, but not so great as to damage the target. In another embodiment, the gas pressure provided is sufficient to deliver the compositions to a target site, for example the dermis, but not so great as to damage the skin surface, for example the epithelium. In another embodiment, the gas pressure is sufficient to deliver the compositions to the dermis layer, but not to the layers below, for example the subcutaneous layer and/or the muscle tissues. In another embodiment, the gas pressure provided must be sufficient to discharge the drug particles into a targeted site, for example the dermis and/or substantially to the muscle tissue below, but not so great as to damage the skin surface.

Advantages for using a needleless injector include, for example, an optimal delivery to a specific tissue layer, for example the dermis layer. Furthermore, in the case where the delivery is to the dermis and not the muscle tissues, the treatment may not cause a loss of motor function in the area being treated. Also, the use of a needleless injector improves clinical safety by eliminating the risk of infection from accidental injury with needles or from potential splash back of bodily fluids from liquid jet injectors, thereby avoiding the possibilities of cross-contamination of blood-borne pathogens such as HIV and hepatitis B. The needleless injector also offers an optimal and specific delivery of drug particles to treat conditions with little pain or skin damage such as bruising or bleeding. Needless systems containing purified Clostridial toxins are disclosed in U.S. Pat. No. 7,255,865.

In another embodiment, the disclosure further relates to needle-based systems comprising Clostridial toxins and a carrier. Representative types of injection systems are known in the art, e.g., U.S. Pat. No. 8,603,028 (relating to injection devices having an angled tip portion); U.S. Pat. No. 8,801,659 (relating to injection devices for delivering viscous agents into soft tissues). In certain embodiments, compositions can be injected into a site via traditional delivery systems, e.g., syringes, catheters, needles and other devices.

Dosages

In one embodiment, the compositions disclosed herein contain an effective amount of Clostridial toxin or a fragment thereof. The term "effective amount," when used with respect to treating a condition, can be a dose sufficient to treat the symptoms, for example, by at least 30%, 40%, 50%, 60%, 70%, 80%, 90% or 100%. In the context of the Clostridial toxins comprising only the binding domains (and/or fragments thereof, the dose generally is in the range of 0.1-1000 mg/day and can be, for example, in the range of 1-500 pg/day, 100-5000 pg/day, 1-500 ng/day, 100-5000 ng/day, 1-500 g/day, 100-5000 g/day, 5-1000 mg/day, 10-500 mg/day, 20-500 mg/day, 50-500 mg/day, 10-200 mg/day, 10-100 mg/day or 100-500 mg/day, with the actual amount to be administered determined by a physician taking into account the relevant circumstances including the age and weight of the patient, the patient's general physical condition, and the route of administration. Where repeated administration is used, the frequency of administration depends, in part, on the half-life of the pharmaceutical composition.

In another embodiment, the concentration of the Clostridial toxin or a fragment or variant thereof in the formulation can be in the range of about 1 pg/ml to 1000 pg/ml toxin, 1 ng/ml to 1000 µg/ml toxin, for example, about 10 ng/ml to 500 µg/ml toxin, 100 ng/ml to 100 µg/ml toxin, 200 ng/ml to 500 µg/ml toxin, 200 ng/ml to 5000 ng/ml toxin, 500 ng/ml to 5000 ng/ml, 10 ng/ml to 5000 ng/ml, 20 ng/ml to 5000 ng/ml, 50 ng/ml to 1000 ng/ml, 100 ng/ml to 10 µg/ml, 100 ng/ml to 5000 ng/ml, 100 ng/ml to 1000 ng/ml, 10 ng/ml to 100 ng/ml, 200 ng/ml to 10 µg/ml, 200 ng/ml to 1000 ng/ml, 500 ng/ml to 50 µg/ml, 500 ng/ml to 10 µg/ml or 1000 ng/ml to 10 µg/ml toxin. In another embodiment, the concentration of the Clostridial toxin or a fragment or variant thereof in the formulation can be in the range of about 1 pM to 500 pM, 0.1 nM to 500 µM, 1.0 nM to 500 µM, 1.0 nM to 100 µM, 1.0 nM to 50 µM, 1.0 nM to 10 µM, 1.0 nM to 500 nM, 1.0 nM to 100 nM, 1.0 nM to 10 nM, 10 nM to 100 µM, 10 nM to 50 µM, 10 nM to 10 µM, 10 nM to 5 µM, 10 nM to 1 µM, 50 nM to 500 µM, 50 nM to 100 µM, 50 nM to 10 µM, 50 nM to 1 µM, 50 nM to 500 nM, 50 nM to 100 nM, 1 nM to 10 µM, 10 nM to 10 µM, 20 nM to 10 µM, 100 nM to 10 µM, 1 µM to 1 mM, 1 µM to 500 µM, 1 µM to 500 µM, 5 µM to 500 µM, 10 µM to 100 µM, 1 nM to 500 µM, 10 nM to 100 µM, 10 nM to 10 pM, 20 nM to 1 µM, 1 nM to 500 nM, 10 nM to 100 nM, 20 nM to 50 nM, 1 nM to 100 nM, 3 nM to 50 nM toxin.

Dosing can be single dosage or cumulative (serial dosing), and can be readily determined by one skilled in the art. For instance, treatment of a dermal disorder may comprise a one-time administration of an effective dose of a composition disclosed herein. As a non-limiting example, an effective dose of a composition disclosed herein can be administered once to an individual, e.g., as a single injection or deposition at or near the site exhibiting a symptom of a cosmetic disorder. Alternatively, treatment of a cosmetic disorder may comprise multiple administrations of an effective dose of a composition disclosed herein carried out over a range of time periods, such as, e.g., daily, once every few days, weekly, monthly or yearly. As a non-limiting example, a composition disclosed herein can be administered once or twice yearly to an individual. The timing of administration can vary from individual to individual, depending upon such factors as the severity of an individual's symptoms. For example, an effective dose of a composition disclosed herein can be administered to an individual once a month for an indefinite period of time, or until the individual no longer requires therapy. A person of ordinary skill in the art will recognize that the condition of the individual can be monitored throughout the course of treatment and that the effective amount of a composition disclosed herein that is administered can be adjusted accordingly.

Routes of Administration

An active agent (e.g., a Clostridial toxin or a fragment or variant thereof) is administered to an individual using any available method and route suitable for drug delivery, including in vivo and ex vivo methods, as well as systemic and localized routes of administration. In one embodiment, the Clostridial toxin, including fragments or variants thereof, are administered in accordance with established protocols for botulinum toxin therapy. The term "botulinum toxin therapy" encompasses, without limitation, the use of any naturally occurring or modified or engineered form of a botulinum toxin or a domain or fragment thereof, in any formulation, combined with any carrier or active ingredient and administered by any route of administration.

Methods of Use

Cosmetic Applications

In one embodiment, the present disclosure relates to methods for using Clostridial toxins or fragments or variants thereof for cosmetic applications. In one embodiment, the compositions are useful in improving a skin feature or attribute, e.g., clarity, hydration, epidermal and dermal thickness, texture, elasticity, color, tone, pliability, firmness, tightness, smoothness, thickness, radiance, evenness, laxity, complexion, fine lines, wrinkles, pore size, or oiliness.

In another embodiment, the compositions are useful in improving at least 2, at least 3, at least 4, at least 5 or all of the aforementioned features of the skin.

In one embodiment, the composition comprising a Clostridial toxin or a fragment or variant thereof is useful in improving skin clarity of a subject. Skin clarity and/or reduction in freckles and age spots can be evaluated using a Minolta Chromometer. The measurements can be made on each side of the face and averaged, as left and right facial values. Skin clarity can also be measured using a regular Minolta Meter. The measurement is a combination of parameters and is related to skin brightness, and correlates well with skin smoothness and hydration. See, Schwarb et al., *Eur J Pharm Biopharm.*, 47(3): 261-7, 1999.

In another embodiment, the composition comprising Clostridial toxins or a fragment or variant thereof is useful in improving skin elasticity and/or firmness. These parameters can be measured using a Hargens ballistometer, a device that evaluates the elasticity and firmness of the skin by dropping a small body onto the skin and recording its first two rebound peaks. The ballistometry is a small lightweight probe with a relatively blunt tip (4 square mm-contact area). The probe penetrates slightly into the skin and results in measurements that are dependent upon the properties of the outer layers of the skin, including the stratum corneum and outer epidermis and some of the dermal layers. See, Hargens et al., Ballistometry, Handbook of Non-Invasive Methods and the Skin, 359-366, Cit-C Press, New York (1995). Alternately, skin elasticity and/or firmness may be measured with a Cutometer MPA 580 using the methodologies outlined in Bonaparte et al. (*J Med Eng Technol.*, 37(3):208-12, 2013). A representative method involves applying a suction pressure to the skin, at which point, the device (Cutometer) begins to measure the distance the skin deforms over time. The Cutometer provides the elastic resistance (Ue) and viscoelastic resistance (Uv). After some time (e.g., 3 seconds), the Cutometer suction pressure is removed and the maximum deformation of the skin is measured to calculate overall pliability (Uf). The skin then recoils, and the changes are measured by the Cutometer. At the end of the period during which no suction is applied, the initial recoil elastic (Ur) and the total elastic recoil (Ua) are measured, from which, the Uv/Uf, Ua/Uf and Ur/Uf ratios are computed. The Uv/Ue ratio represents the 2 components that resist the stretching of the skin during the suction period. Bonaparte et al. (*JAMA Facial Plast Surg.*, 17(4):256-63, 2015).

In another embodiment, the composition comprising a Clostridial toxin or a fragment or variant thereof is useful in improving skin color, which can be routinely evaluated using a Fitzpatrick scale. See, Fitzpatrick et al., *Archives of Dermatology*, 124 (6): 869-871, 1988.

In another embodiment, the composition comprising a Clostridial toxin or a fragment or variant thereof is useful in improving skin smoothness and/or skin tone. These parameters can be evaluated with clinical grading techniques. Clinical grading of skin smoothness can be analyzed via a ten-point analog numerical scale. Evaluations were made independently by two clinicians and averaged. See, Sonti et al., *Int J Cosmet Sci.*, 35(2), 156-162, 2013.

In another embodiment, the composition comprising a Clostridial toxin or a fragment or variant thereof is useful in reducing skin dryness, which can be evaluated via art-known methods. For example, clinical grading of skin dryness can be determined by a five-point standard Kligman Scale (Kligman et al., *J. Soc. Cosmet. Chem.*, 82, 171-177, 1987). Evaluations can be made independently by two clinicians and averaged.

In another embodiment, the composition comprising a Clostridial toxin or a fragment or variant thereof is useful in improving skin smoothness and/or reducing wrinkles. These parameters can also be assessed visually by using the methods disclosed in Packman et al. (*J. Soc. Cosmetic Chem.*, 29:70, 1978) and Packman et al. (*J. Soc. Cosmetic Chem.*, 29:70, 1978). For example, at each subject visit, the depth, shallowness and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

In another embodiment, the composition comprising a Clostridial toxin or a fragment or variant thereof is useful in improving skin softness/suppleness. These parameters can be evaluated using the gas bearing electrodynamometer, an instrument that measures the stress/strain properties of the skin. See, Maes et al., *Int J Cosmet Sci.*, 5(5):189-200, 1983. The viscoelastic properties of skin correlate with skin moisturization. Measurements can be obtained on a predetermined site, e.g., cheek, by attaching the probe to the skin surface with double-stick tape. A force of approximately 3.5 gm can be applied parallel to the skin surface and the skin displacement is accurately measured. Skin suppleness can then be calculated and is expressed as dynamic spring rate (DSR).

In other non-limiting aspects, the efficacy of the compositions of the present disclosure can be evaluated by using a skin analog, such as, for example, EpiDermFT and MELANODERM™. The analog can be treated with a variety of bases containing the compositions of the disclosure or with a vehicle alone as a control. This test can also be used to confirm the skin exfoliation abilities of the composition.

In practicing the aforementioned cosmetic applications, it is advantageous to use compositions containing Clostridial toxins or fragments or variants thereof which do not produce paralysis of a facial muscle.

In some embodiments, the present disclosure relates to methods for using Clostridial toxins or fragments or variants thereof for reducing skin oiliness. In practicing the methods of the present disclosure, the degree of "oiliness" is normally a function of the amount of sebum secretions on a subject's face or hair. Preferably, a SEBUMETER®, a handheld, electronic diagnostic instrument available from Courage+Khazaka Electronic GmbH (Cologne, Germany) is used to measure "oiliness" based on "grease spot photometry." More specifically, a piece of matte tape is dispensed from a holder, and placed in contact with the surface of the skin or hair. After contact for a specified time interval, the tape becomes transparent in relation to the amount of sebum on the skin or hair. Using a photocell, the amount of light transmission is measured, and correlated with the amount (i.e., degree) of sebum. See, Youn et al., *Skin Res. Technol.*, 8(3), 168-72, 2002. (Other devices for calculating sebum levels, including SEBUTAPE®, or comparable technology (e.g., SEBUFIX®) can also be used.

Alternatively, or in addition to using a SEBUMETER®, "shininess" of skin or light reflection (reflecting "oiliness") can be measured with a visual image analysis software. Herein, an image of the skin is captured, preferably about twenty minutes after washing, and the image is uploaded to, or saved on, an electronic device having an imaging means (e.g., video or still camera), and scored using visual image analysis software (e.g., IMAGEJ, NIH, Bethesda, Md.).

Alternately, oiliness of skin is evaluated using a SEBUTAPE® (CuDerm, Corp., Dallas, Tex., USA). One side of the film is coated with a lipid-porous adhesive, which enables the film to be affixed to the skin during a sampling (i.e., contact) period. As sebum reaches the skin surface, it is rapidly absorbed into the film. Air within the microcavities is displaced by sebum. The sebum-filled cavities, in turn, become transparent. Additionally, sebum output forms a "spot", corresponding in size to the volume of the droplet (Kligman et al., *J. Soc. Cosmet. Chem.*, 37, 369-374, 1986). SEBUFIX® foil, available from Courage+Khazaka (Cologne, Germany), absorbs sebum from the skin surface within the micropores, displaying the sebum as "spots" of different. The foil is mounted on a video camera, which records sebum production over a defined period of time.

"Oiliness" may also be assessed by taking a specimen of bodily fluid (e.g., saliva or mucosal cells lining the oral cavity) or stratum corneum cells obtained by tape stripping methods and measuring the level of expression of one or more genes associated with increased sebum production, as well as measurements that evaluate DNA, RNA, protein or lipid content.

For purposes of the present disclosure, the degree of "oiliness" is preferably differentiated between "slightly oily" or "very oily", where "slightly oily" skin is characterized by an amount of sebum minimally sufficient to create an effective occlusive barrier, a protective coating that prevents entry of allergens and irritants, and limit transepidermal water loss, but not an amount of sebum on the skin's surface that would cause shininess, acne and/or an unpleasant sticky sensation.

Preferably, in addition to one or both of measuring sebum content (preferably, using a SEBUMETER®) or skin shininess (using visual image analysis), oiliness is also assessed using clinically-validated assessment tool (e.g., questionnaire) which may be (a) self-administered by a consumer using an interactive electronic device, a computing device (including tablets or smartphone) or (b) trained skincare professional. Two non-limiting examples of clinically-validated questionnaire are described in the following publications: Baumann, et al., *Journal of Cosmetics, Dermatological Sciences and Applications,* 4, 78-84, 2014; and U.S. Pat. No. 9,724,287 (score between 34-44 indicates "very oily" skin; score between 27-33 indicates "slightly oily" skin).

Alternately, in the context of the present disclosure, skin may be classified as "dry" based skin hydration status, which may be measured based on changes in dielectric constant due to skin surface hydration. Preferably, skin hydration is measured with a CORNEOMETER®, a hand-held probe from Courage+Khazaka Electronics GmbH (Cologne, Germany).

Treatment of Skin Disorders

The skin has two primary layers, the outer epidermis layer, which is made up primarily by keratinocytes and the inter dermis layer, which is made up primary by fibroblasts. The epidermis forms a protective barrier against environmental damage by pathogenic bacteria, fungi, parasites, and viruses, heat, UV radiation and water loss. The dermis provides tensile strength and elasticity to the skin through an extracellular matrix composed of collagen fibrils, microfibrils, and elastic fibers, embedded in hyaluronan and proteoglycans.

Effects on epidermal and dermal cells, including keratinocytes, which produce structural proteins (filaggrin, keratin), enzymes (proteases), lipids and antimicrobial peptides (defensins) and differentiate to create the stratum corneum and skin appendages, e.g., hair follicles and sebaceous glands, fibroblasts, which produce and maintain the extra cellular matrix (ECM) components, including collagens, fibrin, fibronectin, elastin, proteoglycans, glycosaminoglycans, and matricellular proteins, sebocytes, which are derived from differentiated keratinocytes, and make up the sebaceous and meibomian glands that secrete sebum and lubricates and waterproofs the skin, hair and eyes, and melanocytes, which make the pigment melanin of the skin and eyes, could impact for example skin quality attributes, including clarity, hydration, epidermal and dermal thickness, texture, elasticity, color, tone, pliability, firmness, tightness, smoothness, thickness, radiance, evenness, laxity, complexion, fine lines, wrinkles, pore size, or oiliness.

The present disclosure further relates to methods for the use of Clostridial toxins or fragments or variants thereof as treatment for cosmetic disorders of the skin. In one embodiment, the cosmetic skin disorder is a disorder that is caused by an alteration in the function of a sebaceous gland. Sebaceous gland disorders may be caused by overactive sebaceous glands, underactive sebaceous glands, mal-developed sebaceous glands, blocked sebaceous glands, infected sebaceous glands, inflamed sebaceous glands and the like.

Examples of sebaceous gland disorders include, but are not limited to: acne, including open comedos (blackheads) and whiteheads, pimples, deep acne, acne conglobata, acne rosacea, comedos, cysts, microcomedos, papules, *Propionibacterium acnes* (*P. acnes*) infections, pustules, acne vulgaris, rosacea, perioral dermatitis, sebaceous cysts, primary seborrhea (seborrhea oleosa), secondary seborrhea (seborrhea sicca) and alopecia. Also within this definition are disorders treatable by altering the function of a sebaceous gland, such as dandruff and dry skin, and "cosmetic" sebaceous gland disorders, including dry hair, greasy hair, hair and skin sheen and other minor cosmetic disorders of the skin and/or complexion.

In one embodiment, the present disclosure relates to methods for modulating sebum production and/or sebum composition using Clostridial toxins or fragments or variants thereof as described herein. In some embodiments, the modulating causes a change in sebum production and/or sebum composition and whereby causes a change in skin oiliness/dryness. In one embodiment, the modulating reduces sebum production and whereby reduces skin oiliness. In another embodiment, the modulating increases sebum production and whereby reduces skin dryness.

In another embodiment, the present disclosure relates to methods for treating skin disorders associated with sebum dysregulation (reduced or increased production) and/or abnormalities (altered sebum composition) using Clostridial toxins or fragments or variants thereof as described herein. In some embodiments, the present method comprises administering a Clostridial toxin, fragments or variants thereof to a subject in need thereof to modulate sebum production and/or sebum composition, whereby treating the skin disorders associated with sebum dysregulation and/or abnormalities. Exemplary skin disorders associated with sebum dysregulation and/or abnormalities include acne, seborrheic dermatitis, erythema, rosacea, psoriasis, atopic dermatitis (AD), alopecia, vitiligo, allergies, infection, and inflammation.

Sebaceous glands secrete sebum containing antimicrobial peptides, including dermcidin, b-defensins, and psoriasin, and acids that form the acid mantle, a fine, slightly acidic (between pH 4.5 and pH 6.0) film on the surface of the skin that prevents water loss, and provides a barrier against pathogens, such as for example bacteria, yeast, fungi, virus and mite. Sebum dysregulation and/or abnormalities may weaken this barrier and make the skin more susceptible to pathogens. Modulation of sebum production and/or composition could result in improvement of dermal disease associated with compromised skin barrier function, infection, and inflammation. In some embodiments, the present disclosure relates to methods for treating infections associated with sebum dysregulation and/or abnormalities using Clostridial toxins or fragments or variants thereof as described herein. Exemplary infections treatable by the present methods include infections from bacteria, including *Propionibacterium acnes, Staphylococcus aureus* (MRSA), leprosy (*Mycobacterium leprae*), and Cellulitis (*Streptococcus* and *Staphylococcus*); viruses, including shingles (Varicella-zoster), warts (papillomaviruses (HPV)), and herpes simplex; fungi, including *Trichophyton, Epidermophyton, Microsporum,* and *Vibrio vulnificus*; yeasts, including *Malassezia,* lice; and mites, including *Demodex* and *Sarcoptes scabiei.*

EXAMPLES

The structures, materials, compositions, and methods described herein are intended to be representative examples of the disclosure, and it will be understood that the scope of the disclosure is not limited by the scope of the examples. Those skilled in the art will recognize that the disclosure may be practiced with variations on the disclosed structures, materials, compositions and methods, and such variations are regarded as within the ambit of the disclosure.

Example 1

Effect of an Exemplary Polypeptide Provided in Accordance with Aspects of the Present Disclosure on Cellular Gene Expression in Normal Human Primary Fibroblasts Treatment of normal human primary fibroblasts with of a polypeptide having an amino acid sequence substantially identical to the amino acid sequence of the binding domain of BoNT/A ($H_C$/A) for 1, 2, or 3 days resulted in significant time-dependent changes in expression of 10 fibroblast genes based on qPCR. Briefly, Human Dermal Fibroblasts, adult (HDFa) (cellResearchCorp Pte Ltd) were cultured in MEM medium containing 2% FBS for 2 weeks before treatment with 1 µM of a polypeptide having SEQ ID NO: 19 for 1, 2 or 3 days. Time-dependent expression of genes known to be expressed in fibroblasts and involved with extracellular matrix (ECM) organization or epidermal self-renewal (keratinocyte stem cell factor) was evaluated. Total RNA was isolated using RNAqueous kit from Ambion and cDNA was generated with Qiagen reagents following manufacturer's protocol. Real-time qPCR was performed using the Bio-Rad PCR Array. Changes in gene expression were calculated as fold change over the untreated buffer control at each time point ($\Delta\Delta CT=\Delta CT$ (Gene (test)–GAPDH (test))–$\Delta CT$ (Gene (untreated control)–GAPDH (untreated control)); Fold Change=2(–$\Delta\Delta CT$)). Fold changes greater than 2 or less than 0.5 (p-value≤0.05) were considered relevant significant changes. Exemplary genes showing a time-dependent change are shown in FIG. 1, which is a bar graph showing the fold-change in expression of the indicated genes in normal human primary fibroblast cells after treatment with 1 µM of a polypeptide having an amino acid sequence substantially identical to the amino acid sequence of the binding domain of BoNT/A ($H_C$/A) for 1, 2 or 3 days, where the fold-change is expressed relative to untreated control cells. The results show that treatment of primary human dermal fibroblasts with a polypeptide having an amino acid sequence substantially identical to the amino acid sequence of the binding domain of BoNT/A ($H_C$/A), resulted in time-dependent gene expression changes. Specifically, initial increased expression (Day 1 and 2) of the genes encoding matrix degrading enzymes like matrix metalloproteinases (MMPs) and proteins like TP63 (Transformation-related protein 63, a transcription factor identifying corneal and epidermal stem cells) (fold-changes from Day 1 to Day 3, MMP1: from 11- to 3-fold, MMP3: from 5- to 4-fold, TP63: from 44- to 25-fold), followed by (Day 3) increased expression of genes encoding major matrix structure proteins like collagen and elastin (fold-changes from Day 1 to Day 3, COL1A1: from 2- to 3-fold, COL1A2: from 2- to 3-fold, COL3A1: from 2- to 3-fold, ELN: from 2- to 6-fold), suggests that the fibroblasts underwent extracellular matrix (ECM) re-modeling. Re-modeling of the ECM is expected to affect structural and functional characteristics of the skin dermis, resulting in changes in biomechanical properties of the skin, such as for example elasticity and pliability. The results therefore suggest that polypeptides corresponding substantially to the binding domain of BoNT/A ($H_C$/A) could affect the structure and function of the skin dermis in human patients, specifically structural and functional characteristics of the skin dermis, including the extracellular matrix structure, resulting in changes in biomechanical properties of the skin, such as for example elasticity and pliability.

Example 2

Figure 2:
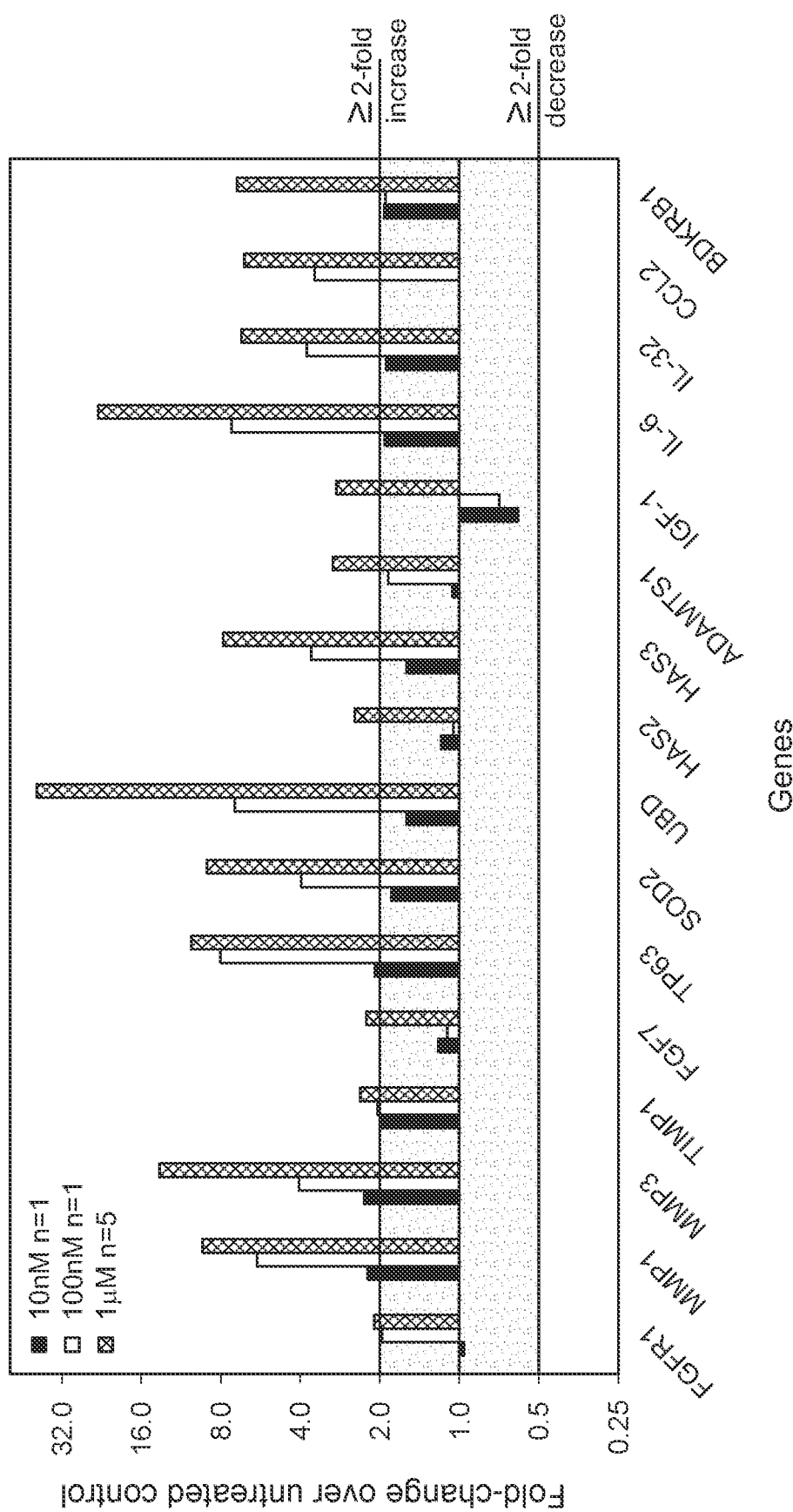
FIG. 2 is a bar graph showing the fold-change in expression of the indicated genes in normal human primary fibroblast cells after treatment with 10 nM (solid bar), 100 nM (unfilled bar) or 1 µM (hatched bar) of the exemplary polypeptide of SEQ ID NO: 19 for 24 hours, where the fold-change is expressed relative to untreated control cells.

Effect of the Exemplary Polypeptide of SEQ ID NO: 19 on Cellular Gene Expression in Normal Human Primary Fibroblasts Treatment of normal human primary fibroblasts with 10 nM, 100 nM or 1 µM of a polypeptide having an amino acid sequence substantially identical to the amino acid sequence of the binding domain of BoNT/A ($H_C$/A) for 1 day (24 hours) resulted in significant dose-dependent changes in expression of 16 fibroblast-related genes based on qPCR. Briefly, Human Dermal Fibroblast, adult (HDFa) (ThermoFisher Scientific, Cat. No. C0135C) were cultured in MEM medium containing 2% FBS for 2 weeks before treatment with 10 nM, 100 nM or 1 µM of a polypeptide of SEQ ID NO: 19 for 1 day (24 hours). Expression of genes known to be expressed in fibroblasts and involved with ECM organization, inflammation, or epidermal self-renewal were evaluated. cDNA was generated by reverse transcription using SUPERSCRIPT VILO cDNA Synthesis Kit (Thermo Scientific #11754050) and further diluted in TAQMAN Fast Advanced Master Mix (Thermo Scientific #4444557) before transfer to designated wells in TAQMAN Fast plates (Thermo Scientific #4413259). Real-time qPCR was performed using the Applied Biosystems 7500 Fast Real-Time PCR system (Thermo Fisher Scientific). Changes in gene expression were calculated as fold change over the untreated control at each time point ($\Delta\Delta CT=\Delta CT$ (Gene (test)–GAPDH (test))–$\Delta CT$ (Gene (untreated control)–GAPDH (untreated control)); Fold Change=2(–$\Delta\Delta CT$)). Fold changes greater than 2 or less than 0.5 (p-value≤0.05) were considered relevant significant changes. Exemplary genes showing a dose-dependent change are shown in FIG. 2, which is a bar graph showing the fold-change in expression of the indicated genes in normal human primary fibroblast cells after treatment with 10 nM (solid bar), 100 nM (no fill bar) or 1 µM (hatched bar) of a polypeptide having an amino acid sequence substantially identical to the amino acid sequence of the binding domain of BoNT/A ($H_C$/A) for 24 hours, where the fold-change is expressed relative to untreated control cells. Notably, expression of genes known to be involved with tissue and ECM homeostasis, re-modeling, renewal, and repair were increased. The results suggest that polypeptides corresponding substantially to the binding domain of BoNT/A ($H_C$/A) could affect the structure and function of the skin dermis in human patients, specifically structural and functional characteristics of the skin dermis, including the extracellular matrix structure, resulting in changes in biomechanical properties of the skin, such as for example elasticity and pliability.

Example 3

Figure 3:
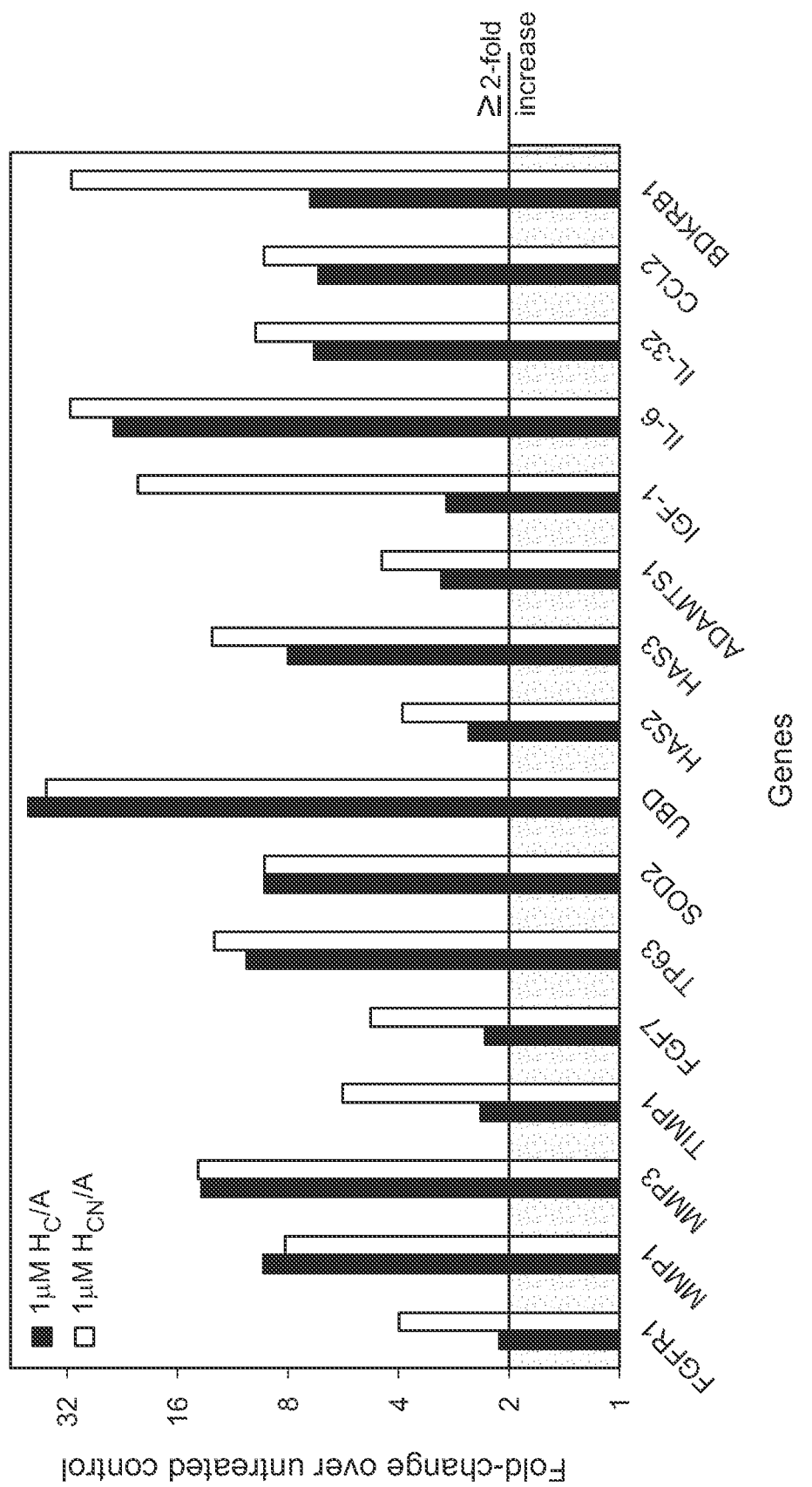
FIG. 3 is a bar graph showing the fold-change in expression of the indicated genes in normal human primary fibroblast cells after treatment with 1 µM of the exemplary polypeptide of SEQ ID NO: 19 (solid bar) or 1 µM of another exemplary polypeptide provided in accordance with aspects of the present disclosure, having an amino acid sequence of SEQ ID NO: 21 (unfilled bar).

Effect of Exemplary Polypeptides Provided in Accordance with Aspects of the Present Disclosure on Cellular Gene Expression in Normal Human Primary Fibroblasts Treatment of normal human primary fibroblasts with 1 µM of a polypeptide having an amino acid sequence substantially identical to the amino acid sequence of the binding domain of BoNT/A ($H_C$/A) or a polypeptide having an amino acid sequence substantially identical to the N-terminal half of the binding domain of BoNT ($H_{CN}$/A) resulted in similar significant changes in expression of 16 fibroblast-related genes based on qPCR. Briefly, Human Dermal Fibroblast, adult (HDFa) (ThermoFisher Scientific, Cat. No. C0135C) were cultured in MEM medium containing 2% FBS for 2 weeks before treatment with 1 µM of a polypeptide having SEQ ID NO.: 19 or a polypeptide having SEQ ID NO. 21 for 1 day (24 hours). Expression of fibroblast-related genes, known to be involved with ECM organization, inflammation, or epidermal self-renewal was evaluated. cDNA was generated by reverse transcription using SUPERSCRIPT VILO cDNA Synthesis Kit (Thermo Scientific #11754050) and further diluted in TAQMAN Fast Advanced Master Mix (Thermo Scientific #4444557) before transfer to designated wells in TAQMAN n Fast plates (Thermo Scientific #4413259). Real-time qPCR was performed using the Applied Biosystems 7500 Fast Real-Time PCR system (Thermo Fisher Scientific). Changes in gene expression were calculated as fold change over the untreated control at each time point ($\Delta\Delta CT = \Delta CT$ (Gene (test)–GAPDH (test))–$\Delta CT$ (Gene (untreated control)–GAPDH (untreated control)); Fold Change=$2(-\Delta\Delta CT)$). Fold changes greater than 2 or less than 0.5 (p-value≤0.05) were considered relevant significant changes. Results are shown in FIG. 3, which is a bar graph showing the fold-change in expression of the indicated genes in normal human primary fibroblast cells after treatment with 1 µM of a polypeptide having an amino acid sequence substantially identical to the amino acid sequence of the binding domain of BoNT/A ($H_C$/A) (solid bar) or with 1 µM of a polypeptide having an amino acid sequence substantially identical to the N-terminal half of the binding domain of BoNT ($H_{CN}$/A) (no fill bar). The results show that both polypeptides, corresponding substantially to the binding domain of BoNT/A ($H_C$/A) and the N-terminal half of the binding domain ($H_{CN}$/A), respectively, were equally effective in affecting expression of fibroblast-related genes; FGFR1, MMP1, MMP3, TIMP1, FGF7, TP63, SOD2, UBD, HAS2, HAS3, ADAMTS1, IGF-1, IL-6, IL-32, CCL2, and BDKRB1. The results suggest that polypeptides corresponding substantially to the binding domain of BoNT/A ($H_C$/A) or the N-terminal half of the binding domain ($H_{CN}$/A) could affect the structure and function of the skin dermis in human patients, specifically structural and functional characteristics of the skin dermis, including the extracellular matrix structure, resulting in changes in biomechanical properties of the skin, such as for example elasticity and pliability.

Example 4

Figure 4B:
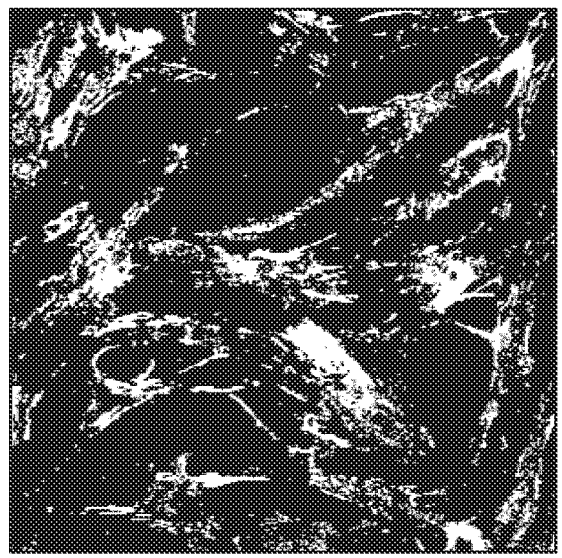
FIGS. 4A-4B are images of fibroblast cells immunostained for fibronectin with an antibody to fibronectin and cultured for 48 hours in either normal growth medium or in step-down medium (medium with 250 µg/ml BSA) in the presence (FIG. 4A) or absence (FIG. 4B) of the exemplary polypeptide of SEQ ID NO: 19.
Figure 4A:
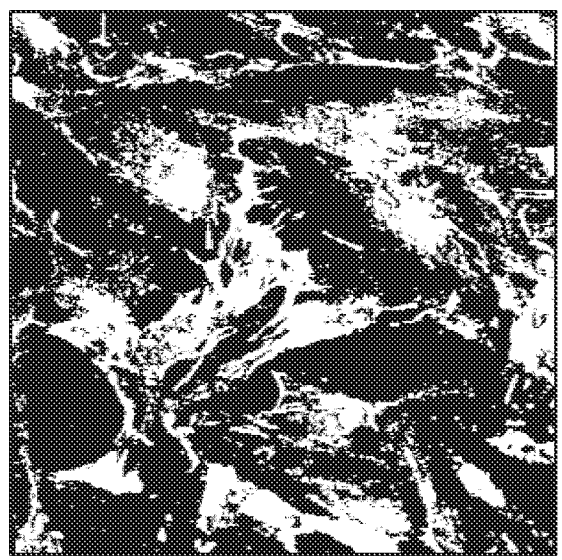

Effect of the Exemplary Polypeptide of SEQ ID NO: 19 on Cellular Expression of Fibronectin Treatment of keloid human primary fibroblasts with 600 pM of a polypeptide having an amino acid sequence substantially identical to the amino acid sequence of the binding domain of BoNT/A ($H_C$/A) increased expression of fibronectin glycoprotein based on Immunohistochemistry (IHC). Briefly, keloid derived fibroblast cells were cultured for 48 hours (2 days) in step-down medium (medium with 250 µg/ml BSA, Sigma #7030) with or without treatment with 600 pM of a polypeptide having SEQ ID NO.: 19. Immunostaining for fibronectin was performed with antibody to fibronectin (Abcam, #ab2413). Representative images are shown in FIGS. 4A-4B, which show images of fibroblast cells with (FIG. 4A) or without (FIG. 4B) a polypeptide having an amino acid sequence substantially identical to the amino acid sequence of the binding domain of BoNT/A ($H_C$/A). The results show that treatment of fibroblast cells with a polypeptide having an amino acid sequence substantially identical to the amino acid sequence of the binding domain of BoNT/A ($H_C$/A) increased fibronectin expression. The results suggest that polypeptides corresponding substantially to the binding domain of BoNT/A ($H_C$/A) could increase expression of fibronectin in the dermis of human patient skin, resulting in changes in extracellular matrix structure and biomechanical properties of the skin, such as for example elasticity and pliability.

Example 5

Figure 5:
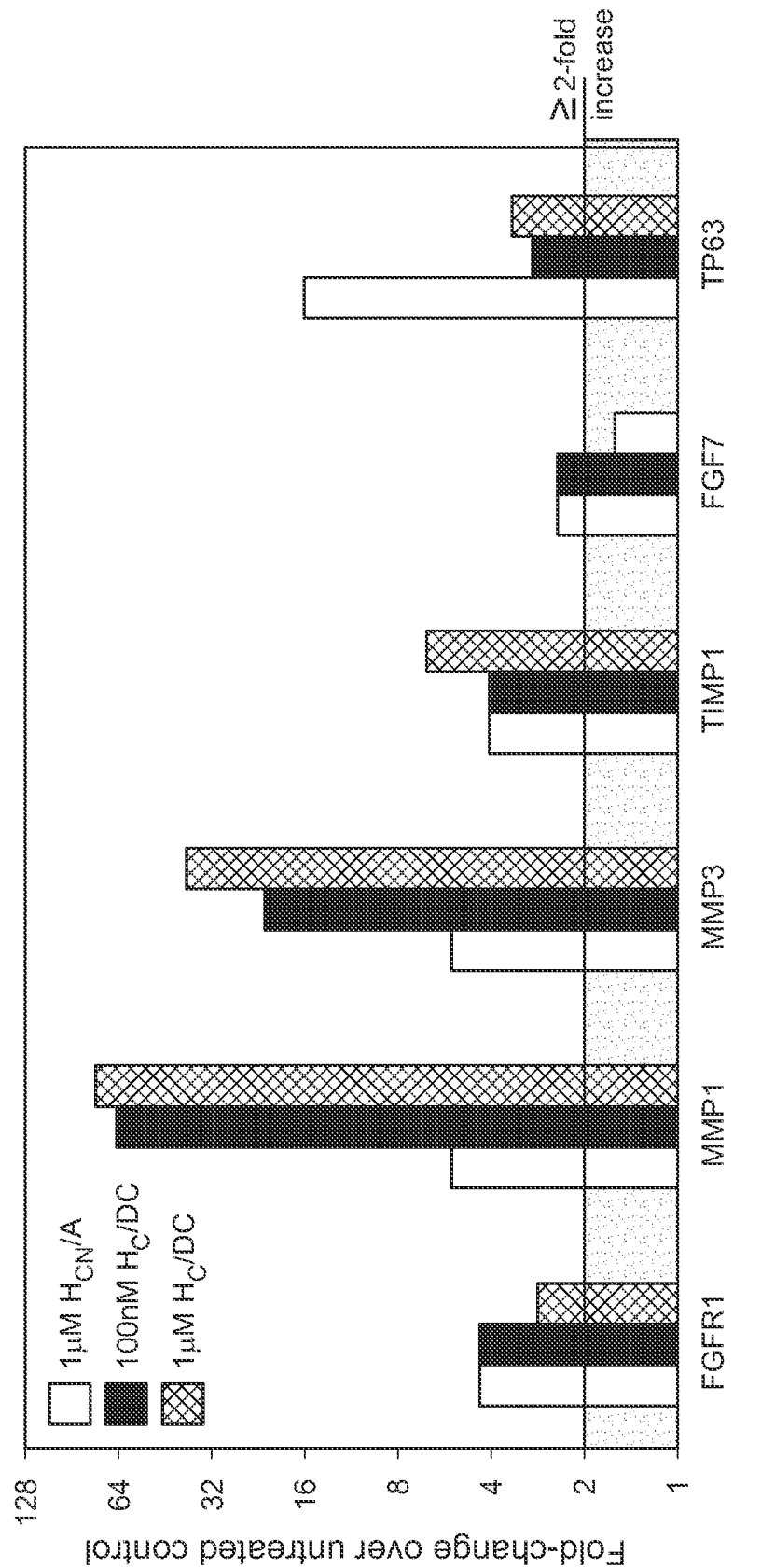
FIG. 5 shows gene expression changes in normal human primary fibroblasts treated with 100 nM or 1 µM of another exemplary polypeptide provided in accordance with aspects of the present disclosure having an amino acid sequence of SEQ ID NO: 20 or with 1 µM of the exemplary polypeptide of SEQ ID NO: 21 for 1 day.

Effect of Exemplary Polypeptides Provided in Accordance with Aspects of the Present Disclosure on Gene Expression in Fibroblast Cells Treatment of normal human primary fibroblasts with 100 nM or 1 µM of a polypeptide having an amino acid sequence substantially identical to the amino acid sequence of the binding domain of BoNT/DC ($H_C$/DC) or 1 µM of a polypeptide having an amino acid sequence substantially identical to the N-terminal half of the binding domain of BoNT/A ($H_{CN}$/A) resulted in significant changes in expression of 6 fibroblast-related genes based on qPCR. Briefly, Human Dermal Fibroblast cells (HDFa) (ThermoFisher Scientific, Cat. No. C0135C) were cultured in MEM medium containing 2% FBS for 2 weeks before treatment with 100 nM or 1 µM of a polypeptide of SEQ ID NO.: 20, or 1 µM of a polypeptide of SEQ ID NO.:21 for 1 day (24 hours). Expression of 6 genes that showed increased expression after treatment with $H_C$/A or $H_{CN}$/A (see, Example 2 and 3, above) were evaluated. cDNA was generated by reverse transcription using SUPERSCRIPT VILO cDNA Synthesis Kit (Thermo Scientific #11754050) and further diluted in TAQMAN Fast Advanced Master Mix (Thermo Scientific #4444557) before transfer to designated wells in TAQMAN Fast plates (Thermo Scientific #4413259). Real-time qPCR was performed using the Applied Biosystems 7500 Fast Real-Time PCR system (Thermo Fisher Scientific). Changes in expression of the following genes were analyzed: FGFR1, MMP1, MMP3, TIMP1, FGF7, and TP63. Changes in gene expression were expressed as fold change over the untreated control at each time point ($\Delta\Delta CT = \Delta CT$ (Gene (test)–GAPDH (test))–$\Delta CT$ (Gene (untreated control)–GAPDH (untreated control)); Fold Change=$2(-\Delta\Delta CT)$). Fold changes greater than 2 or less than 0.5 (p-value≤0.05) is considered relevant significant changes. Results are shown in FIG. 5, which is a bar graph showing the fold-change in expression of the indicated genes in normal human primary fibroblast cells after treatment with 1 µM of a polypeptide having an amino acid sequence substantially identical to the N-terminal half of the binding domain of BoNT ($H_{CN}$/A) (no fill) or 100 nM (solid fill) or 1 µM (hatched fill) of a polypeptide having an amino acid sequence substantially identical to the binding domain of BoNT/DC ($H_C$/DC) for 1 day (24 hours). The results show that treatment with 100 nM or 1 µM of a polypeptide corresponding substantially to the binding domain of BoNT/DC ($H_C$/DC) affects expression of genes in normal human dermal fibroblasts. The effect is similar, or more, to the effect of 1 µM of a polypeptide corresponding substantially to the binding domain of the N-terminal half of $H_C$/A ($H_{CN}$/A), suggesting that polypeptides corresponding substantially to the binding domain of BoNT/DC ($H_C$/DC) are equally, or more, effective, compared to polypeptides corresponding substantially to the binding domain of the N-terminal half of $H_C$/A ($H_{CN}$/A), in affecting expression of fibroblast related genes. The results therefore suggest that polypeptides corresponding substantially to the binding domain of BoNT/DC ($H_C$/DC) could affect the structure and function of the skin dermis in human patients, including the extracellular matrix structure, which for example determines the biomechanical properties of the skin, including elasticity and pliability. The observation that polypeptides corresponding substantially to the binding domains of two different BoNT serotypes affect fibroblasts, also suggests that other additional BoNT serotypes could affect human skin.

Using a sequence alignment software tool, pairwise sequence alignment was performed between different BoNT serotypes; wherein the amino acid sequence of the binding domain of BoNT/A1 ($H_C$/A) (SEQ ID NO: 1) (GENBANK # AF488749) was aligned with the amino acid sequence of the binding domain from the following BoNT proteins: BoNT/B1 (GENBANK #BAE48264): BoNT/C1 (GENBANK # P18640); BoNT/D (GENBANK # P19321); BoNT/DC (GENBANK # EF378947); BoNT/E (GENBANK # AFV91344); BoNT/F (GENBANK #ABS41202); and BoNT/G (GENBANK # X74162). The results, which are shown in Table 2, revealed that the percent identity and homology at the amino acid levels between BoNT/A1 and other BoNT serotypes, e.g., B1, C1, DC, E, F, and G, is similar to the percent identity and homology between BoNT/A1 and BoNT/DC. Specifically, according to the BLAST alignment $H_C$/A and $H_C$/DC are 33% identical and 54% similar (consensus) at the amino acid residue level, which is similar to all the other serotypes (31-51% identical and 49-67% similar (consensus)). As shown in Example 5, the binding domain of BoNT/DC ($H_C$/DC) was as effective as binding domain of BoNT/A in affecting expression of fibroblast-related genes. Thus, the BLAST alignment and the results obtained from Example 5 suggest that other BoNT serotypes, in addition to BoNT/A and BoNT/DC, can affect human skin.

is presented, the search would have to encompass an amino acids space of $2^{283}$ (or $2 \times 10^{85}$) units. Thus, the higher the bit score, the more highly significant the match.

Example 6

Test of Different Lipogenic Stimuli on Sebocyte Cells

Figure 6:
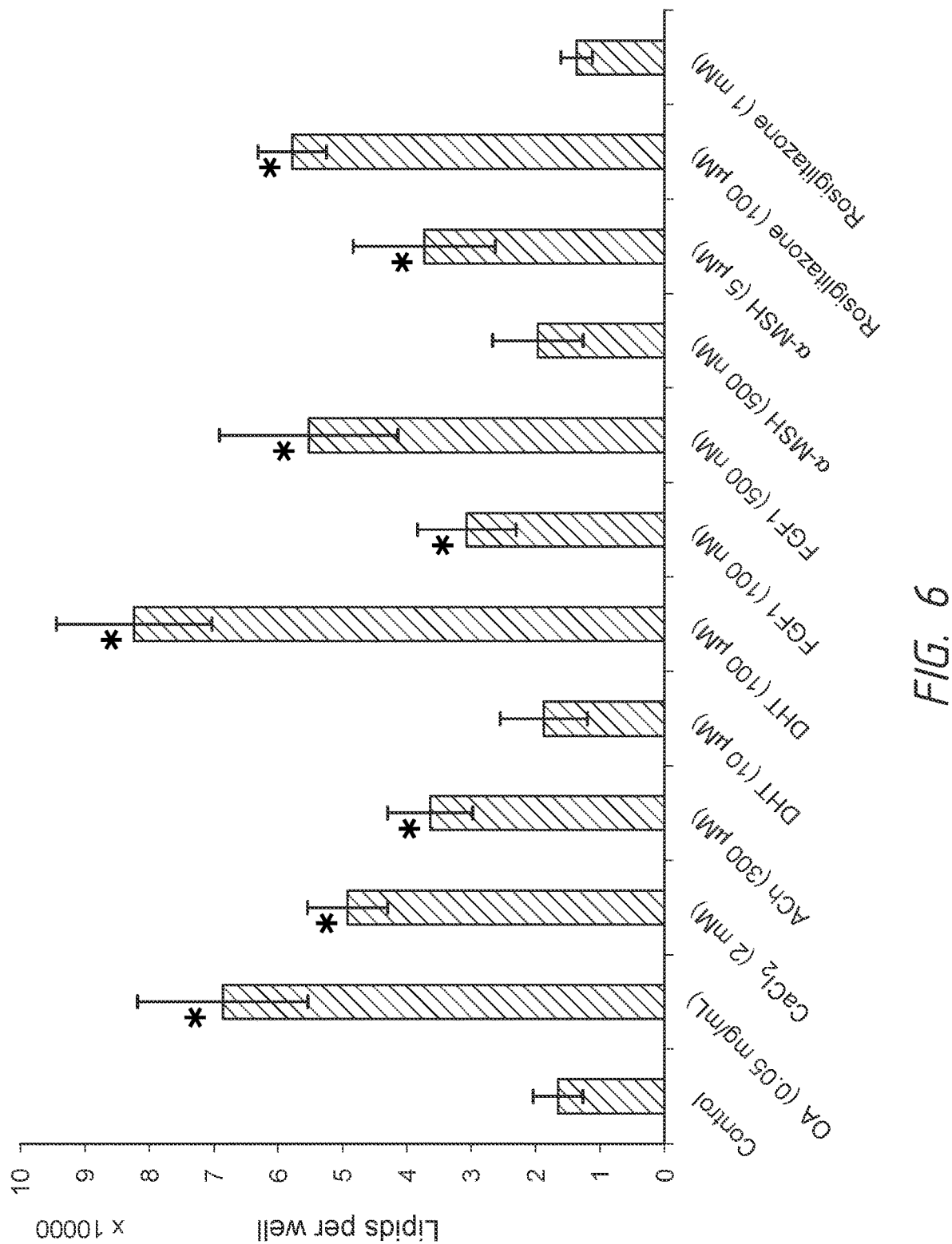
FIG. 6. is a graph showing increase in sebocyte lipogenesis upon treatment of sebocyte cells (SEB-1) with different lipogenic stimuli, including oleic acid (OA), calcium chloride (CaCl$_2$), Acetylcholine (ACh), Dihydrotestosterone (DHT), fibroblast growth factor 1 (FGF1), α-Melanocyte-stimulating hormone (α-MSH), or Rosiglitazone, for 1 day. The * indicates statistical significance of p<0.05 compared to control.

Treatment of sebocyte cells (SEB-1) with different lipogenesis enhancing stimuli increased sebocyte lipogenesis based on Nile Red staining. Briefly, human immortalized sebocyte cells (SEB-1) were cultured in sebocyte growth medium (Zen-Bio®). Various lipogenesis enhancing stimuli were added to the growth medium for 1 day, including: oleic acid (OA) (0.05 mg/mL), calcium chloride ($CaCl_2$)) (2 mM), acetylcholine (ACh) (300 µM), dihydrotestosterone (DHT) (10 or 100 µM), fibroblast growth factor 1 (FGF1) (100 nM or 500 nM), α-Melanocyte-stimulating hormone (α-MSH) (500 nM or 5 µM), or rosiglitazone (100 µM or 1 mM). The total amount of sebum lipids per well was measured using a Nile Red lipid droplets fluorescence assay (Cayman Chemical, Cat. #500001), wherein the cells were fixed with 10% formalin and then incubated with Nile Red staining solution and fluorescence intensities (Nile red, FITC, ex/em 485/535 nm) were measured using a fluorescent plate reader (Hidex Plate CHAMELEON™ V multilabel microplate reader, Bioscan, Inc). The results shown in FIG. 6, demonstrate that all the tested lipogenesis enhancing stimuli significantly increased sebocyte lipogenesis, with the following rank order of lipogenic potency; DHT (100 µM, 5.5-fold)>OA (0.025 mg/mL, 4.5-fold)>Rosiglitazone (100 µM, 4-fold) >FGF1 (500 nM, 3.5-fold)>$CaCl_2$ (2 mM, 3-fold)>ACh (300 µM, 2.5-fold)>α-MSH (5 µM, 2-fold) (fold-change relative to untreated control). It should be noted that among the tested stimuli, 1 mM of Rosiglitazone caused cell death, and 500 nM of FGF1 (a native ligand for FGFRs) stimulated sebocyte lipogenesis.

TABLE 2

Pairwise multiple sequence alignment between HC proteins derived from various BoNT serotypes using BLAST.

| Comparison | Variant (Strain) | Tool | Identity (%) | Consensus (%) | Homology (%)* | Gaps (%) | Score** |
|---|---|---|---|---|---|---|---|
| $H_C$/A (Hall A) | $H_{CN}$/A (Hall A) | BLAST | 218/218(100%) | 218/218(100%) | 51.78 | 0/218(0%) | 435 bits(1118) |
|  | $H_{CN}$/A 40-mer (Hall A) |  | 40/40(100%) | 40/40(100%) | 9.50 | 0/40(0%) | 82.0 bits(201) |
|  | $H_C$/B (Okra) |  | 176/440(40%) | 257/440(58%) | 61.05 | 37/440(8%) | 283 bits(723) |
|  | $H_C$/C (Stockholm) |  | 136/442(31%) | 217/442(49%) | 51.54 | 49/442(11%) | 166 bits(420) |
|  | $H_C$/D (D-1873) |  | 137/434(32%) | 226/434(52%) | 53.68 | 40/434(9%) | 182 bits(461) |
|  | $H_C$/DC (VPI 5995) |  | 117/350(33%) | 189/350(54%) | 44.89 | 30/350(8%) | 166 bits(421) |
|  | $H_C$/E (CDC41648) |  | 202/424(48%) | 272/424(64%) | 64.61 | 26/424(6%) | 330 bits(846) |
|  | $H_C$/F (Langeland) |  | 214/422(51%) | 286/422(67%) | 67.93 | 19/422(4%) | 395 bits(1014) |
|  | $H_C$/G (11330) |  | 176/436(40%) | 247/436(56%) | 58.67 | 26/436(5%) | 273 bits(698) |

*The percent homology is defined as the percent of either identical or similar residues (Consensus) within a protein sequence relative to a reference protein sequence divided by the length of the reference sequence
**The ( ) score is the raw score directly computed using the matrix of residue substitution. The bit score is a normalized score which considered the sequence length and gap size. For example, 283 bits means to find a better alignment than the one you found, you have to search 2^283 amino acids space.

As shown in Table 2, the level of alignment between different BoNT serotypes is very high, as indicated by the score. The score is provided either in the form of a raw score or a bit score, wherein the raw score is directly computed by the tool using the matrix of residue substitution and the bit score is a normalized score, which considers the sequence length and gap size. As is understood in bioinformatics, a score of 283 bits means to find a better alignment than what Example 7

Use of an Exemplary Polypeptide Provided in Accordance with Aspects of the Present Disclosure to Inhibit Production of Sebum Lipids Co-treatment of sebocyte cells (SZ95) with the lipogenesis enhancing stimuli oleic acid (OA) and 20 pM a polypeptide having an amino acid sequence substantially identical to the amino acid sequence of the binding domain of BoNT/A ($H_C/A$) reduced the ability of OA to induce lipogenesis. Briefly, Human immortalized sebocyte cells (SZ95) were cultured in sebocyte growth medium (ZEN-BIO®). The following treatments were added to the growth medium for 1 day: control (no treatment); oleic acid (OA) (0.125 mg/mL or 0.25 mg/mL); the exemplary polypeptide of SEQ ID NO: 19 (20 pM); oleic acid (OA) (0.125 mg/mL or 0.25 mg/mL) and polypeptide of SEQ ID. NO.:19 (20 pM). The total amount of sebum lipids was measured using a Nile Red lipid droplets fluorescence assay (Cayman Chemical, Cat. #500001), wherein the cells were fixed with 10% formalin and then incubated with Nile Red staining solution. As a measure for cell number, DAPI staining (1.5 ng/mL final concentration) was performed in parallel. Fluorescence intensities (Nile red, FITC, excitation/emission 485/535 nm, DAPI, excitation: 358 nm; emission: 461 nm) were measured using a fluorescent plate reader (ENVISION 2102, Perkin Elmer). The lipid values were normalized to the DAPI values and graphed as "Lipids per cell (Nile red/DAPI)."

Figure 7:
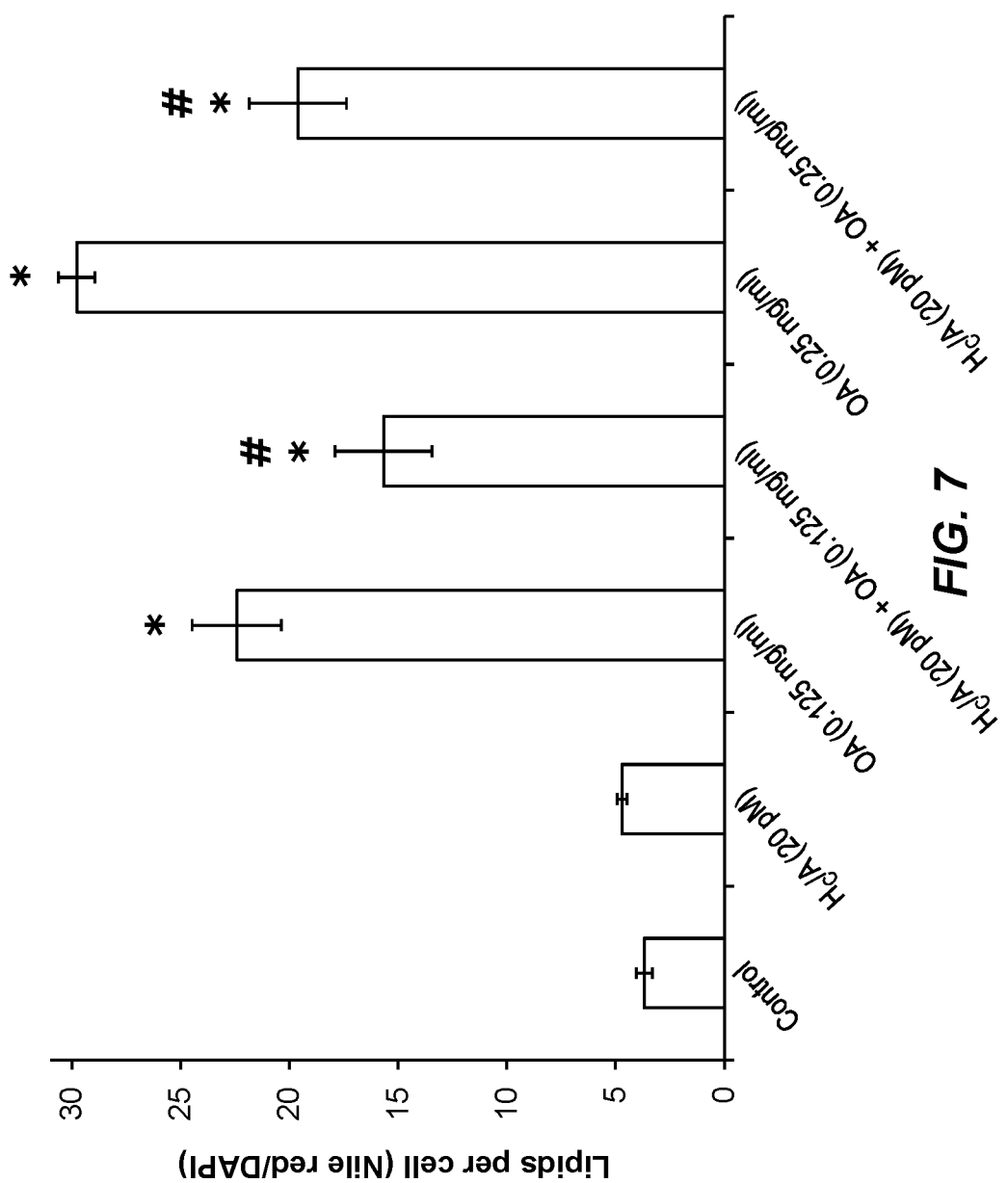
FIG. 7 is a graph showing increase in sebocyte lipogenesis upon treatment of sebocyte cells (SZ95) with oleic acid (OA) and reduction in sebocyte lipogenesis upon co-treatment with 20 pM of the exemplary polypeptide of SEQ ID NO: 19. The * indicates statistical significance of p<0.05 compared to the control. The # indicates statistical significance of p<0.05 compared treatment with OA alone.

The results, shown in FIG. 7, demonstrate that sebum lipogenesis was significantly enhanced by oleic acid (OA) treatment (6-8-fold, dependent on the dose of OA). However, co-treatment of the cell with 20 pM of an exemplary polypeptide having an amino acid sequence substantially identical to the amino acid sequence of the binding domain of BoNT/A ($H_C/A$) (of SEQ ID NO: 19) significantly reduced the lipogenesis enhancement effect of OA (reduction of approximately 30-35%, dependent on the dose of OA). Treatment of the cells with 20 pM of the exemplary polypeptide of SEQ ID NO: 19 alone did not affect sebum lipogenesis. The results suggest that polypeptides corresponding substantially to the binding domain of BoNT/A ($H_C/A$) can affect sebocyte cells and potentially reduce sebum lipogenesis and skin oiliness in human patients.

Example 8

Use of an Exemplary Polypeptide Provided in Accordance with Aspects of the Present Disclosure to Improve Fine Lines and Laxity A 45-year female with photo type II skin wants to minimize signs of photo-aged facial skin, including fine lines and laxity. She declines fractional laser treatment to improve the quality of her skin, due to the associated down-time. Instead, she requests intradermal treatment with a polypeptide having an amino acid sequence which is at least 90% identical to the binding domain of BoNT/A ($H_C/A$). Before treatment, a topical anesthetic cream (2.5% lidocaine and 2.5% prilocaine) is applied on the skin 30 min before treatment and then completely removed.

The polypeptide powder is dissolved in saline (4.5 ng vacuum-dried powder was reconstitution in 9 mL of sterile 0.9% saline) to constitute a solution at 0.5 ng/mL and injects into her facial skin using a multi-needle dermal injector system. A total of 1.3 ng is injected with 2 µL (0.001 ng) at each injection site (1300 sites total). The injected depth is 0.8 mm in the upper face, and 1.0 mm in the middle and lower face, with an interval of 2 mm.

Evaluation is conducted at baseline and at 12 weeks' post-treatment.

Compared to baseline, at 12 weeks' post-treatment, her facial skin shows higher physician's global assessment and subject satisfaction score, with significant improvement in roughness, hydration, skin elasticity, and trans-epidermal water loss (TEWL). This improvement is consistent with experimental data described in Examples 1 and 2, wherein fibroblasts treated with a polypeptide corresponding to the binding domain of BoNT/A ($H_C/A$) were shown to have increased expression of proteins and factors, including fibronectin, collagen and elastin, that function to properly maintain, renew and repair extracellular matrix (ECM) dermal structures.

Example 9

Use of an Exemplary Polypeptide Provided in Accordance with Aspects of the Present Disclosure to Reduce Oiliness, Sebum and Pore Size A 35-year male with phototype III skin has oily forehead (seborrhea) and receives intradermal treatment with a polypeptide having an amino acid sequence which is at least 90% identical to the binding domain of BoNT/A ($H_C/A$).

The polypeptide powder is dissolved in saline, 4.5 ng vacuum-dried powder is dissolved in 0.25 mL of sterile 0.9% saline to constitute a solution at 1.8 ng/0.1 mL, and injected into his forehead. A total of 1.8 ng is injected. Ten (10) injection sites are chosen and 0.18 ng of $H_C/A$ polypeptide is injected intradermally (ID) at each site using a 30-G needle. An ice pack is applied after treatment.

Evaluation is conducted at baseline and at 12 weeks' post-treatment and the amount of sebum is measured using a sebumeter.

Compared to baseline, at 12 weeks' post-treatment, his forehead shows higher physician's global assessment and the patient reported that he was satisfied with the result, with significant reduction in oiliness, sebum and pore size, Percentage (%) reduction in sebum is measured by sebumeter. This improvement is consistent with experimental data described in Examples 6 and 7, wherein sebocytes treated with a polypeptide corresponding to the binding domain of BoNT/A ($H_C/A$) were shown to have reduced oleic acid induced sebum lipogenesis, which would result in reducing skin oiliness.

Example 10

Use of an Exemplary Polypeptide Provided in Accordance with Aspects of the Present Disclosure to Modulate Production of Sebum Lipids Treatment of sebocyte cells (SEB-1) with a polypeptide having an amino acid sequence substantially identical to the amino acid sequence of the binding domain of BoNT/A ($H_C/A$) modulated lipogenesis. Briefly, human immortalized sebocyte cells (SEB-1) were cultured in sebocyte growth medium (Zen-Bio®). The following treatments were added to the growth medium for 1 day: control (no treatment); the exemplary polypeptide of SEQ ID NO: 19 (20 pM); oleic acid (OA) (0.05 mg/mL); oleic acid (OA) (0.05 mg/mL) and polypeptide of SEQ ID. NO.:19 (20 pM). The total amount of sebum lipids was measured using a Nile Red lipid droplets fluorescence assay (Cayman Chemical, Cat. #500001), wherein the cells were fixed with 10% formalin and then incubated with Nile Red staining solution. Fluorescence intensities (Nile red, FITC, excitation/emission 485/535 nm, DAPI, excitation: 358 nm; emission: 461 nm) were measured using a fluorescent plate reader (Hidex Plate CHAMELEON™ V multilabel microplate reader, Bioscan, Inc). The lipid values were normalized to the DAPI values and graphed as "Lipids per cell (Nile red/DAPI)."

Figure 8:
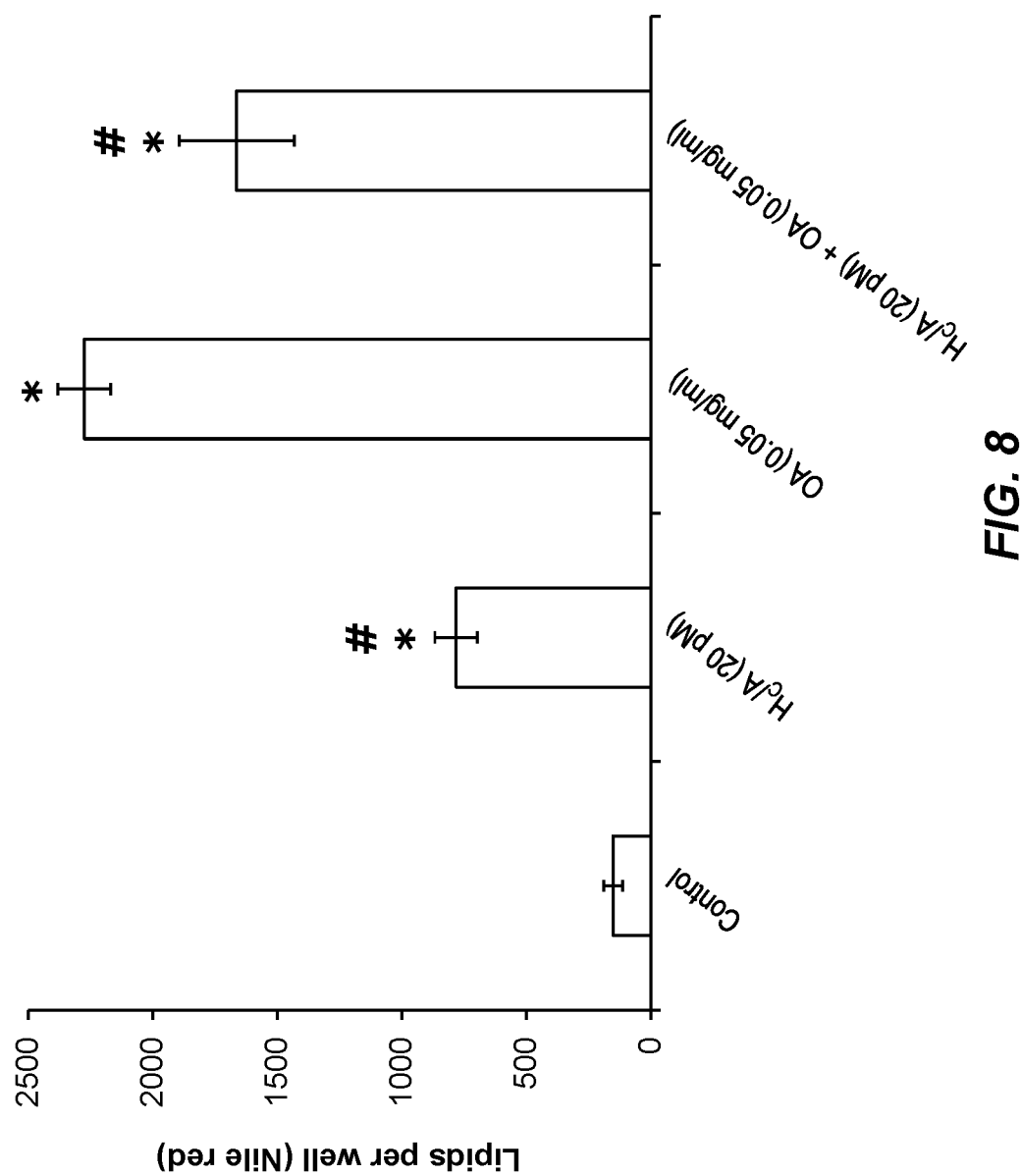
FIG. 8 is a graph showing increase in sebocyte lipogenesis upon treatment of sebocyte cells (SEB-1) with 20 pM of the exemplary polypeptide of SEQ ID NO: 19 or oleic acid (OA), and reduction of OA-induced sebocyte lipogenesis upon co-treatment with the exemplary polypeptide of SEQ ID NO: 19. The * indicates statistical significance of p<0.05 compared to the control. The # indicates statistical significance of p<0.05 compared to treatment with OA alone.

The results shown in FIG. 8, demonstrate that sebum lipogenesis was significantly enhanced by 20 pM of the polypeptide of SEQ ID NO: 19 (~5-fold) or oleic acid (OA) treatment (~15-fold). However, co-treatment of the cell with 20 pM of the polypeptide of SEQ ID NO: 19 significantly reduced the lipogenesis enhancement effect of OA (reduction of approximately 30-25%). The results suggest that polypeptides corresponding substantially to the binding domain of BoNT/A ($H_C$/A) can affect sebocyte cells within sebaceous glands in vivo, for example by modulating skin sebum production and/or composition and whereby affects skin oiliness/dryness in human patients.

Example 11

Use of an Exemplary Polypeptide Provided in Accordance with Aspects of the Present Disclosure Modulate Production of Sebum Lipids in a Dose Dependent Manner Treatment of sebocyte cells (SEB-1) with a polypeptide having an amino acid sequence substantially identical to the amino acid sequence of the binding domain of BoNT/A ($H_C$/A) modulated lipogenesis in a dose dependent manner. Briefly, human immortalized sebocyte cells (SEB-1) were cultured in sebocyte growth medium (Zen-Bio®). The following treatments were added to the growth medium for 1 day: control (no treatment); oleic acid (OA) (0.05 mg/mL); the exemplary polypeptide of SEQ ID NO: 19 at 2pM, 20 pM, or 200 pM; oleic acid (OA) (0.05 mg/mL) and polypeptide of SEQ ID. NO.:19 at 2pM, 20 pM, or 200 pM. The total amount of sebum lipids was measured using a Nile Red lipid droplets fluorescence assay (Cayman Chemical, Cat. #500001), wherein the cells were fixed with 10% formalin and then incubated with Nile Red staining solution. Fluorescence intensities (Nile red, FITC, excitation/emission 485/535 nm, DAPI, excitation: 358 nm; emission: 461 nm) were measured using a fluorescent plate reader (Hidex Plate CHAMELEON™ V multilabel microplate reader, Bioscan, Inc). The lipid values were normalized to the DAPI values and graphed as "Lipids per cell (Nile red/DAPI)."

Figure 9:
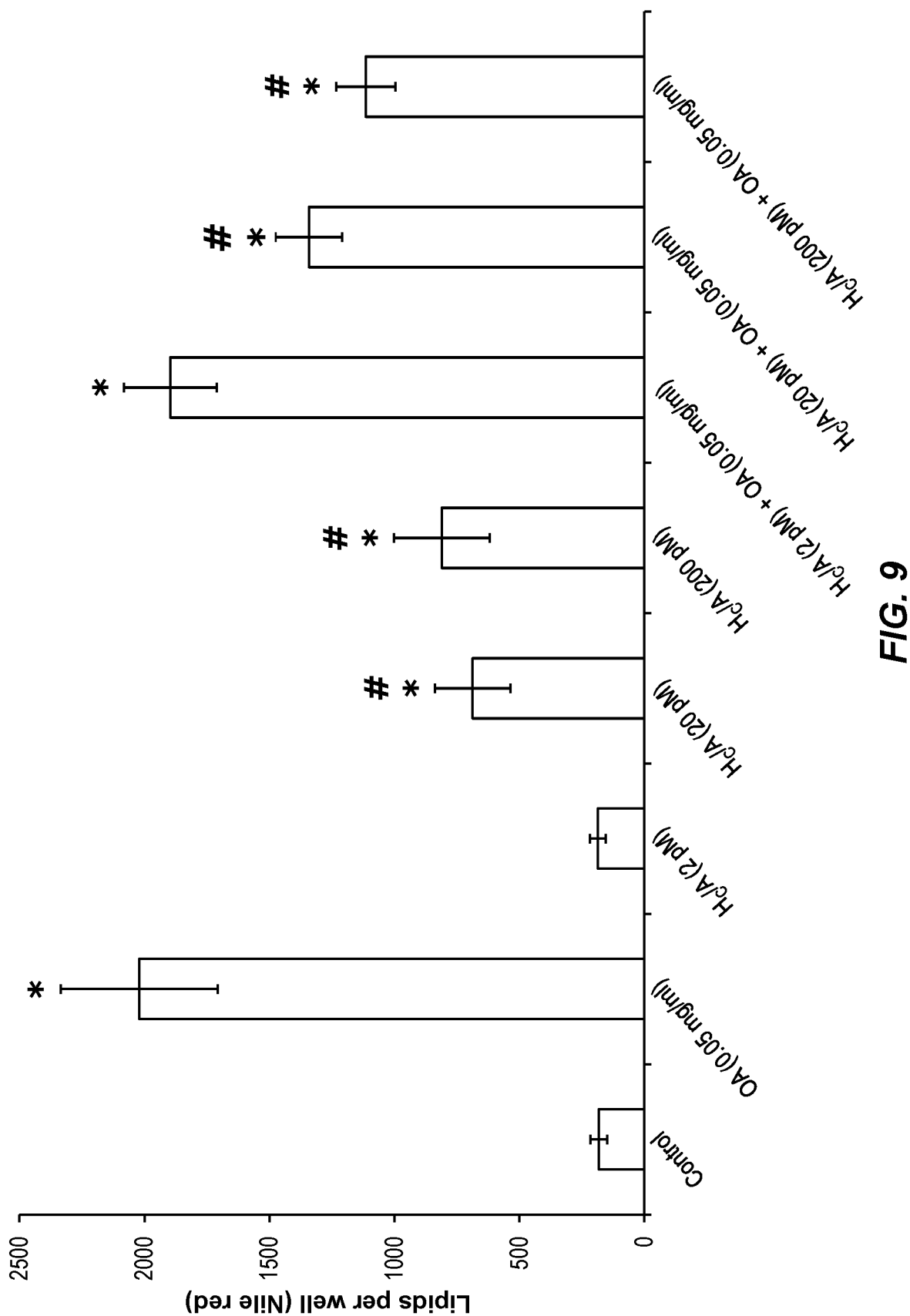
FIG. 9 is a graph showing increase in sebocyte lipogenesis upon treatment of sebocyte cells (SEB-1) with oleic acid (OA) or the exemplary polypeptide of SEQ ID NO: 19 at 2 pM, 20 pM and 200 pM and reduction in OA-induced sebocyte lipogenesis upon co-treatment with the exemplary polypeptide of SEQ ID NO: 19 at 2 pM, 20 pM and 200 pM. The * indicates statistical significance of p<0.05 compared to the control. The # indicates statistical significance of p<0.05 compared to treatment with OA alone.

The results shown in FIG. 9, demonstrate that sebum lipogenesis was significantly enhanced by either oleic acid (OA) treatment (~11-fold) or by the polypeptide of SEQ ID NO: 19 (~4-5-fold) in a dose dependent manner. However, co-treatment of the cell with 20 pM or 200 pM of the polypeptide of SEQ ID NO: 19 significantly reduced the lipogenesis enhancement effect of OA (reduction of approximately 35-45%). The results suggest that polypeptides corresponding substantially to the binding domain of BoNT/A ($H_C$/A) can affect sebocyte cells within sebaceous glands in vivo, for example by modulating skin sebum production and/or composition and whereby affects skin oiliness/dryness in human patients.

Example 12

Use of an Exemplary Polypeptide Provided in Accordance with Aspects of the Present Disclosure to Treat Acne A 20-year nonsmoking male with phototype II skin presents with mild-moderate facial acne vulgaris, based on Investigator's Global Assessment (IGA) for acne severity, with 30 acne lesions in the face, and receives intradermal treatment with a polypeptide having an amino acid sequence which is substantially identical to the binding domain of BoNT/A ($H_C$/A).

The polypeptide powder is dissolved in saline, 4.5 ng vacuum-dried powder is dissolved in 0.25 mL of sterile 0.9% saline to constitute a solution at 1.8 ng/0.1 mL; and injected into his forehead. A total of 3.6 ng is injected. Twenty (20) injection sites are chosen, 5 in the forehead, 4 on each cheek, and 6 in the lower face, around the mouth and the chin; and 0.36 ng of $H_C$/A polypeptide is injected intradermally (ID) at each site using a 30-G needle. An ice pack is applied after treatment.

Evaluation by Investigator's Global Assessment (IGA) for acne severity and counting the number of acne lesion is conducted at baseline and at 12 weeks' post-treatment.

Compared to baseline, at 12 weeks' post-treatment, his acne is improved from mild-moderate to mild to almost clear, based on IGA for acne severity, with only 5 acne lesions and the patient reports that he is satisfied with the result.

Example 13

Use of an Exemplary Polypeptide Provided in Accordance with Aspects of the Present Disclosure to Treat Acne A 20-year nonsmoking male with phototype II skin presents with mild-moderate facial acne vulgaris, based on Investigator's Global Assessment (IGA) for acne severity, with 30 acne lesions in the face, and receives treatment with dissolving microneedle patches containing a polypeptide having an amino acid sequence which is substantially identical to the binding domain of BoNT/A ($H_C$/A).

Dissolving micro-needle patches for transdermal drug delivery containing encapsulated 2.5 ng of polypeptide per patch, is applied to the affected areas using an applicator. A total of six patches (15 ng) is applied, 2 in the forehead, 2 on each cheek, and 2 in the lower face, around the mouth and the chin. The patches are applied for 5 minutes to allow the needles to dissolve, and then the remaining backing is removed.

Evaluation by Investigator's Global Assessment (IGA) for acne severity and counting the number of acne lesion is conducted at baseline and at 12 weeks' post-treatment.

Compared to baseline, at 12 weeks' post-treatment, his acne is improved from mild-moderate to mild to almost clear, based on IGA for acne severity, with only 5 acne lesions and the patient reports that he is satisfied with the result.

Unless otherwise defined, all technical and scientific terms used herein have the same meaning as commonly understood by one of ordinary skill in the art to which this disclosure belongs.

Although methods and materials similar or equivalent to those described herein can be used in the practice or testing of the present disclosure, suitable methods and materials are described in the foregoing paragraphs. In addition, the materials, methods, and examples are illustrative only and not intended to be limiting. In case of conflict, the present specification, including definitions, will control.

All United States patents and published or unpublished United States patent applications cited herein are incorporated by reference. All published foreign patents and patent applications cited herein are hereby incorporated by reference. All published references, documents, manuscripts, scientific literature cited herein are hereby incorporated by reference. All identifier and accession numbers pertaining to scientific databases referenced herein (e.g., PUBMED, NCBI, GENBANK, EBI) are hereby incorporated by reference.

We claim:

1. A method for treating an infection associated with sebum dysregulation and/or abnormalities in a subject, comprising:
    administering to the subject a composition comprising an effective amount of a polypeptide consisting of the amino acid sequence set forth in SEQ ID NO: 1, wherein treating the infection associated with sebum dysregulation and/or abnormalities does not involve paralysis of a facial muscle.

2. The method of claim 1, wherein the infection comprises infections from bacteria, viruses, fungi, yeast, and mites.

3. A method for treating a skin disorder associated with sebum dysregulation and/or abnormalities in a subject, comprising:
    administering to the subject a composition comprising an effective amount of a polypeptide consisting of the amino acid sequence set forth in SEQ ID NO: 1, wherein treating the skin disorder associated with sebum dysregulation and/or abnormalities does not involve paralysis of a facial muscle.

4. The method of claim 3, wherein the skin disorder is selected from the group consisting of acne, seborrheic dermatitis, erythema, rosacea, psoriasis, atopic dermatitis (AD), alopecia, vitiligo, allergies, infection, and inflammation.

* * * * *